US009556440B2

(12) United States Patent
Lale et al.

(10) Patent No.: US 9,556,440 B2
(45) Date of Patent: Jan. 31, 2017

(54) ENHANCED EXPRESSION FROM THE PM PROMOTER

(75) Inventors: Rahmi Lale, Trondheim (NO); Laila Berg, Trondheim (NO); Ingrid Bakke, Ranheim (NO); Trond Erik Vee Aune, Trondheim (NO); Svein Valla, Vikhammer (NO)

(73) Assignee: VECTRON BIOSOLUTIONS AS, Trondheim (NO)

( * ) Notice: Subject to any disclaimer, the term of this patent is extended or adjusted under 35 U.S.C. 154(b) by 847 days.

(21) Appl. No.: 12/520,139

(22) PCT Filed: Dec. 20, 2007

(86) PCT No.: PCT/GB2007/004903
§ 371 (c)(1),
(2), (4) Date: Oct. 15, 2009

(87) PCT Pub. No.: WO2008/075057
PCT Pub. Date: Jun. 26, 2008

(65) Prior Publication Data
US 2010/0048426 A1 Feb. 25, 2010

(30) Foreign Application Priority Data
Dec. 21, 2006 (GB) .................................. 0625651.5

(51) Int. Cl.
*C12N 15/67* (2006.01)
*C07K 14/21* (2006.01)
*C12N 9/92* (2006.01)

(52) U.S. Cl.
CPC ............... *C12N 15/67* (2013.01); *C07K 14/21* (2013.01); *C12N 9/92* (2013.01)

(58) Field of Classification Search
None
See application file for complete search history.

(56) References Cited

U.S. PATENT DOCUMENTS 6,258,565 B1   7/2001   Blatny et al.

FOREIGN PATENT DOCUMENTS

| WO | 9808958 A1 | 3/1998 |
| WO | 0068375 A2 | 11/2000 |
| WO | 2008015447 A2 | 2/2008 |

OTHER PUBLICATIONS

Ohki et al., J. Bacteriol., 186 (21):7450-7455, 2004.*
Fournier et al., J. Bacteriol., 183 (7): 2367-2371, 1999.*
Bolivar et al, "Construction and Characterization of New Cloning Vehicles," Gene, vol. 2, pp. 75-93, 1977.
Uhlin et al, "R Plasmid Gene Dosage Effects in *Escherichia coli* K-12: Copy Mutants of the R Plasmid R1drd-19," Plasmid, vol. 1, pp. 1-7, 1977.
Inouye et al, "Molecular Cloning of Gene xylS of the TOL Plasmid: Evidence for Positive Regulation of the xylDEGF Operon by xylS," Journal of Bacteriology, vol. 148, No. 2, pp. 413-418, Nov. 1981.
Inouye et al, "Nucleotide Sequence of the Promoter Region of the xylDEFG Operon on the TOL Plasmid of Pseudomonas Putida," Gene, vol. 29, pp. 323-330, 1984.
Wells et al, "Cassette Mutagenesis: an Efficient Method for Generation of Multiple Mutations at Defined Sites," Gene, vol. 34, pp. 315-323, 1985.
Coleman et al, "Mutations Upstream of the Ribosome-Binding Site Affect Translational Efficiency," Journal of Molecular Biology, vol. 181, pp. 139-143, 1985.
Mermod et al, "Vector for Regulated Expression of Cloned Genes in a Wide Range of Gram-Negative Bacteria," Journal of Bacteriology, vol. 167, No. 2, pp. 447-454, Aug. 1986.
Ramos et al, Redesigning Metabolic Routes: Manipulation of TOL Plasmid Pathway for Catabolism of Alkylbenzoates, Science, vol. 235, No. 4788, pp. 593-596, Jan. 30, 1987.
Ramos et al, "Broad-Host Range Expression Vectors Containing Manipulated Meta-Cleavage Pathway Regulatory Elements of the TOL Plasmid," FEBS Letters, vol. 226, No. 2, pp. 241-246, Jan. 1988.
Ramos et al, "Signal-Regulator Interactions. Genetic Analysis of the Effector Binding Site of xylS, the Benzoate-Activated Positive Regulator of Pseudomonas TOL Plasmid Meta-Cleavage Pathway Operon," The Journal of Molecular Biology, vol. 211, pp. 373-382, 1990.
Adhin et al, "Scanning Model for Translational Reinitiation in Eubacteria," The Journal of Molecular Biology, vol. 213, pp. 811-818, 1990.
Zhou et al, "Mutations Leading to Constitutive Expression from the TOL Plasmid Meta-Cleavage Pathway Operon Are Located at the C-Terminal End of the Positive Regulator Protein xylS," Journal of Bacteriology, vol. 172, No. 7, pp. 3707-3719, Jul. 1990.
Fjaevik et al, "Complementation of Cellulose-Negative Mutants of Acetobacter Xylinum by the Cloned Structural Gene for Phosphoglucomutase," FEMS Microbiology Letters, vol. 77, pp. 325-330, 1991.
Michan et al, "XylS Domain Interactions can be Deduced from Intraallelic Dominance in Double Mutants of Pseudomonas Putida," Molecular & General Genetics, vol. 235, pp. 406-412, 1992.

(Continued)

*Primary Examiner* — Nancy T Treptow
(74) *Attorney, Agent, or Firm* — Porter Wright Morris & Arthur LLP

(57) ABSTRACT

The present invention concerns a method of producing a desired gene product in a recombinant gene expression system, said method comprising expressing said gene from a Pm promoter-based expression system using at least two mutant elements selected from: (i) a mutant Pm promoter; (ii) a mutant mRNA leader; and (iii) a mutant XylS; wherein said mutant elements each comprise one or more mutations which enhance expression of said desired gene. Particularly combinations of a mutant Pm promoter and a mutant mRNA leader are concerned. Isolated nucleic acid molecules, vectors, host cells, libraries, expression systems, methods of enhancing expression, obtaining nucleic acid molecules and identifying combination mutants which enhance expression, artificially constructed operons and their uses are also encompassed.

27 Claims, 9 Drawing Sheets

(56) References Cited

OTHER PUBLICATIONS

Figure 2:
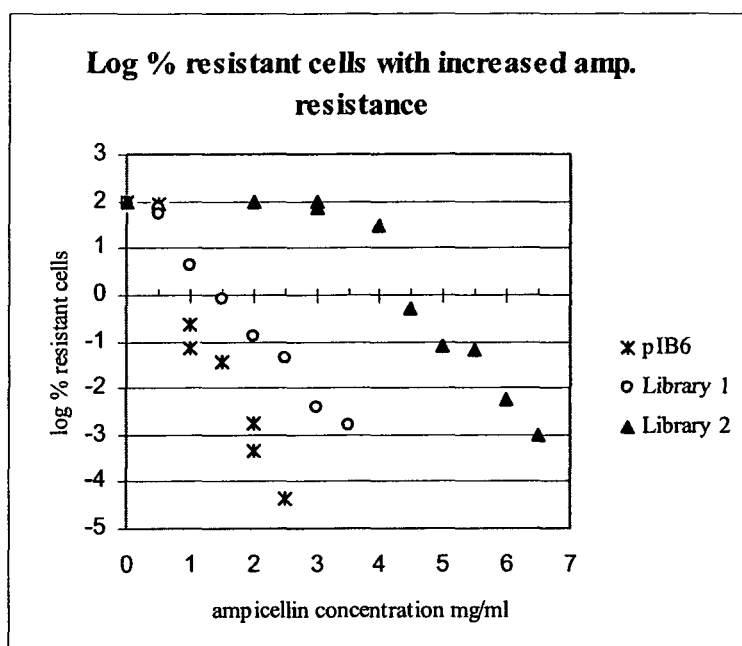

Michan et al, "Identification of Critical Amino-Terminal Regions of xylS," The Journal of Biological Chemistry, vol. 267, No. 32, pp. 22897-29901, Nov. 15, 1992.
Haugan et al, The Phenotypes of Temperature-Sensitive Mini-RK2 Replicons Carrying Mutations in the Replication Control Gene trfA are Suppressed Nonspecifically by Intragenic cop Mutations, Journal of Bacteriology, vol. 174, No. 21, pp. 7026-7032, Nov. 1992.
Kessler et al, "Identification of a cis-acting Sequence within the Pm Promoter of the TOL Plasmid which Confers xylS-Mediated Responsiveness to Substituted Benzoates," Journal of Molecular Biology, vol. 230, pp. 699-703, 1993.
De Smit et al, "Control of Translation by mRNA Secondary Structure in *Escherichia coli*," Journal of Molecular Biology, vol. 244, pp. 144-150, 1994.
Stemmer, "DNA Shuffling by Random Fragmentation and Reassembly: In vitro Recombination for Molecular Evolution," Proceedings of the National Academy of Sciences of the United State of America, vol. 91, pp. 10747-10751, Oct. 1994.
Chervaux et al, "Secretion of Active b-Lactamase to the Medium Mediated by the *Escherichia coli* Haemolysin Transport Pathway," Molecular & General Genetics, vol. 249, pp. 237-245, 1995.
Ramos et al, "Transcriptional Control of the Pseudomonas TOL Plasmid Catabolic Operons is Achieved Through an Interplay of Host Factors and Plasmid-Encoded Regulators," Annual Review of Microbiology, vol. 51, pp. 341-372, 1997.
Blatny et al, "Construction and Use of a Versatile Set of Broad-Host-Range Cloning and Expression Vectors Based on the RK2 Replicon," Applied and Environmental Microbiology, vol. 63, No. 2, pp. 370-379, Feb. 1997.
Blatny et al, "Improved Broad-Host-Range RK2 Vectors Useful for High and Low Regulated Gene Expression Levels in Gram-Negative Bacteria," Plasmid, vol. 38, pp. 35-51, 1997.
Marques et al, "The xylS-Dependent Pm Promoter is Transcribed In Vivo by RNA Polymerase with σ32 or σ38 Depending on the Growth Phase," Molecular Microbiology, vol. 31, No. 4, pp. 1105-1113, 1999.
Gonzalez-Perez et al, "Critical Nucleotides in the Upstream Region of the xylS-Dependent TOL Meta-Cleavage Pathway Operon Promoter as Deduced from Analysis of Mutants," The Journal of Biological Chemistry, vol. 274, No. 4, pp. 2286-2290, Jan. 22, 1999.
Kozak, "Initiation of Translation in Prokaryotes and Eukaryotes," Gene, vol. 214, pp. 187-208, 1999.
Winther-Larsen et al, "Parameters Affecting Gene Expression from the Pm Promoter in Gram-Negative Bacteria," Metabolic Engineering, vol. 2, pp. 79-91, 2000.
Winther-Larsen et al, "Pm Promoter Expression Mutants and Their Use in Broad-Host-Range RK2 Plasmid Vectors," Metabolic Engineering, vol. 2, pp. 92-103, 2000.
Brautaset et al, "In vitro Determined Kinetic Properties of Mutant Phosphoglucomutases and Their Effects on Sugar Catabolism in *Escherichia coli*," Metabolic Engineering, vol. 2, pp. 104-114, 2000.
Andre et al, "Reinitiation of Protein Synthesis in *Escherichia coli* can be Induced by mRNA cis-elements Unrelated to Canonical Translation Initiation Signals," FEBS Letters, vol. 468, pp. 73-78, 2000.
Manzanera et al, "Mutational Analysis of the Highly Conserved C-Terminal Residues of the xylS Protein, a Member of the AraC Family of Transcriptional Regulators," FEBS Letters, vol. 476, pp. 312-317, 2000.
Matsumura et al, "Mutagenic Polymerase Chain Reaction of Protein-Coding Genes for In vitro Evolution," Methods in Molecular Biology, vol. 182, pp. 259-267, 2001.

Gaal et al, "Promoter Recognition and Discrimination by Eσs RNA Polymerase," Molecular Microbiology, vol. 42, No. 4, pp. 939-954, 2001.
Castan et al, "Multiple Regulatory Mechanisms Act on the 5' Untranslated Region of the S-Layer Gene from Thermus Thermophilus HB8," Journal of Bacteriology, vol. 183, No. 4, pp. 1491-1494, Feb. 2001.
Santos et al, "New Broad-Host-Range Promoter Probe Vectors Based on the Plasmid RK2 Replicon," FEMS Microbiology Letters, vol. 195, pp. 91-96, 2001.
Ruiz et al, "Residues 137 and 153 of xylS Influence Contacts with the C-Terminal Domain of the RNA Polymerase α Subunit," Biochemical and Biophysical Research Communications, vol. 287, pp. 519-521, 2001.
Ruiz et al, "Residues 137 and 153 at the N Terminus of the xylS Protein Influence the Effector Profile of this Transcriptional Regulator and the σ Factor Used by RNA Polymerase to Stimulate Transcription from Its Cognate Promoter," The Journal of Biological Chemistry, vol. 277, No. 9, pp. 7282-7286, Mar. 1, 2002.
Walker et al, "Factors Affecting Start Site Selection at the *Escherichia coli* fis Promoter," Journal of Bacteriology, vol. 184, No. 17, pp. 4783-4791, Sep. 2002.
Gonzalez-Perez et al, "XylS Activator and RNA Polymerase Binding Sites at the Pm Promoter Overlap," FEBS Letters, vol. 519, pp. 117-122, 2002.
Hsu, "Promoter Clearance and Escape in Prokaryotes," Biochimica et Biophysica Acta, vol. 1577, pp. 191-207, 2002.
Vo et al, "In vitro Studies of Transcript Initiation by *Escherichia coli* RNA Polymerase. 3. Influences of Individual DNA Elements Within the Promoter Recognition Region on Abortive Initiation and Promoter Escape," Biochemistry, vol. 42, pp. 3798-3811, 2003.
Ruiz et al, "Leucines 193 and 194 at the N-Terminal Domain of the xylS Protein, the Positive Transcriptional Regulator of the TOL meta-Cleavage Pathway, Are Involved in Dimerization," Journal of Bacteriology, vol. 185, No. 10, pp. 3036-3041, May 2003.
Lewis et al, "Axiom of Determining Transcription Start Points by RNA Polymerase in *Escherichia coli*," Molecular Microbiology, vol. 54, No. 3, pp. 692-701, 2004.
Liu et al, "A Mutant Spacer Sequence Between -35 and -10 Elements Makes the Plac Promoter Hyperactive and cAMP Receptor Protein-Independent," Proceedings of the National Academy of Sciences of the United States of America, vol. 101, No. 18, pp. 6911-6916, May 4, 2004.
Lacour et al, "σs-Dependent Gene Expression at the Onset of Stationary Phase in *Escherichia coli*: Function of σs-Dependent Genes and Identification of Their Promoter Sequences," Journal of Bacteriology, vol. 186, No. 21, pp. 7186-7195, Nov. 2004.
Sletta et al, "Broad-Host-Range Plasmid pJB658 Can Be Used for Industrial-Level Production of a Secreted Host-Toxic Single-Chain Antibody Fragment in *Escherichia coli*," Applied and Environmental Microbiology, vol. 70, No. 12, pp. 7033-7039, Dec. 2004.
Komarova et al, "AU-Rich Sequences Within 5' Untranslated Leaders Enhance Translation and Stabilize mRNA in *Escherichia coli*," Journal of Bacteriology, vol. 187, No. 4, pp. 1344-1349, Feb. 2005.
Bakkevig et al, "Role of the Pseudomonas Fluorescens Alginate Lyase (AlgL) in Clearing the Periplasm of Alginates Not Exported to the Extracellular Environment," Journal of Bacteriology, vol. 187, No. 24, pp. 8375-8384, Dec. 2005.
Sletta, "The Presence of N-Terminal Secretion Signal Sequences Leads to Strong Stimulation of the Total Expression Levels of Three Tested Medically Important Proteins During High-Cell-Density Cultivations of *Escherichia coli*," Applied and Environmental Microbiology, vol. 73, No. 3, pp. 906-912, Feb. 2007.

* cited by examiner

Figure 1
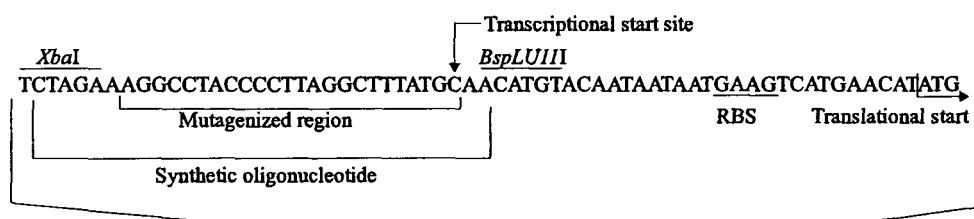
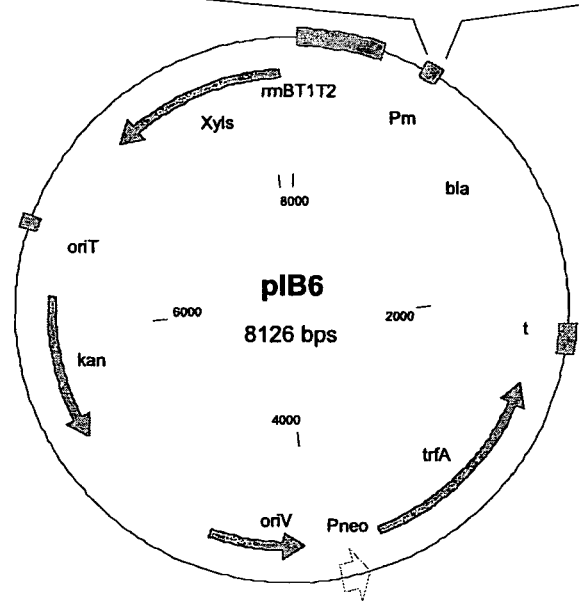

Figure 3

A

|   |   | amp. resistance mg/ml | |
|---|---|---|---|
|   |   | +m-tol | ÷m-tol |
|   | XbaI                               BspLU11I | | |
| wt  | tctagaaaggcctaccccttaggctttatgCaacatgt | 0.5 | 0.0025 |
| m6  | ................................-... | 1.5 | 0.0025 |
| 12B | ...............................--... | 1.5 | 0.005 |
| m5  | ..........g.t....g..t...........-... | 3.0 | 0.065 |
| 5D  | ..........tt........ta..........--... | 3.0 | 0.8 |
| 4H  | ........c.......tg..............--... | 3.0 | 0.15 |
| 11H | ........c..t...a.a..............--... | 2.5 | 0.015 |
| 1D  | ...........a....tg..............--... | 2.5 | 0.03 |
| 7F  | ................a...a...........--... | 2.5 | 0.03 |
| 1C  | ................g...c............--... | 2.5 | 0.015 |
| 4B  | ................g...t............--... | 3.0 | 0.1 |
| m8  | ........act......g....-c.........--... | 2.5 | 0.015 |
| m7  | ..........aaa........c...a.......--... | 3.0 | 0.1 |
| 3G  | ......t......t......t....-......-... | 3.0 | 0.15 |
| m1  | ......t.c....t.t.........-.......... | 2.5 | 0.005 |
| m2  | ......t...a.............-........... | 2.5 | 0.005 |
| 11G | ......ta.a..........a...-........... | 3.0 | 0.015 |
| 4E  | .......ta........a....·......-...... | 3.0 | 0.005 |
| 7B  | ....................aa.....-...-.... | 3.5 | 0.030 |

B

|   |   | amp. resistance mg/ml | |
|---|---|---|---|
|   |   | +m-tol | ÷m-tol |
| wt  | tctagaaaggcctaccccttaggctttatgcaacatgt | 0.5 | 0.0025 |
| Un3 | ................tg....a...-....-...... | 2.5 | 1.0 |
| 5d  | ..........tt.........ta..........--.... | 3.0 | 0.8 |
| Un19| ............a..gtg..................... | 2.5 | 0.6 |
| Un21| ..............t.gtg.................... | 2.5 | 0.6 |

C

|   |   | amp. resistance mg/ml | |
|---|---|---|---|
|   |   | +m-tol | ÷m-tol |
| 7B    | tctagaaaggcctaccccttaaactttagcaCatgt | 3.5 | 0.030 |
| 7-2d  | ........t.............t............. | 4.0 | 0.2 |
| 7-2g  | ..........a......t.g................ | 4.5 | 0.065 |
| 7-3b  | ........t...........c............... | 4.0 | 0.03 |
| 7-4c  | ........a.....a..............c....... | 4.0 | 0.03 |
| 7-4g  | .......c........a........a........... | 4.5 | 0.1 |
| 7-4h  | ........ca........................... | 4.0 | 0.03 |
| 7-5b  | .......c...g....g.................... | 4.0 | 0.065 |
| 7-5d  | .......c............................. | 4.0 | 0.065 |
| 7-5f  | ..........tt.c....................... | 4.0 | 0.03 |
| 7-5h  | ...........a..........t.............. | 4.0 | 0.2 |
| 7-10f | ............a.t......c............... | 4.0 | 0.15 |
| 7-11h | ............a.t......c............... | 4.0 | 0.2 |

Figure 4:
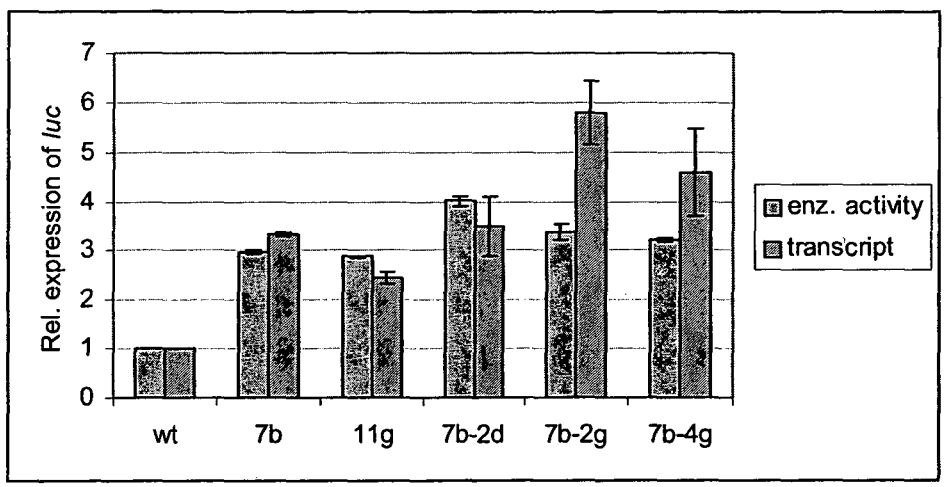

Figure 4
A
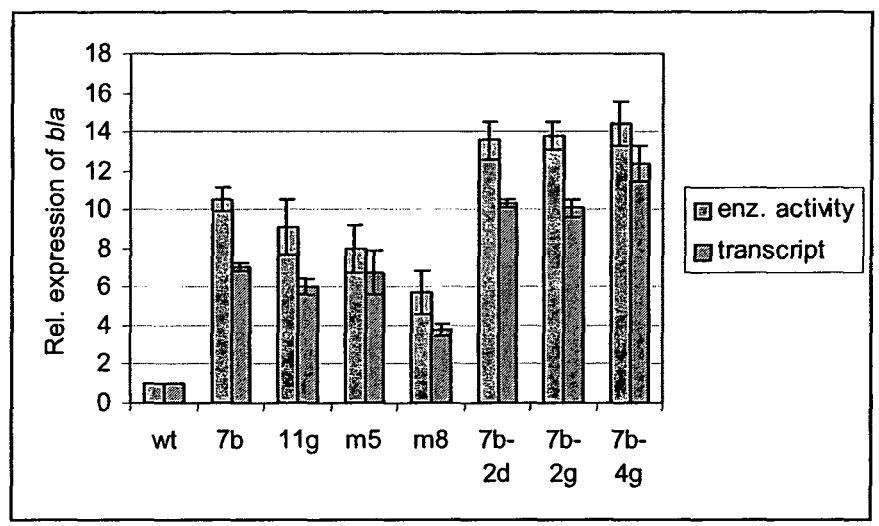
B
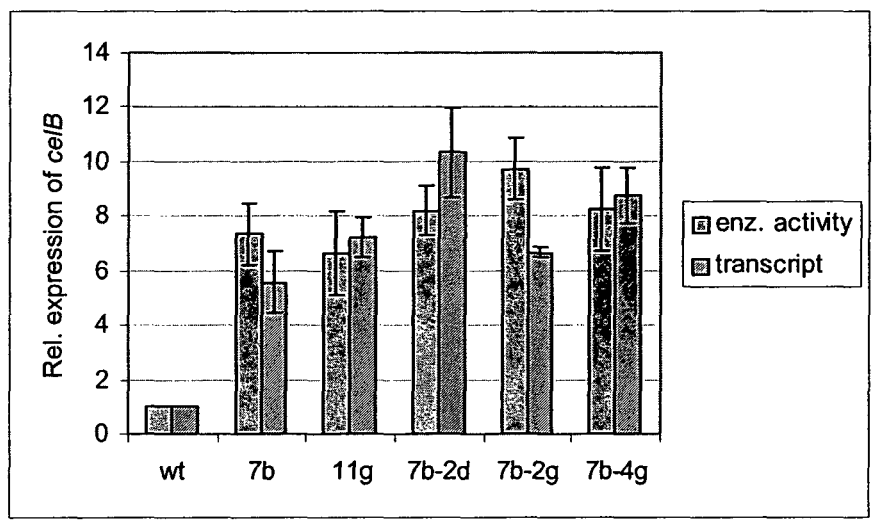

A

B

```
wt   tctagaaaggcctaccccttaggctttatgCaacatgt
3G   tctagaatggcctatcccttatgcttatgcaAatgt
5D   tctagaaaggtttaccccttatactttatgCaatgt
7B   tctagaaaggcctaccccttaaactttagCacatgt
11g  tctagaatagactaccccttagacttatgcAaCatgt
```

Figure 6

A

```
              XbaI                        BspLU11I
Pm-wt       tctagaaaggcctaccccttaggctttatgCaacatgt
Pm-7B-4g    .......c........a....aa..a..-...-....
Pm-7b-2g    ................a.....tag....-...-....
```

B

```
                    BspLU11I                        NdeI         amp. res. mg/ml (0,1 mM m-tol)
Pm-7b4g-UTR-wt     acatgtacaataataatggagtcatgaacatatg   0,5
Pm-7b4g-UTR-C2     ..........c....t.....a............   12
Pm-7b4g-UTR-A2     ..........c..........a............   8
Pm-7b4g-UTR-C4     ........t....t.....a..............   10 (11)
Pm-7b4g-UTR-H2     ..........c..........a....t........   11
Pm-7b4g-UTR-E2     ...............t.....a....t........   9 (10)
Pm-7b4g-UTR-B2     ..........a.c........a....t........   11
Pm-7b4g-UTR-F3     ......t..............a....t........   12 (13)
Pm-7b4g-UTR-E6     ..............ta...a....t........    11 (12)
Pm-7b4g-UTR-H3     .............a.c.....a....t........   11
Pm-7b4g-UTR-F11    ..........c.a........a............   11
Pm-7b4g-UTR-B3     ............ta..c...ac............   11 (12)
Pm-7b4g-UTR-A3     ..........c.ta.......a............   13
Pm-7b4g-UTR-2      ......t....c.........a....t........   11 (12)
Pm-7b4g-UTR-C3     .........g.c.tt....a..............   9 (10)
Pm-7b4g-UTR-E3     ......t..............a.....c.......   12
Pm-7b4g-UTR-G3     ..........c...g.....a..............   13
Pm-7b4g-UTR-F2     ..........c..a..gc.....c...........   12 (13)
```

ENHANCED EXPRESSION FROM THE PM PROMOTER

RELATED APPLICATION

This application is a 371 of PCT/GB2007/004903 filed Dec. 20, 2007.

The present invention concerns a method for producing a desired gene product at increased or enhanced levels, and isolated nucleic acid molecules, constructs and expression systems for use in such a method. In particular, in one embodiment the invention is based upon using, for expression of the desired gene, a modified (or mutant) Pm promoter, which comprises one or more mutations which enhance gene expression, together with a modified (or mutant) mRNA leader which comprises one or more mutations which enhance expression of the desired gene. The present invention thus lies in the concept of combining a modified or mutant Pm promoter, which has been modified to enhance expression, with a modified or mutant mRNA leader, which may or may not be the Pm leader, and which enhances expression of the desired gene. Thus a modified Pm-based expression system is presented which combines expression-enhancing mutations in the promoter and the mRNA leader, from which the desired gene is expressed. Advantageously, mutant Pm promoter and mRNA leader libraries may be created, and Pm and leader mutants may be particularly selected which enhance expression of the desired gene. Accordingly, the invention further provides a method of identifying and/or screening for mutations in Pm and in the region encoding the mRNA leader which result in enhanced expression of the gene product.

The Pm promoter is regulated by the regulatory protein XylS (which is activated by the effector molecules which "induce" the Pm promoter). As described in more detail below, further work has shown that mutations in xylS, the gene encoding XylS, may also advantageously result in enhanced expression of a desired gene under the control of a Pm promoter, and such xylS mutant genes may further be combined with an expression-enhancing mutant Pm promoter and/or a mutant mRNA leader. Thus, in a broader embodiment, the present invention provides a modified Pm-based expression system which comprises expression-enhancing mutants in any two or more of Pm, mRNA leader and xylS. Thus analogously to the modified Pm/mRNA leader system described above, mutant xylS gene libraries may be constructed, optionally in combination with mutant Pm and/or mRNA leader libraries and mutants may be selected with expression-enhancing mutations in any two or more of Pm/mRNA leader/xylS, which enhance expression of the desired gene.

The cloning and expression of genes is a long-established and central tool in biotechnology. So-called recombinant gene expression has been widely used for the commercial or industrial production of desired gene products, or proteins. A wide range of expression systems and vectors have been developed, principally for use in bacteria, to enable such recombinant gene expression. The expression control elements (e.g. promoters and such like) used in such expression systems may be of importance in maximising the efficiency and control of gene expression and thus of biotechnological processes.

The mechanisms underlying gene expression have been extensively studied in many organisms due to their fundamental importance for the understanding of cell function and for application in biotechnology. It is particularly important to have an understanding of the mechanisms affecting expression in recombinant protein production, to establish which factors may affect the level of expression.

It is well known in the art that protein production occurs through two basic steps, namely transcription (to form mRNA from the DNA template) and translation (of the mRNA to form a protein). Transcription can be delineated into three phases—initiation, elongation and termination. Hence, initiation of transcription begins with the binding of RNA polymerase to the promoter and ends with the conversion of the DNA and enzyme into an elongation complex. In between these steps, the polymerase and promoter undergo a series of alterations that include promoter binding and activation and RNA chain initiation and promoter escape. Promoter binding has been extensively studied in both prokaryotes and eukaryotes, where the interactions between RNA polymerase with general transcription factors, promoter specific factors and DNA sequences of the recognition regions of promoters have been investigated. The promoter binding-activation phase leads to the formation of the open promoter complex which interacts with NTP substrates to initiate transcription. Short RNA transcripts can then usually form which can be elongated if the polymerase escapes the promoter and moves downstream.

Promoter escape is the last stage of transcription initiation where the RNA polymerase should leave the promoter region and advance to downstream regions. If the RNA polymerase has a poor ability to escape the promoter, then abortive transcripts may be produced. Hence, the initial transcribing complexes carry out repeated initiation and abortive release without promoter escape (Hsu, *Biochimia et Biophysics Acta*, 1577, 191-207, 2002). In vitro studies have shown that changes in the promoter recognition region (from −60 to −1) may affect the abortive rate, probability and size of abortive transcripts (Vo et al, *Biochemistry*, 42, 3798-3811, 2003).

Hence, changes in the promoter and its recognition region have been studied in the art. Particularly, since the promoter plays an important part in the control of transcription, mutations in the promoter region have been previously studied to determine their effect on gene expression. For example, we have shown that mutations in the Pm promoter at the −10 region which lies upstream of the transcriptional start site may facilitate gene-independent enhancement or reduction of expression and/or improved regulatory control of recombinant gene expression (WO 00/68375).

The Pm/xylS promoter system drives the expression of the meta-operon carried by the *Pseudomonas putida* TOL plasmid pWWO. The gene products of this operon are involved in catabolism of alkylbenzoates, and are expressed in response to meta pathway substrates (reviewed in Ramos et al. *Annu. Rev. Microbiol.* 51:342-372, 1997). XylS positively regulates Pm by forming an activated complex with benzoate effectors (Inouye et al. *J. Bacteriol.* 148(2): 413-418, 1981). Transcriptional activation occurs through binding of the activated XylS to two direct imperfect repeats located directly upstream of the −35 region of Pm (Gonzalez-Perez et al. *FEBS Lett.* 519(1-3): 117-122, 2002).

The Pm/xylS promoter system has been shown to function in a wide range of gram negative bacterial species, and has been found useful for over-expression of recombinant proteins (Mermod et al., *J. Bacteriol.* 167(2):447-454, 1986; Ramos et al. *FEBS Lett*, 226(2):241-246, 1988; Blatny et al. *Plasmid*. 38:35-51, 1997). The uninduced expression level from Pm is low, and the use of different effector compounds at various concentrations can be used to regulate the level of induced expression (Winther-Larsen et al. *Metab. Eng.* 2:79-

91, 2000). Many of the inducers are low-cost compounds that enter the cell by passive diffusion.

The Pm/xylS expression system has been used in the construction of broad-host range expression vectors based on the RK2 minimal replicon (Blatny et al., *Appl. Environ. Microbiol.* 63(2):370-379 1997; Blatny et al, *Plasmid.* 38:35-51, 1997; and WO98/08958). One of these vectors, pJB658, has proven useful for tightly regulated recombinant gene expression in several gram-negative species (Blatny et al. *Appl. Environ. Microbiol.* 63(2):370-379, 1997; Blatny et al, *Plasmid.* 38:35-51, 1997; Brautaset et al. *Metab. Eng.* 2(2):104-114, 2000; Winther-Larsen et al. *Metab. Eng.* 2:92-103, 2000). Recently, this vector has been used for recombinant expression of a host-toxic single-chain antibody fragment (scFv), hGM-CSF and hIFN-2αb (Sletta et al., *App. Env. Microbiol.* 70(12):7033-7039, 2004; Sletta et al, *Appl. Env. Microbiol.* 73(3):906-912, 2007).

The Pm promoter does not exhibit apparent sequence homology to the typical consensus promoter elements. The absence of a −35 element may be due to the requirement for XylS binding to promote transcription initiation. Further, the lack of a typical −10 consensus element could be explained by the fact that transcription initiation from Pm is mediated by two different σ-factors; $\sigma^{32}$ in the exponential phase and $\sigma^{38}$ in the stationary phase (Marques et al. *Mol. Microbiol.* 31(4):1105-1113, 1999).

Mutations made to Pm have previously been reported, both in the context of the study of promoter function and with the aim of improving expression systems based on Pm. Thus, for example Kessler et al. *J. Mol. Biol.* 230: 699-703, 1993 describes mutants of the Pm system which exhibit modified and in particular 'expression down' characteristics by virtue of point mutations and deletions in the XylS binding site of the Pm promoter, which may overlap with the −35 region of the promoter. As indicated above, the XylS binding site of Pm is known to confer activated XylS sensitivity to the Pm promoter, effectively 'switching' expression of the native or heterologous gene downstream of the Pm promoter and under the control of Pm, on and off. Hence, alterations in the control of inducibility or level of expression achievable from the promoter could be expected to be influenced by sequence alterations in the XylS binding region of the operon, as is borne out in Kessler et al., supra and indeed may be expected at any site in the −40 to −70 region as defined by Gonzales-Perez et al., (*J. Biol. Chem.* 274(4): 2286-2290, 1999), supra.

Further, as noted above, mutations in Pm in the region overlapping the region of −10 nucleotides upstream of the transcription start site and to which the RNA pol binds, may result in significant alterations to the level of expression achievable from the Pm promoter system relative to native Pm. Such alterations in expression may be in terms of both enhanced expression, so-called-'expression-up' mutants and reduced expression, so-called 'expression-down' mutants. Where enhanced expression is concerned, the expression level from such mutants could be approximately doubled by the introduction of mutations in the −10 region (Winther-Larsen et al, *Metab. Eng.* 2:92-103, 2000).

It is thus known in the art that Pm promoter mutations can affect gene expression, and maybe used to increase the level of gene expression attainable. Nonetheless, a need remains in the art to develop gene expression systems wherein expression can be enhanced to higher levels than that obtained with the Pm promoter mutants previously described, and particularly to maximise the level of expression attainable in any given gene expression system. It is well known that recombinant gene expression for a specific vector system varies among genes. Hence, a system which may be tailored to a particular gene would be very useful.

In co-pending unpublished application No. GB 0615556.8 filed on 4 Aug. 2006 (corresponding to PCT/GB2007/002951) we describe a method whereby expression of a desired gene may be enhanced by using a mutant mRNA leader. GB 0615556.8 particularly describes the use of mutant mRNA leaders which enhance transcription of a desired gene. This represents a novel concept in recombinant gene expression systems, since whilst the mRNA leader has previously been recognised to play a translational role, it had not heretofore been thought possible that mutating the leader might produce useful effects in enhancing transcription and hence expression in a recombinant gene expression system. As described in GB 0615556.8, mutations may be introduced into the leader, and a mutant leader may be selected to enhance expression of a particular gene. The effects of the leader mutants may be to some degree gene-dependent, and hence the use of such mutants allows the expression system to be tailored, or optimised for a particular gene, by selecting mutants which specifically enhance expression of that gene.

In work leading up to the present invention, the inventors have been able to improve further the Pm promoter mutants which may be obtained, particularly as regards the level of expression attainable. The −10 Pm mutants previously reported (WO 00/68375 and Winther-Larsen et al. *Metab. Eng.* 2:92-103, 2000) were limited by technical problems, which have now largely been eliminated. We have thus been able to develop methods for the generation and identification of high expression Pm mutants which may achieve up to a 10-fold increase in the level of gene expression. These represent an advance on the Pm mutants previously reported.

More surprisingly we have now found that by introducing one or more mutations into the Pm promoter and into the region encoding the mRNA leader sequence, expression of a gene can be enhanced to much higher levels than by using Pm promoter mutants alone, or indeed mRNA leader mutants alone. By combining Pm promoter and mRNA leader mutants in this manner, a surprisingly high level of expression may be achieved, greater than would have been thought possible from the effect of the Pm or leader mutants alone.

It is well known that in bacteria the efficiency of ribosome binding, necessary for translation, is primarily determined by the secondary structure of the mRNA in the translational initiation region (the mRNA leader or 5'-untranslated region, UTR). Mutations which have been made to hairpin structures in this region have been shown to effect translation (de Smit and van Duin, *J. Mol. Biol.* 244: 144-150, 1994). Further, alterations to the Shine-Dalgarno sequence in the 5' untranslated region have also been suggested to affect translation (Kozak. *Gene,* 234:187-208, 1999).

In Komarova et al. (*Journal of Bacteriology,* 187: 1344-1349, 2005), it was found that extending the Shine-Dalgarno sequence in the mRNA leader reduced translation, although this inhibitory effect could be counter-acted by introducing into the leader AU-rich sequences which serve as targets for ribosomal protein S1, upstream of the Shine-Dalgarno sequence. Coleman and Nakamura (*J. Mol. Biol.,* 181: 139-143, 1985) reported that mutations upstream of the ribosome binding site may affect translational efficiency. Mutations were made at or upstream of the Shine-Dalgarno sequence which varied the stability of mRNA by alteration of its secondary structure or removal of a portion of the Shine-Dalgarno sequence.

Whilst is known in the art that mutations which affect the secondary structure of the mRNA leader or the Shine-Dalgarno sequence may affect translation, it has not generally been reported in the art that it is recognised that the leader might be modified in order to enhance expression in the context of a protein production system, other than to modify an unfavourable Shine-Dalgarno sequence or undesirable secondary structures.

Particularly, it has not been considered previously that mutant leaders may be combined with promoter mutants. The inventors of the present invention have identified a method of producing extremely high levels of a gene product by combining Pm promoter and mRNA leader mutations. Even more surprisingly, the level of expression which may be attained is greater than any cumulative effect on expression of using a Pm promoter mutant and a mutant mRNA leader. Thus, by way of example, the level of expression of a β-lactamase reporter gene may increase by approximately 10 times using a mutant Pm promoter and 20 times using a mutant mRNA leader. However, by combining Pm and leader mutants approximately 60 and 90 times increments of expression may be achieved from a Pm/Pm leader mutated system, compared to that from the wildtype expression system (i.e. using an unmutated Pm promoter/leader system), as determined by realtime PCR experiments and enzyme activity studies respectively. Such a surprisingly high increase could not have been predicted.

Hence, the construction of DNA libraries containing a mutated Pm promoter and a mutated region encoding (or corresponding to) the 5' untranslated region (UTR) or mRNA leader has allowed the identification of mutants which strongly stimulate gene expression. Such combined Pm and leader mutants may enhance the expression of a number of genes although this may be to varying extents and the effects are largely believed to be independent of the combination of promoter and leader used. It is possible to identify specific combinations for optimal enhancement of a particular desired gene. This finding is of clear interest in the field of biotechnology and for the production of recombinant proteins, where the possibility of increasing production of such proteins by enhancing expression using such combined Pm and leader mutants is clearly of commercial or industrial interest.

The present invention is thus predicated on the novel and unexpected finding that using a combination of Pm promoter and mRNA leader mutants may particularly enhance gene expression. The high expression levels attainable using the combined mutants reduce the reliance on the increased gene copy number afforded by plasmids to achieve acceptable expression levels and thus advantageously permit the development of plasmid-free expression systems for recombinant protein production. The present invention permits the optimisation of expression level per gene copy. Thus, of further industrial interest is the very high levels of expression which may be achievable through chromosomal integration of one or a few copies of desired gene using the combined Pm promoter and leader mutants. This would potentially eliminate the need for plasmids in protein production (and the problems associated therewith) and provide a significant improvement in industrial protein production.

The invention is thus based on introducing one or more mutations into the Pm promoter and into the DNA corresponding to an mRNA leader (a UTR) and selecting a mutant Pm promoter and mRNA leader (UTR) combination which enhances expression of a desired gene (i.e. the gene it is desired to express). As will be explained further below, Pm and leader mutants may be separately generated and selected, and then combined, or a combined Pm/leader construct may be subjected to simultaneous mutagenesis or a Pm mutant may be separately generated and identified and then used as the basis of a construct for generating leader mutants in the context of the Pm mutant, or vice versa. The step (s) of introducing the mutations may thus be seen as generating a library of combined Pm promoter and mRNA leader mutants which are then screened to select a mutant (e.g. one or more mutants) which enhances expression of the desired gene. As explained further below, the mRNA leader which is subject to mutation (in combination with the Pm promoter) can be selected according to choice, and need not be the leader which is particular or native to the desired gene or the Pm promoter.

In one aspect, the present invention accordingly provides, a method of producing a desired gene product in a recombinant gene expression system, said method comprising expressing said gene using a mutant Pm promoter which comprises one or more mutations which enhance gene expression and a mutant mRNA leader which comprises one or more mutations which enhance expression of said gene.

Alternatively viewed, the invention provides a method of enhancing expression of a desired gene product in a recombinant gene expression system, said method comprising expressing said gene using a mutant Pm promoter which comprises one or more mutations which enhance gene expression and a mutant mRNA leader which comprises one or more mutations which enhance expression of said gene.

Said mutant mRNA leader may be obtained by introducing one or more mutations into the DNA region (sequence) corresponding to the mRNA leader and selecting a mutant which enhances expression of the desired gene.

Thus, the desired gene may be expressed from a gene expression system comprising a mutant Pm promoter and a DNA region corresponding to a mutant mRNA leader, i.e. a DNA region corresponding to an mRNA leader which has been modified to contain one or more mutations, which enhance expression of said gene.

In a further aspect, the present invention also provides an isolated DNA molecule comprising (i) a mutant Pm promoter which comprises one or more mutations which enhance gene expression, and (ii) a region corresponding to an mRNA leader sequence, said region comprising one or more mutations which enhance expression of a desired gene.

Alternatively viewed, this aspect of the invention may be seen to provide an isolated DNA molecule comprising a Pm promoter and a region corresponding to an mRNA leader, wherein said Pm promoter and said mRNA leader region each comprise one or more mutations capable of enhancing expression of a desired gene.

In addition to the unexpected particular expression-enhancing effects of the mutant Pm/mutant mRNA leader combination, it has further been found that mutations in the regulatory protein XylS may also enhance gene expression and that enhancements of gene expression may be obtained by combining expression-enhancing XylS mutants with mutants of Pm and/or the mRNA leader. Whilst it is one preferred embodiment of the present invention further to combine a mutant XylS with the Pm/leader combination mutants earlier described (i.e. to create a "triple" mutant comprising mutations in Pm, mRNA leader, and XylS which enhance expression, namely a mutant being a combination of a mutant Pm, a mutant leader and a mutant XylS), it is proposed more generally herein that expression-enhancing combinations of any two or more of Pm, mRNA leader and XylS may be made and used to enhance expression of a desired gene.

Viewed from a broader aspect, the present invention can thus be seen to provide a method of producing a desired gene product in a recombinant gene expression system, said method comprising expressing said gene from a Pm promoter-based expression system using at least two mutant elements selected from:
(i) a mutant Pm promoter;
(ii) a mutant mRNA leader; and
(iii) a mutant XylS;
wherein said mutant elements each comprise one or more mutations which enhance expression of said desired gene.

It may be that each said element, when examined separately, has mutations which enhance gene expression. However, the present invention encompasses the situation that enhancement of gene expression is seen with (or in the context of) the combined mutants i.e. that enhanced gene expression is achieved when using the combination of two or more mutant elements together, in other words with the combination mutant.

Thus, in the recombinant gene expression system of the broader aspect of the invention, the desired gene may be expressed using a combination mutant (or a mutant combination) comprising at least two mutant elements selected from:
(i) a mutant Pm promoter;
(ii) a mutant mRNA leader; and
(iii) a mutant XylS;
wherein said combination comprises mutations which enhance expression of the desired gene.

This broader aspect of the present invention thus provides mutant combinations, which may be double or triple mutants, which may be used to enhance gene expression. The mutant combinations of the present invention may thus include, in addition to the Pm/leader double mutant discussed above, mutant Pm/mutant XylS, mutant XylS/mutant leader and mutant Pm/leader/XylS combinations. Such combination mutants may be used to enhance expression of a desired gene product.

Said mutant XylS may be obtained by introducing one or more mutations into the DNA sequence (DNA molecule) encoding XylS, namely into the xylS gene or xylS coding sequence. References herein to "mutant XylS" thus include mutants of the xylS gene or coding sequence.

A further broader aspect of the present invention provides an isolated DNA molecule comprising at least two mutant elements selected from:
(i) a mutant Pm promoter;
(ii) a DNA region (in other words a DNA sequence) corresponding to a mutant mRNA leader (or alternatively put a mutant DNA region corresponding to an mRNA leader leader); and
(iii) a mutant XylS-encoding DNA sequence (in other words a mutant xylS or a DNA sequence encoding a mutant XylS);
wherein said mutant elements each comprise one or more mutations which enhance expression of said desired gene.

In particular, said DNA molecule is functional in enhancing expression of a desired gene.

Thus, alternatively put, the isolated DNA molecule of this aspect of the invention may comprise at least two mutant elements selected from:
(i) a mutant Pm promoter;
(ii) a DNA region (in other words a DNA sequence) corresponding to a mutant mRNA leader (or alternatively put a mutant DNA region corresponding to an mRNA leader leader); and
(iii) a mutant XylS-encoding DNA sequence (in other words a mutant xylS or a DNA sequence encoding a mutant XylS);
wherein said DNA molecule is able to enhance the expression of a desired gene.

The broader aspects of the present invention are thus based on introducing one or more mutations into at least two of the Pm promoter, the DNA corresponding to an mRNA leader (a UTR) and the XylS gene and selecting a combination of at least two of a mutant Pm promoter, mutant mRNA leader (UTR) and mutant xylS gene which enhances expression of a desired gene (i.e. the gene it is desired to express). As will be explained further below, Pm, leader and XylS mutants may be separately generated and selected, and then combined, or a combined construct comprising at least two of Pm/leader/xylS may be subject to simultaneous mutagenesis, or Pm mutant may be separately generated and identified and then used as the basis of a construct for generating leader and/or XylS mutants in the context of the Pm mutant, or vice versa. In other words, any one element of the three may be selected and initially mutated and a mutant element thus obtained may be used as the basis for generating mutants of one or both of the other two elements, either simultaneously or sequentially. The step(s) of introducing the mutations may thus be seen as generating a library of combined Pm promoter and/or mRNA leader and/or XylS mutants which are then screened to select a mutant (e.g. one or more mutants) which enhances expression of the desired gene. As explained above, the mRNA leader which is subject to mutation (in combination with the Pm promoter and/or XylS) can be selected according to choice, and need not be the leader which is particular or native to the desired gene or the Pm promoter.

As is well understood in the art, "recombinant gene expression" refers to the expression of a cloned or "recombinant" gene (i.e. a gene formed by in vitro combination of two or more non-homologous DNA molecules) in a host cell which may be a prokaryotic or eukaryotic host cell. A system for such recombinant gene expression may thus include an expression vector into which the gene for expression (e.g. the cloned or recombinant gene) may be introduced, together with expression control sequences (e.g. promoter etc) necessary for expression of said gene. Such an expression vector containing the gene to be expressed is then introduced into a host organism (generally a host cell such as a bacterium) and the organism is then grown or cultured under conditions which allow the said gene to be expressed.

As referred to herein, "enhanced (gene) expression" means a level of gene expression which is increased as compared to, or relative to, the level of gene expression without the mutated elements (i.e. the mutated combination of two or more of Pm/leader/XylS) and more particularly as compared to, or relative to, the Pm promoter and/or leader and/or XylS combination before the mutations are introduced, i.e. in the absence of the (introduced) mutations. Thus, for example, for a combination of any two of the elements, the level of expression may be increased over the level of expression seen with a combination of the two elements before they are mutated (i.e. the "unmutated" elements). For a combination of all three elements (triple mutants), the level of expression may be increased relative to the corresponding unmutated Pm/leader/XylS combination. In the context of the specific embodiment of combined Pm and leader mutants, "enhanced (gene) expression" means a level of gene expression which is increased as compared to, or relative to, the level of gene expression without the mutated Pm and the mutated leader, and more particularly as compared to, or relative to the Pm promoter and/or mRNA leader before the mutations are introduced, i.e. in the absence of the (introduced) mutations.

In any mutant combination of the invention, such a leader may be a native leader, or any mRNA leader into which the mutations are introduced. For present purposes an "unmutated" mRNA leader, i.e. the leader, which is used as the starting point for the mutations introduced according to the present invention is referred to herein as the "wild-type" leader. Similarly, an "unmutated" Pm promoter which is used as the starting point for the mutations introduced is referred to herein as the "wild-type" Pm promoter. Such a wild-type Pm promoter may be the Pm promoter as it occurs in nature, i.e. the native Pm promoter.

An unmutated XylS (or xylS) which is used as the starting point for the mutations introduced according to the present invention may likewise be referred to as the "wild-type XylS". However, as for Pm and the mRNA leader, the term "unmutated" is used with reference to the expression-enhancing mutations of the present invention and hence means only that the expression-enhancing mutations have not yet been introduced (i.e. the element before introduction of the mutations). Thus, the XylS may be the XylS as it occurs in nature (i.e. the native XylS) or any other XylS or homologous protein that is functional in acting as a regulator of Pm; thus modifications of the native XylS may be included as the "unmutated" XylS etc.

Thus, in other words enhanced gene expression is gene expression which is increased when using a mutant combination according to the present invention (e.g. a mutant Pm promoter and/or a mutant leader, (or put more specifically a mutant DNA region corresponding to the mRNA leader)), as compared, or relative, to the corresponding wild-type or unmutated combination (e.g. unmutated Pm promoter and/or leader (or DNA region corresponding thereto)). Thus, the expression attainable with the mutant combination (e.g. mutant Pm promoter and the mutant leader combination) according to the present invention may be compared with the expression obtained using the corresponding unmutated or "wild-type" combination (e.g. unmutated or "wild-type" Pm promoter and leader). Hence, a "wild type" or "unmutated" expression system uses the same or corresponding gene, and combination (i.e. Pm promoter and/or mRNA leader (more specifically DNA region corresponding to the mRNA leader) and/or XylS) as the system of the present invention (where enhanced expression is seen), prior to modification (mutation) i.e. two or more of the Pm promoter/mRNA leader/XylS are not modified or mutated to enhance expression. Further, the combined mutants of the present invention may show enhanced gene expression when compared to the expression obtained using only one (or in the case of a combined triple mutant, two) of the mutant elements alone, for example where the combined mutant is a mutant Pm/mutant leader double mutant, using a mutated Pm promoter alone (preferably having the same Pm mutant as used in the combined mutant) and a corresponding wild-type mRNA leader, or when compared to the expression obtained using a wild-type Pm promoter and a mutant leader.

Furthermore, as is clear from the above, enhanced expression may also be assessed for each "component" of the combined mutants alone, e.g. for a mutant Pm or mutant leader or mutant XylS alone, by comparing to the corresponding "wild type" promoter or leader or XylS. The Pm promoter, mRNA leader or XylS used in a "wild-type" or "unmutated" expression system prior to the mutation being introduced, are therefore the unmutated or wild-type Pm promoter, mRNA leader or XylS, i.e. the "starting" Pm promoter, leader or XylS, where no manipulations have been carried out to enhance expression. The wild-type Pm promoter, leader or XylS are the Pm promoter, leader or XylS before modification (before mutation) i.e. the promoter, leader or XylS into which the mutations are introduced. They may be seen as the "source" or "origin" or "starting" Pm promoter, leader or XylS, or the Pm promoter, leader or XylS which are the substrates or targets for the mutations (more particularly, references herein to the leader include, or refer to, the DNA corresponding to the mRNA leader and references to XylS include, or refer to the DNA encoding the XylS e.g. xylS).

Particularly, the wild-type Pm promoter may have the sequence of SEQ ID No. 38:

5'-GATAGGGATAAGTCCAGCCTTGCAAGAAGCGGATACAGGAGTGCA

AAAAATGGCTATCTCTAGAAAGGCCTACCCCTTAGGCTTTATGCAA-3'

(Ramos et al, *Annu. Rev. Microbiol.* 51: 341-373, 1997).

The wild-type or unmutated Pm promoter may also contain modifications over the native form of SEQ ID No. 38, i.e., may be a derivative or variant of SEQ ID No. 38 but which does not contain the gene expression enhancing mutations of the present invention. As noted above, the "unmutated" leader which is subject to mutation according to the present invention may be a native leader (i.e. a leader as it occurs in nature) or it may be a synthetic or artificial leader or a native leader which is modified. Thus, the "unmutated" or "wild-type" starting leader need not be a naturally occurring leader, but may itself be a leader which has been modified or mutated over the native form, i.e. is a derivative or variant of a naturally occurring leader (e.g. a sequence modified derivative or variant) but which does not contain the mutations according to the present invention. In particular, any modification or mutation which the "unmutated" ("wild-type") leader may contain relative to the native leader as it occurs in nature does not affect expression.

The unmutated XylS/xylS may have the amino acid or DNA sequence of the native XylS/xylS as deposited at the National Center for Biotechnology Information (NCBI) with the accession no. AAB59163.

Thus the unmutated XylS may have the amino acid sequence of SEQ ID No. 39:

MDFCLLNEKSQIFVHAEPYAVSDYVNQYVGTHSIRLPKGGRPAGRLHHRI

FGCLDLCRISYGGSVRVISPGLETCYHLQIILKGHCLWRGHGQEHYFAPG

ELLLLNPDDQADLTYSEDCEKFIVKLPSVVLDRACSDNNWHKPREGIRFA

ARHNLQQLDGFINLLGLVCDEAEHTKSMPRVQEHYAGIIASKLLEMLGSN

VSREIFSKGNPSFERVVQFIEENLKRNISLERLAELAMMSPRSLYNLFEK

HAGTTPKNYIRNRKLESIRACLNDPSANVRSITEIALDYGFLHLGRFAEN

YRSAFGELPSDTLRQCKKEVA

The unmutated xylS may have the DNA sequence of SEQ ID No. 40:

5'-ATGGATTTTTGCTTATTGAACGAGAAAAGTCAGATCTTCGTCCACGC

CGAGCCCTATGCAGTCTCCGATTATGTTAACCAGTATGTCGGTACGCACT

CTATTCGCCTGCCCAAGGGCGGGCGCCCGGCAGGCAGGCTGCACCACAGA

ATCTTCGGATGCCTCGACCTGTGTCGAATCAGCTACGGCGGTAGCGTGAG

-continued

```
GGTAATCTCGCCTGGATTAGAGACCTGTTATCATCTGCAAATAATACTCA

AAGGCCATTGCCTGTGGCGTGGCCATGGCCAGGAGCACTATTTTGCGCCG

GGCGAACTATTGCTGCTCAATCCGGATGACCAAGCCGACCTGACCTATTC

AGAAGATTGCGAGAAATTTATCGTTAAATTGCCCTCAGTGGTCCTTGATC

GGGCATGCAGTGACAACAATTGGCACAAGCCGAGGGAGGGTATCCGTTTC

GCCGCGCGACACAATCTCCAGCAACTCGATGGCTTTATCAATCTACTCGG

GTTAGTTTGTGACGAAGCGGAACATACAAAGTCGATGCCTCGGGTCCAAG

AGCACTATGCGGGATCATCGCTTCCAAGCTGCTCGAAATGCTGGGCAGC

AATGTCAGCCGTGAAATTTTCAGCAAAGGTAACCCGTCTTTCGAGCGAGT

CGTTCAATTCATTGAGGAGAATCTCAAACGGAATATCAGCCTTGAGCGGT

TAGCGGAGCTGGCGATGATGAGTCCACGCTCGCTCTACAATTTGTTCGAG

AAGCATGCCGGCACCACGCCGAAGAACTACATCCGCAACCGCAAGCTCGA

AAGCATCCGCGCCTGCTTGAACGATCCCAGTGCCAATGTGCGTAGTATAA

CTGAGATAGCCCTAGACTACGGCTTCTTACATTTGGGACGCTTCGCTGAA

AACTATAGGAGCGCGTTCGGCGAGTTGCCTTCCGACACCCTGCGTCAATG

CAAAAAGGAAGTGGCTTGA-3'
```

The unmutated XylS/xylS may contain modifications (sequence variations) over the native forms of SEQ ID Nos. 39 or 40, i.e. may be a derivative or variant of SEQ ID Nos. 39 or 40 but which does not contain the expression-enhancing mutations of the present invention. Thus, the unmutated or "wild-type" starting XylS need not be the naturally occurring XylS but may be a XylS which has been modified over the native form. In particular, any modification or mutation which the "unmutated" XylS may contain relative to the native XylS does not affect expression, particularly expression of the desired gene.

According to the invention, gene expression may be enhanced by enhancing transcription and/or translation. Insofar as the promoter mutations are concerned it will be understood of course, that transcription will be enhanced. Mutations in XylS may be expected to enhance transcription via the Pm promoter. Insofar as the leader is concerned enhancement of gene expression may be achieved by enhancing transcription and/or translation. It is however preferred that the mutant leader be capable of enhancing transcription of the desired gene. Certain mutant leaders may have both transcriptional and translational effects. Thus, there may be an enhancement of both gene transcription and translation. More specifically, one or more of the mutations introduced may cause or result in enhanced translation as well as, or independently of enhanced transcription.

An enhancement of translation can either occur as a direct result of an enhancement of transcription or can be independent of transcription. Hence, an enhancement of translation which is independent of transcription could result from, for example, more efficient ribosome binding and the actual process of translation, rather than as a result of more transcripts being present due to enhanced transcription. Such an enhancement of translation which is independent of transcription could be due to an alteration of the secondary structure of the mRNA leader sequence as reported in the art. An enhancement of translation which is a result of enhanced transcription may be due to, for example, the increased number of transcripts being available for translation or an increase in transcript stability.

High levels of enhancement of expression may be achieved using the combination mutants of the present invention. Expression of the gene product can be enhanced by up to, for example, 60 fold or more when using the combined Pm promoter/mRNA leader mutants of the invention compared to a wild type Pm promoter/leader, but it will be appreciated that this may vary significantly, depending upon the precise system used, and what the starting point is. For example starting from a system using a Pm promoter and a leader where only low levels of expression are obtained, a much higher enhancement in the amount of protein product obtained may be achievable. Thus, an increase of expression (for example determined by the amount of protein produced) of 60- 70-, 80- or 90-fold or more may be attainable. In other systems (e.g. in different expression vectors or using different control sequences) or under other conditions the increase may be less.

In the case of XylS mutants for example, experiments have shown that an additive or possibly greater than additive effect may be obtained when combining XylS with either Pm mutants or leader mutants.

Whilst such increases in expression as mentioned above are desirable and may be attained with a variety of genes, it will be appreciated that they may not always be possible to achieve in the context of a particular gene or coding sequence. Thus such high increases in the level of protein product may not always be seen (despite in some cases an increase in transcription being seen). It is known in the art that the nature of the coding sequence itself may limit the expression attainable (in terms of levels of translated protein product attainable). Thus, translation may be limited by the codon usage in the nucleic acid molecule to be expressed. More specifically, the amount of specific tRNA which is available for a particular codon may limit translation and different host cells may be limited in the specific tRNAs they contain, or the amounts thereof. A coding sequence or gene which has codons unfavourable in a particular host cell will therefore be expressed into gene product at a reduced level in that host. The improvements attainable by the mutants and methods of the present invention may therefore be constrained by the codon usage of the nucleic acid molecule (ie. gene or coding sequence etc) to be expressed. Procedures for overcoming codon-usage issues are known in the art, and include for example expressing particular tRNAs in the host cell or modifying the coding sequence to modify the codons used. It may also be the case, however, that other factors to do with the coding sequence may limit the level of protein expression which may be achieved. Nonetheless, this does not take away from the fact that the mutants and methods of the present invention may result in beneficial enhancements in expression (including at the protein level) for a number of different proteins and in different expression systems.

With this in mind, generally speaking, a level of enhancement of at least 4 or 5-fold (5 times more expression), preferably at least 6, 7, 8, 9, 10, 15, 20, 25, 30, 40, 50, or 60 fold, may be seen using the combined mutant (e.g. combined Pm/leader mutants), as compared with a corresponding wild type combination) (e.g. wild-type Pm/leader combination) (for example as determined by levels of protein product obtained, or activity of the expressed protein). In an optimal system, a level of enhancement of at least 25-fold or more may be seen. Put another way, when comparing the combined mutants against the corresponding single mutants an increase in expression of at least 1.1, 1.2, 1.3, 1.4, 1.5, 1.6, 1.7, 1.8, 1.9 and 2 times (2-fold) preferably at least 3 times, may be seen as compared to the corresponding single mutant used alone. For example, in the case of the Pm/leader mutants such increases may be seen as compared to the corresponding leader mutant when used alone (i.e. with a wildtype Pm promoter) and an increase in expression of at least 1.1, 1.2, 1.3, 1.4, 1.5, 1.6, 1.7, 1.8, 1.9, 2 and 3 times, preferably 4, 5 or 6 times (fold) as compared to the corresponding promoter mutant when used alone (i.e. with a corresponding wild-type leader). The level of enhancement may be determined using Real-time PCR to determine transcript production or by measuring protein levels or activity.

In light of the above comments, it will be appreciated that if a gene product is encoded by a sequence with unfavourable codon usage, then the level of enhancement may be reduced. In such circumstances, the level of enhancement may be less e.g. 1.5, 2, 2.5, 3, 3.5 or 4-fold, or less. If the coding sequence were altered or the level of necessary tRNA(s) is increased, then the level of enhancement may approach the values given above.

In the case of a mutant Pm promoter, desirably this may enhance transcription (or expression of a gene product i.e. protein expression) at least 2-fold or 5-fold, and preferably at least 6, 8 or 10-fold over a wild-type Pm promoter (for example when mutant and wild-type promoters are assessed in the context of the same leader e.g. a wild-type or mutant leader or the same XylS e.g. a wild-type or mutant XylS).

In the case of a mutant leader, desirably this may enhance transcription (or expression of a gene product i.e. protein expression) by at least 5-fold, more particularly at least 8, 10, 12, 15, 18 or 20-fold, as compared with a wild-type leader (for example when both are assessed in the context of the same promoter e.g. a wild-type or mutant Pm promoter).

For example, it may be convenient to assess the mutant leader in the context of a mutant promoter. Accordingly a combined Pm/leader mutant may enhance expression at least 1.1, 1.2, 1.3, 1.4, 1.5, 1.6, 1.7, 1.8, 1.9, 2, 3, 4 or 5-fold; or more particularly at least 10 or 15-fold as compared to a mutant Pm/wild-type leader combination, for example by or by at least 5-30, 7-30, 7-25, 5-25, 5-20 fold.

Alternatively, a combined Pm/leader mutant may enhance expression at least 2, 3 or 5-fold, or more particularly at least 10-fold as compared to a wild-type Pm/mutant leader combination In the case of a mutant XylS, this may enhance expression at least 1.5 fold, or at least 2-fold or 5-fold, and preferably at least 6, 8 or 10-fold over a wild-type XylS, for example when mutant and wild-type XylS are assessed in the context of the same Pm promoter or leader e.g. a wild-type or mutant promoter or leader.

By way of example only, expression of the gene, preferably determined by transcript production or protein activity or level, may be enhanced by at least 90, 85, 80, 75, 70, 65, 60, 50, 40, 30, 25, 20, 15, 10 or 5-fold in a system using a mutant combination (e.g. a mutant Pm promoter and a mutant mRNA leader) compared to expression using the corresponding unmutated combination (e.g. unmutated or wild-type Pm promoter and mRNA leader). Alternatively viewed, the minimum level of enhancement which can be seen may be 5-fold, wherein expression can be enhanced by at least 5, 10, 15, 20, 25, 26, 27, 28, 30, 35, 40, 45 or 50-fold.

The level of enhanced expression of the gene product can be measured by any convenient method known in the art. For example, expression can be determined by measuring protein activity (i.e. the activity of the expressed protein) wherein the levels of protein activity obtained using the mutant combination (e.g. Pm promoter and mutant mRNA leader) as opposed to the wild type combination (e.g. wild-type Pm promoter and mRNA leader) are increased or enhanced. Alternatively, the amount of protein produced can be measured to determine the level of enhanced expression, for example by Western blotting or other antibody detection systems, or indeed by any method of assessing or quantifying protein. Many such methods are known in the art.

Enhanced expression may also be determined at the transcript level, for example by assessing transcript levels using real time-PCR.

In order to identify the combination mutants (e.g. Pm promoter and mRNA leader combination mutants) which stimulate or enhance expression, the desired protein product can be expressed with a tag or as a fusion protein e.g. a his-tag or other suitable detection means, which can allow the measurement of gene expression using one assay for all different protein products. Particularly preferred as a method of identifying expression-enhanced mutants is to express the protein from an operon system, where the desired gene is translationally coupled to a reporter gene. Particularly, a reporter gene is selected whose expression level correlates with the expression level of the desired gene. The levels of expression of the desired gene can therefore be assessed or an indirect indication of its expression level may be obtained by measuring the level of the reporter gene which has been used. Reporter gene expression can be determined by the activity of the reporter gene. For example, if GFP was used, levels of fluorescence obtained would correlate to the level of gene expression of the desired gene product. Attractive reporters to use are those whose activity or presence it is possible to quantify or assess (e.g. semi-quantitatively) efficiently or readily, particularly those which result in growth or growth inhibition or cell death, as such reporters can be readily assessed by determining cell (e.g. colony) growth or non-growth. Antibiotic resistance markers fall into this category, e.g. bla encoding β-lactamase. Bla is particularly attractive as resistance correlates well to expression level. Reporters based on activity of the gene product may also be used e.g. reporter genes encoding an enzyme which may produce or be involved in the production of a detectable product or in a detectable reaction. An example of such a reporter is the luc gene encoding luciferase. Such "activity-based" reporters however require individual clones to be assayed. Particularly preferred reporter genes which can be translationally coupled to the gene expressing the desired gene product are beta-lactamase (bla) and firefly luciferase (luc).

An indication of enhanced gene expression may also be given by an enhancement of transcription, which as indicated previously may result from an increase in the production of transcripts (or alternatively viewed an increase in the level of transcription) or from increased transcript stability or both. Since the enhancement of gene expression can be due to enhanced transcription and/or translation, transcription may be enhanced by 5, 10, 15, 20, 30, 40, 50 or 60 fold or more when using a mutant combination (e.g. the mutant Pm and leader combination) compared to using the wild-type combination (e.g. wild-type Pm promoter and leader). Transcription may desirably be enhanced by 90, 85, 80, 75, 70, 65, 60, 50, 40, 30, 20, 10 or 5 fold in a system using a mutant combination (e.g. a mutant Pm promoter and a mutant mRNA leader). Alternatively viewed, in a preferred embodiment the minimum increase in transcription may be 5-fold, where transcription may be enhanced by at least 6, 7, 8, 9, 10, 11, 12 or 13 fold. The transcript level can be determined using any convenient method known in the art, for example by Northern blotting, or array technology or real-time PCR. To assess transcript stability, mRNA decay may be measured.

Enhanced gene expression can also be caused by enhanced translation which refers to an increase in the amount of protein product obtained using a mutant combination (e.g. mutant Pm promoter and mutant mRNA leader) as compared to or relative to the level of translation in the absence of the mutant combination (e.g. mutant Pm promoter and mRNA leader) (e.g. wild type Pm/leader). As mentioned previously, enhanced translation can be due to an enhancement of transcription which results in an increased level of transcripts being available for translation and/or can be independent of transcription and be due to for example enhanced ribosome binding. Desirably, according to a preferred embodiment of the present invention, translation may be enhanced by 5, 10, 15, 20, 30, 40, 50 or 60 fold or more when using the mutant combination (e.g. Pm and leader combination) compared to using the wild-type combination (e.g. wild-type Pm promoter and leader). Translation may be enhanced by 90, 85, 80, 75, 70, 65, 60, 50, 40, 30, 20, or 5 fold in a system using a mutant combination (e.g. a mutant Pm promoter and a mutant mRNA leader). Alternatively viewed, in a preferred embodiment the minimum increase in translation may be 5 fold, where translation may be enhanced by at least 6, 7, 8, 9, 10, 11, 12 or 13 fold. Enhanced translation may be measured by the same methods as described above for enhanced gene expression.

As used herein, the term "mRNA leader" or mRNA leader sequence is equivalent to the term "5' untranslated region" or "UTR" and refers to the transcribed mRNA sequence between the transcription start site and translation start site in mRNA. The mRNA leader sequence hence is the transcribed sequence which begins at position +1 which relates to the transcription start site and continues until the translation start site. The region corresponding to the mRNA leader (sequence) occurs at the DNA level rather than the RNA level and may therefore also be viewed as the DNA (e.g. DNA sequence or region) which encodes the leader. The region corresponding to the mRNA leader may thus also be seen as the DNA which is the complement of the mRNA leader or which templates its synthesis. This is also known as the initial transcribed sequence (ITS) at the DNA level. Mutation of the region encoding the mRNA leader sequence can alter the transcription start site. For example a deletion of two, three, four or five base pairs in the DNA which encodes the leader may alter the transcription start site by an equivalent number of base pairs—in such a situation, +1 will relate to the 'new' transcription start site and hence the mRNA leader sequence in this case will again be defined as the sequence between +1 which relates to the transcription start site and the translation start site in mRNA. Hence a deletion mutation in the DNA encoding the leader may be expected to alter the transcription start site by a corresponding number of base pairs.

The initial transcribed sequence (ITS) occurs at the DNA level as noted above and corresponds to or encodes the transcribed mRNA leader sequence. Hence, reference herein to introducing one or more mutations into the mRNA leader, refers to the mutation of the corresponding DNA sequence, i.e. the ITS sequence. Mutation of this region produces corresponding mutations in the mRNA leader sequence which is the transcribed ITS.

The mRNA leader sequence or its corresponding ITS can typically be from 10 to 40 bases long, although it may be longer (e.g. up to 50, 60, 70, 80 or 100 or more bases). For example, the mRNA leader or ITS may be 30 bases long, or 25, 26, 27, 28 or 29 bases long, but this will of course depend on the gene or promoter from which the mRNA leader is obtained or derived. Any region encoding an mRNA leader sequence can be used in combination with any gene to be expressed and the mutant Pm promoter.

According to the present invention, the mRNA leader need not be derived from the native leader of the gene to be expressed, and nor need it be a Pm leader. Thus, any mRNA leader may be used, or put more particularly, any DNA region corresponding to an mRNA leader. Thus, the region corresponding to the mRNA leader may be from, or may be derived from, any gene or any gene system (e.g. operon etc). It may be, or may be derived from, the leader which is native to the gene to be expressed, or it may be heterologous to the gene. It may, for example be, or may be derived from, the leader (more precisely the leader-corresponding sequence) which occurs naturally with the Pm promoter which is used for expression i.e. which is native to the Pm promoter. It may alternatively be non-native (heterologous) to both the Pm promoter and the gene. As noted above, the mRNA leader may be used in its native form i.e. as it occurs in nature, or it may be modified or synthetic i.e. the "starting" ("unmutated") leader may be an mRNA leader which is modified over its native form. Accordingly, the Pm promoter and mRNA leader-corresponding sequences which are used and into which mutations are introduced may not be those found naturally with the desired gene. Alternatively viewed, one or more of the Pm promoter, region corresponding to the mRNA leader and gene may not occur naturally together. Hence, for example, the Pm promoter may be used with the Pm mRNA leader and a different desired gene i.e. the gene is heterologous, or alternatively, the mRNA leader and gene maybe "native" to each other and not the Pm promoter.

A preferred mRNA leader for use according to the present invention is or is based on that associated with the Pm promoter. Thus, the "Pm" leader is preferred to be used as the leader to be mutated according to the present invention and as used herein the term "Pm mRNA leader" includes not only the native Pm mRNA leader as it occurs in nature, but also derivatives or variants thereof, e.g. Pm mRNA leader sequences which have been modified over the native "original" sequence. The original Pm mRNA leader is described in Inoye et al (*Gene*, 29: 323-330, 1984). Pm mRNA leader derivatives or modified Pm mRNA leader sequences are described in Winther-Larsen et al (*Metab. Eng.* 2: 92-103, 2000).

Other representative mRNA leaders include the lac leader or derivatives thereof. The leaders from the promoters PT7φ10 and Ptrc and derivatives thereof can also be used.

Alternatively, the mRNA leader used is native to the desired gene or is derived from such a native leader.

Mutations can be made to the region which corresponds to the mRNA leader (i.e. to the ITS) at any one or more positions from the transcription start site to the translation start site. A mutation can consist of an addition or deletion or substitution of any one or more nucleotides in the ITS which results in the addition or deletion or substitution of any one or more nucleotides in the mRNA leader. Addition or deletion mutations may involve the addition or deletion of one or more base pairs. Hence, 1, 2, 3, 4, 5, 6 or 7 or more bases can be inserted or deleted. In a particularly preferred embodiment, however, a mutation may be a substitution, which can occur at any position and may involve repetition (e.g. duplication) or inversion of fragments or segments of sequence. Hence, any of A, T(U), C or G can be substituted with a different base selected from A, T(U), C or G.

One or more mutations may be introduced to the ITS or mRNA leader. The one or mutations may be a combination of substitution, addition and/or deletion mutations or a number e.g. 2 or more additions or substitutions or deletions. Hence, a leader or ITS can contain for example both substitution and deletion mutations. Further, a leader or ITS may contain more than one substitution mutation at different positions in the leader. The length of the leader may also be increased, for example by introducing insertions or adding bases to one or both ends of the encoding sequence.

The number of mutations made is preferably in the range of 1 to 6, e.g. 2, 3, 4 or 5. For example, a mRNA leader or ITS may comprise 1, 2, 3, 4 or 5 substitution mutations, or may comprise 1 substitution mutation and 1 or more (e.g. 2 or 3) deletion mutations. Alternatively, substitution and/or deletion mutations may be coupled with mutations which extend the length of the leader.

The one or more mutations can be introduced into the ITS from position +1 i.e. the transcription start site or further downstream of this position. In a preferred embodiment, mutations, particularly substitutions, are present downstream of the region immediately at the transcription start site or near to it, for example downstream of position +7. Hence, mutation(s), particularly substitutions, may be present at for example from +8 to +30, more particularly at any one or more of positions +8, +9, +10, +11, +12, +13, +14, +15, +16, +17, +18, +19, +20, +21, +22, +23, +24, +25, +26 and/or +27. In the case of a longer or extended leader, mutations may be introduced at downstream positions up to the length of the leader, i.e. at any one of positions +8 up to the translational start site (from +8 to the end of the ITS). As previously described, any mutation i.e. an addition, deletion or substitution can be made at any of these positions. Mutations can be introduced further downstream than position +20. For example at any one or more of residues +21, +22, +23, +24, +25, +26, +27, +28, +29 or +30 or further downstream, in the case of a longer leader. Thus, mutations can be introduced up to the translational start site at the end of the ITS. However, notwithstanding the preferred presence of mutations downstream of +7, mutations may also be present at or at positions close to or near the transcriptional start (+1), for example at positions +1 to +7, more particularly +1 to +6 or +1 to +5 eg. at positions +2 to +5. Such mutations at or close to the transcriptional start are preferably deletions (eg. deletions of one or more nucleotides, which may be contiguous or non-contiguous, for example 1 to 4 or 1 to 3 or 1 or 2 nucleotides). It is believed that such mutations may act by stimulating initiation of transcription. For strong enhancement of expression, mutations downstream of the transcriptional start region are believed to be important, particularly substitutions, but mutants of the invention may for example contain one or more mutations, preferably substitutions, at downstream positions, for example downstream of +5, +6 or +7, together with one or more mutations (preferably deletions) at the region immediately at or close to the transcriptional start (eg. at +1 to +5, +6 or +7).

Although any mRNA leader can be mutated in the present invention, in a preferred embodiment the invention uses the mRNA leader sequence which occurs naturally with the Pm promoter (a "Pm mRNA leader") which includes derivatives of the native sequence. Hence, according to the present invention, one or more mutations may be made to the sequence aactagtacaataataatggagtcatgaacatatg (SEQ ID No. 1) which is the DNA sequence (or ITS) corresponding to a Pm leader. A representative mutant Pm mRNA leader may have a sequence selected from SEQ ID NOs. 2-12 and 14-37 as shown in Table 6. However, it will be understood that these mutants were identified by screening using particular genes. As explained above, the effects of the mutations may in some cases and/or to some degree be gene-specific or gene-dependent. Accordingly, whilst it may be the case that some mutants may be useful with different genes, particular mutants are not generally regarded to be of universal application, and mutants will be selected for particular genes.

The Pm mRNA leaders can be mutated at any one of positions +1 to +35 and as described previously such mutations can be selected from any one or more of a substitution mutation, a deletion mutation and an addition mutation.

Mutations are hence preferably found within the range of position +2 to position +27, more preferably within the range from position +2 to +18, for example mutations maybe found at one or more of +2, +3, +5, +6, +8, +9, +10, +11, +12, +13, +14, +15, +16 and +17.

Representative mutated Pm ITS or mRNA leaders encompassed by the invention are those of SEQ ID NOs 2-12 and 14-37.

The Pm promoter sequence can be found upstream of the transcription start site and is generally viewed as covering positions for example from −70 to −1, although this may vary. The Pm promoter sequence hence does not include any of the transcribed sequence or the sequence at the DNA level which will be transcribed. The Pm promoter sequence does not therefore cover any of the sequence downstream of and including +1. If mutation of the Pm promoter affects the transcriptional start site, then the promoter will still be considered as consisting of the sequence up to −1. Hence, it is possible for the Pm promoter once mutated to comprise part of the original DNA encoding the mRNA leader, if the transcriptional start site has moved.

The mutated Pm promoter of the invention may therefore contain one or more mutations at any position in its sequence. Particularly one or more mutations may be introduced at any position from −1 to −70, for example from −30- to −70 or −40 to −70 or −50 to −60.

Preferably, however, the Pm promoter is modified in the −10 region, which is understood to cover the region spanning the nucleotide sequence from −1 to −25 (more particularly −1 to −24 or −1 to −23) nucleotides upstream of the transcriptional start site and is the area of the double helix to which the RNA polymerase becomes chiefly associated upon DNA binding prior to the initiation of transcription. The −10 region is recognised by the RNA polymerase on the basis of its nucleotide sequence dependent 3-dimensional conformation which is exposed to the RNA polymerase when the DNA helix is twisted by torsion-induced influences further upstream of the −10 region. Such torsion-induced changes and recognition of the −10 region are generally the result of the binding of the activated inducer, e.g. XylS, upstream of the −10 region.

Hence, modifications may be introduced at any one or more of positions −1 to −25, for example, at −2, −3, −4, −5, −6, −7, −8, −9, −10, −11, −12, −13, −14, −15, −16, −17, −18, −19, −20, −21, −22, −23, −24 or −25.

Mutations may also be made in the region between the "−10 region" and the "−35 region", for example in the region of −23 to −35. The XylS binding site begins at around −35 and extends further upstream of the Pm promoter and mutations may also be made to this region.

A mutation can consist of an addition or deletion or substitution of any one or more nucleotides in the Pm promoter. Addition or deletion mutations may involve the addition or deletion of one or more base pairs. Hence 1, 2, 3, 4, 5, 6 or 7 or more bases can be inserted or deleted. In a particularly preferred embodiment, however, a mutation may be a substitution, which can occur at any position and may involve repetition (e.g. duplication) or inversion of fragments or segments of a sequence. Hence, any of A, T, C or G can be substituted with a different base selected from A, T, C or G.

One or more mutations may be introduced into the Pm promoter. The one or more mutations may be a combination of substitution, addition and/or deletion mutations or a number e.g. 2 or more additions or substitutions or deletions. Hence a mutated Pm promoter can contain for example both deletion and substitution mutations. Further, the Pm promoter may contain more than one substitution mutation at different positions. The length of the promoter may also be increased, for example by introducing insertions or adding bases to one or both ends of the encoding sequence.

Mutations may be present in the region of the promoter close to the transcriptional start site eg. at positions −1 to −6 or more particularly −1 to −5 or −1 to −4. Such mutations, which are preferably deletions, may be of one or more nucleotides eg. 1 to 5, 1 to 4, 1 to 3 or 1 or 2 nucleotides, which may be contiguous or non-contiguous. Such mutations close to the transcriptional start, particularly deletion mutations, are believed to stimulate initiation of transcription As noted above, the wild-type Pm promoter does not have a typical −10 consensus sequence. Based on a comparison of 20 σs dependent *E. coli* promoters, Lacour and Landini (*J. Bacteriol.* 186:7186-7195, 2004) have proposed the −10 promoter element consensus sequence TG(N)0-2CYATNCT (SEQ ID NO. 41). Mutant promoters of the invention may comprise mutations which introduce or approximate such a consensus sequence.

The TANNCT (SEQ ID NO. 42) motif of the Pm promoter may be conserved.

Gaal et al. (*Mol. Microbiol.* 42:939-954, 2001) have identified an optimised −10 promoter element for expression mediated by σs; TGTGCTATAC/AT (SEQ ID NO. 43). Mutant promoters according to the present invention may comprise mutations which introduce or approximate such a sequence.

Mutant promoters of the invention may also comprise mutations upstream of the region corresponding to the −10 consensus or optimised region. These may be additional to mutations in the region corresponding to the −10 consensus or optimised region. Thus, such mutations may lie at positions at or close to −15 e.g. at positions −15- to −25 or −15 to −23.

The number of mutations made in the Pm promoter is preferably in the range of 1 to 8 or 2 to 6 e.g. 4, 5 or 6. For example Pm mutants may have 1 deletion mutation and 4 or 5 substitution mutations in the −10 region. FIGS. 3 and 6A show preferred mutations in the −10 region of Pm. In one specific embodiment of the invention, Pm promoter mutants: Pm-7b-4g and Pm-7B-2g of FIG. 6A are encompassed. In a further preferred embodiment of the invention, the nucleic acid molecule comprises the Pm mutant 7b4g and the Pm UTR mutated sequence shown in FIG. 6B.

XylS is a protein of 321 amino acids (1-321) encoded by a gene xylS of 966 bases (1-960). Mutations may be introduced at any one or more of these positions. A mutation can consist of an addition or deletion or substitution of any one or more nucleotides in the xylS DNA sequence or amino acids in the XylS protein. Addition or deletion mutations may involve the addition or deletion of one or more base pairs or amino acid residues. Hence 1, 2, 3, 4, 5, 6 or 7 or more bases or amino acids can be inserted or deleted. In a particularly preferred embodiment, however, a mutation may be a substitution, which can occur at any position and may involve repetition (e.g. duplication) or inversion of fragments or segments of a sequence. Hence, in the DNA sequence of xylS any of A, T, C or G can be substituted with a different base selected from A, T, C or G. In the case of the XylS protein, the amino acid may be substituted with any other amino acid, and this may or may not be a conservative substitution.

One or more mutations may be introduced into XylS/xylS. The one or more mutations may be a combination of substitution, addition and/or deletion mutations or a number e.g. 2 or more additions or substitutions or deletions. Hence a mutated XylS/xylS can contain for example both deletion and substitution mutations. Further, the XylS/xyS may contain more than one substitution mutation at different positions. The length of the XylS/xylS may also be increased, for example by introducing insertions or adding bases to one or both ends of the encoding sequence, as it may be decreased, e.g. by mid-sequence or terminal deletions e.g. truncation mutants.

The number of mutations may range from e.g. 1 to 6, e.g. 1, 2, 3, 4, 5 or 6 mutations, e.g. substitutions.

More particularly, the mutations may be made in the N-terminal domain of the XylS protein (or in the corresponding DNA sequence encoding the N-terminal domain). The N-terminal domain may be defined as amino acids 1-203. Thus, the mutations may for example comprise one or more substitutions (e.g. 1-6, 1-5 or 1-4 substitutions) in amino acids 1-203 of XylS. The mutations may for example 11e in the region 156-203, or 160-203. As noted above, the mutation(s) to XylS have the effect of enhancing gene expression, particularly expression of the desired gene.

Example 3 below shows various representative mutations (or mutated positions) in XylS, any one or more of which may be made to XylS according to the present invention in any combination e.g. 1 to 6 of any of the mutations (or mutated positions) shown. Furthermore, any of the specific XylS mutants shown (i.e. any one of the XylS mutants designated Syn or StEP) may be viewed as representative mutants according to the present invention.

As already described, the nucleic acid molecule of the invention therefore comprises at least two of a Pm promoter with one or more mutations, a region corresponding to the mRNA leader with one or more mutations, and a XylS-encoding sequence with one or more mutations. Hence, at least two of these regions must be mutated as described herein. The invention does not encompass nucleic acid molecules wherein only one of the Pm promoter, the region encoding the mRNA leader and the XylS encoding sequence is mutated.

Any of the mutations in the Pm promoter and/or the region encoding the mRNA leader and/or XylS may be generated by any method known in the art. For example, mutations may be made by mutagenesis which may be site-directed or random.

Random mutagenesis may be induced by chemically crosslinking agents or by radiation, for example exposure to UV light or may involve chemical modification of the nucleotides encoding or constituting the Pm promoter, the mRNA leader and/or XylS. Alternatively, random mutagenesis may be achieved using synthetic oligonucleotides. For example, using or adapting the cassette mutagenesis procedure of Wells et al, (*Gene.* 34:315-323, 1985). Preferably mutations are introduced to two or more of the Pm promoter, to the ITS sequence which corresponds to the miRNA leader at the DNA level and the XylS-encoding sequence (xylS).

Advantageously, the Pm promoter, the ITS and/or xylS can be mutated by using a 'doped' nucleotide mixture during their synthesis, where at each step in polymerisation, the relevant wild type oligonucleotide is contaminated with the three other bases. This method enables the mutation frequency to be set at any particular level. Another alternative is using error-prone polymerase chain reaction (PCR) mutagenesis to introduce mutations in these elements. This allows mutations to be introduced at high frequency into any DNA sequence that is amplified in the PCR reaction, e.g. into the xylS coding sequence at frequencies set by the experimenter. Error prone PCR can be followed by DNA shuffling to further recombine the gene variation.

The mutations introduced into the Pm promoter and/or ITS or mRNA leader and/or XylS/xylS may be non-predetermined mutations, or random mutations. Hence, in this case the particular mutations which are introduced are not designed or specified before mutagenesis occurs. Thus, the mutations which occur may not be predicted or determined. Any random mutagenesis method known in the art can be applied to produce the non-predetermined mutations e.g. radiation or using a 'doped' nucleotide mixture during synthesis as mentioned above. The introduction of non-predetermined mutations preferably refers to the initial screening stage of identifying mutations which enhance gene expression. Hence random mutagenesis may be used when identifying an enhancing mutation. However, once such a mutation has been identified then it can be introduced into a Pm promoter or mRNA leader sequence or XylS by any mutagenesis method to provide the present invention.

The mutated Pm promoter, the mutated region encoding the mRNA leader and the mutated XylS may be mutated separately or together. The Pm promoter may be mutated in a first instance and its ability to enhance gene expression when used with a wild-type mRNA leader or wild-type XylS may be tested. Hence, mutated Pm promoters may be tested in a library and gene expression measured using for example a reporter gene or a desired gene product. Similarly, the mRNA leader may be mutated alone and its ability to enhance gene expression when used with a wild-type Pm promoter (or another promoter) may be tested e.g. again in a library. Likewise, the XylS may be mutated alone and its ability to enhance gene expression when used with a wild-type Pm promoter (and optionally leader which may be mutant or wild-type) may be tested. The two mutated regions e.g. the mutated Pm promoter and the mutated region which encodes the mRNA leader may then be combined and the ability of the combination to enhance gene expression can be assessed by methods previously described. Similarly the triple combination may be tested.

Alternatively, the Pm promoter may be mutated in a first instance, and a library of mutated Pm promoters may be generated, and their ability to enhance gene expression can be assessed. Highly expressing Pm promoter mutants may be selected. Such Pm mutants may then be used in a second mutagenesis procedure, to generate and identify mRNA leader mutants and/or XylS mutants. This is described in more detail in relation to Pm/leader mutants in Example 2, below. An mRNA leader-encoding sequence may be placed downstream of a mutated Pm promoter and may then be subjected to mutagenesis. The combination mutants can then be screened for the ability to enhance gene expression (for example, as compared to the mutant promoter/wild-type leader). A library of leader mutants may thus be generated, each with the same mutant Pm promoter. A similar procedure may be conducted with a XylS-encoding sequence.

Alternatively, the procedure may be carried out the other way round, first mutating the leader (or XylS) to obtain a library of leader (or XylS) mutants, selecting a particular leader (or XylS) mutant and using that to generate a library of combined leader (or XylS)/promoter mutants. Further, alternatively a single mutagenesis procedure may be carried out to mutate both promoter and leader (or XylS) e.g. using a cassette mutagenesis procedure with a synthetic oligonucleotide covering both regions. Analogously, a single mutagenic procedure may be carried out to mutate all three elements.

Particularly, mutated in Pm promoters may be screened for the ability to enhance gene expression and a mutant which allows particularly high gene expression may be used for generating a library of mutated mRNA leaders and/or XylS).

A mutant element, be it promoter or leader or XylS or any two or all three combined (e.g. both promoter and leader), may be subjected to repeated or iterative rounds of mutagenesis to "improve" the mutants obtained, for example to increase the level of enhancement of expression. Thus a mutant selected from a first round of mutagenesis may then be selected to a further round, and a mutant may then further be selected and mutated further etc. Thus for example, the Pm promoter may be subjected to two rounds of mutagenesis and selection in order to identify a mutant which can express particularly high levels of gene product. In this way, a particularly effective combination may be selected for.

Further, combinations (e.g. Pm promoter and mRNA leader mutations) can be selected which may be particularly suited to enhancing expression of a particular gene. Hence, such mutants may be identified by mutating and/or using them in an expression system with the desired gene and mutants giving the highest levels of enhanced expression of that gene may be selected. However, mutated combinations (e.g. mutated Pm promoters and mRNA leaders) which are found to enhance gene expression with one gene can also be used to enhance gene expression from a different gene.

The mutated Pm promoter an mRNA leader or XylS sequence may have at least 30%, 40%, 50%, 60%, 70%, 80%, 90%, 95%, 96%, 97%, 98% or 99% identity to the sequence of the wild-type (e.g. native) Pm promoter, wild-type (e.g. native) mRNA leader or wild-type (e.g. native) XylS/xylS sequence. Identity may be determined using the BestFit program of the Genetics Computer Group (GCG) Version 10 software package from the University of Wisconsin. The program uses the local hand algorithm of Smith and Waterman with the default values: Gap-creation penalty=8, Gap extension penalty=2, Average match=2.912, Average mismatch=2.003.

The nucleic acid molecule of the invention is capable of enhancing expression of a desired gene product. At its most basic, the nucleic acid molecule must be present in an expression system for expression of the desired gene, such that it may be expressed under the control of a Pm promoter (e.g. the mutated Pm promoter). Also included may be other transcriptional or translational control elements necessary or desirable to achieve or optimise expression.

Particularly, the invention provides a vector comprising the nucleic acid molecule of the invention, which may be a plasmid (including e.g. phagemids or cosmids) or artificial chromosome or a viral vector, or a construct (e.g. expression cassette) for insertion into a vector. The vector may be autonomously replicating or for chromosomal integration (e.g. a transposon-based vector or with sites for specific or homologous recombination for integration into the chromosome of the host cell into which the vector is introduced).

A vector may be introduced into a host cell, and the host cell may be grown or cultured to allow said gene to be expressed, e.g. under conditions which allow the gene to be expressed. Such expression methods are well known in the art and widely described in the literature. The invention hence further provides a host cell or a library comprising the nucleic acid molecule or the vector as described herein. The host cell may be any convenient or desired host cell, and may be prokaryotic or eukaryotic. Thus, all types of prokaryotic cells are included, most notably bacteria, and eukaryotic cells may include yeast or mammalian cells. Prokaryotic expression systems are however preferred and particularly bacterial expression systems. Accordingly the desired gene is preferably expressed in a bacterial host cell. Also encompassed is a bacterial chromosome comprising the nucleic acid of the invention.

In a further embodiment, the present invention thus provides an expression system comprising the nucleic acid molecule described herein which is used to produce the desired gene product whose expression is enhanced. The expression system may be an in vivo or in vitro system. The expression system according to the invention thus comprises any two or all three of the mutant elements, namely at least two of a mutated Pm promoter, a mutated region corresponding to an mRNA leader and a mutated XylS-encoding sequence, and a gene which encodes the desired gene product.

An expression system or vector may contain any further elements necessary or desirable for expression e.g. enhancer sequences. Regulatory features may also be present e.g. start or stop codons, transcriptional initiators or terminators, ribosomal binding sites etc.

Further, selectable markers are also useful to include in the expression systems or vectors to facilitate the selection of transformants. A wide range of selectable markers are known in the art and are described in the literature. For example, antibiotic resistance markers can be used or the TOL plasmid XlylE structural gene can be used. This encodes the product C230 which may readily be detected qualitatively or assayed. Spraying a plate of bacterial colonies with catechol rapidly distinguishes $C230^+$ colonies since they turn yellow due to the accumulation of 2-hydroxy muconic semialdehyde, enabling transformants/transconjugants etc. rapidly to be identified by the presence of XylE in the vectors.

As previously mentioned, the expression system may also comprise a reporter gene or tag e.g. which may be translationally coupled to the gene of interest. Representative reporter genes include any antibiotic resistance genes e.g. bla, or any gene encoding a detectable product or an enzyme which catalyses a detectable reaction e.g. luc.

The expression system may conveniently be in the form of a vector, as mentioned above. As noted above, a range of vectors are possible and any convenient or desired vector may be used e.g. a plasmid vector or a viral vector. A vast range of vectors and expression systems are known in the art and described in the literature and any of these may be used or modified for use according to the present invention. In a representative embodiment, vectors may be used which are based on the broad-host-range RK2 replicon. For example WO 98/08958 describes RK2-based plasmid vectors into which the Pm/xylS promoter system from a TOL plasmid has been introduced. Such vectors represent representative plasmid vectors which may be used according to the present invention. Alternatively, any vector containing the Pm promoter may be used, whether plasmid or in any other form, e.g. a vector for chromosomal integration, for example a transposon-based vector. Vectors designed for chromosomal integration, for example integration into a bacterial chromosome, are particularly advantageous since they avoid the problems which are known to be encountered during plasmid-based industrial processes, such as plasmid instability and negative effects of the plasmid on cell-growth. Integrating vectors are therefore preferred according to the present invention. The expression system (or expression construct) according to the present invention accordingly is preferably integrated into the genome or chromosome of the host cell used for the expression. As noted above, the mRNA leader may preferably be or may be derived from the leader of the Pm promoter and accordingly, in one representative embodiment, the Pm promoter is used with a Pm mRNA leader.

The vectors may, as noted above, be in autonomously replicating form, typically plasmids, or may be designed for chromosomal integration. This may depend on the host organism used, for example in the case of host cells of *Bacillus* sp. chromosomal integration systems are used industrially, but are less widely used in other prokaryotes. Generally speaking for chromosomal integration, transposon delivery vectors or suicide vectors may be used to achieve homologous recombination (transposon delivery vectors may be considered as suicide vectors since they cannot replicate in the host). Transposons may contain an antibiotic resistance marker. In bacteria, plasmids are generally most widely for protein production.

As noted above, any prokaryotic or eukaryotic cell may be used for expression, but preferably, a prokaryotic cell. This includes both Gram negative and Gram positive bacteria. Suitable bacteria include *Escherichia* sp., *Salmonella, Klebsiella, Proteus, Yersinia, Azotobacter* sp., *Pseudomonas* sp., *Xanthomonas* sp., *Agrobacterium* sp., *Alcaligenes* sp., *Bordatella* sp., *Haemophilus influenzae, Methylophilus methylotrophus, Rhizobium* sp., *Thiobacillus* sp., *Streptomyces* sp. and *Clavibacter* sp. In a particularly preferred embodiment, expression of the desired gene product occurs in *E. coli*. Eukaryotic host cells may include yeast cells or mammalian cell lines.

The desired gene product may be encoded by any desired or cloned gene, including partial gene sequences, or any nucleotide sequence encoding a desired expression product, including fusion protein products. Hence the term "gene" refers to any nucleotide sequence which it is desired to express.

The gene product may be any protein it is desired to produce. The term "protein" is used broadly herein to include any protein, polypeptide or peptide sequence. This may for example be a commercially or industrially important protein. Desired gene products may thus include therapeutically active proteins, enzymes or any protein having a useful activity e.g. structural or binding proteins. Representative proteins may thus include enzymes involved in biosynthetic pathways or which make or are involved in the production of any useful product.

The present invention is based on identifying mutants of Pm and leader or XylS mutants which result in enhanced expression. As noted above, the effects of some mutants, particularly the leader mutants, may be to some extent gene-dependent. In the context of a particular desired gene therefore, it may be advantageous to generate a mutant library and to screen that library in the context of the desired gene. The frequency of mutants reaching a desired expression level may be low and hence a large library size and an efficient screening method may be important, particularly a screening method which is selective for the desired gene. The mutations which enhance expression may be distributed throughout the region(s) subjected to mutagenesis, and appear to occur randomly. A random mutagenesis procedure may therefore be advantageous. The cassette mutagenesis procedure is particularly well-suited. The method of the invention may thus involve generating mutants and then screening them to select appropriate expression-enhancing mutants which are used for the subsequent expression of the desired gene.

Accordingly, a further aspect of the invention also provides a method of enhancing expression of a desired gene product wherein said gene product is expressed from a Pm promoter, said method comprising:

a) introducing one or more mutations into two or more elements selected from a Pm promoter, the DNA corresponding to the mRNA leader and a DNA sequence encoding XylS b) selecting a combination comprising at least two of a mutant Pm promoter, a mutant mRNA leader and mutant XylS which enhances expression of the desired gene;

c) expressing said gene using the mutant combination.

As described previously, step a) may comprise a multi— e.g. two step method of mutagenesis, where mutations are firstly introduced into a first element (e.g. the Pm promoter), mutated elements enhancing expression (e.g. highly expressive promoters) are selected and a second round of mutagenesis may be carried out to produce mutants which may be even higher expressers, etc.

Further, as previously described, mutation of the elements (e.g. the Pm promoter and mRNA leader) may occur separately or together. Hence, an element, (e.g. the Pm promoter) may be mutated initially and a screening step may be carried out to select highly expressing mutants. A second, or second and third elements (e.g. the mRNA leader) may be mutated separately and again a selection step may be carried out. The various mutant elements (e.g. Pm promoters and mRNA leaders) may then be combined. Alternatively, a first element (e.g. the Pm promoter) may be mutated in the first instance (and selection may be carried out for high expressers). A second element or second and third elements (e.g. an mRNA leader and/or XylS) (selected according to choice) may then be placed downstream of the mutant first element (e.g. mutant Pm promoter), advantageously in the context of an expression system (e.g. vector). The element(s) (e.g. mRNA leader and/or XylS) attached to the mutated first element (e.g. mutated Pm promoter) may then be mutated and a highly expressing combination may be selected. If three mutant elements are to be combined, this may be done sequentially, or two such elements may be mutated together for combination with a mutated third element, or vice-versa. Thus, for example, the Pm promoter and mRNA leader may further be mutated simultaneously in the same reaction. Alternatively, the procedure may be carried out vice versa, with the leader mutated first.

A further aspect of the present invention includes a method of obtaining a nucleic acid molecule of the present invention capable of enhancing the expression of a desired gene, said method comprising:

a) introducing one or more mutations into two or more elements selected from a Pm promoter; a DNA corresponding to an mRNA leader and a DNA sequence encoding XylS;

b) selecting a combination comprising at least two of a mutant Pm promoter, a mutant mRNA leader and a mutant XylS which enhances expression of the desired gene.

More particularly in the above methods, the mutations introduced into the promoter and/or XylS in step (a) enhance gene expression. Similarly the mutations introduced into the leader step (a) enhance expression of the desired gene.

In the context of the specific embodiment of Pm/mRNA leader mutants, the invention can be seen as provide a method of enhancing expression of a desired gene product wherein said gene product is expressed from a Pm promoter, said method comprising:

a) introducing one or more mutations into a Pm promoter;

b) introducing one or more mutations into the DNA corresponding to the mRNA leader;

c) selecting a mutant Pm promoter and mutant mRNA leader combination which enhance expression of the desired gene;

d) expressing said gene using the mutant Pm promoter and mutant mRNA leader combination.

As described previously, step a) may comprise a multi— e.g. two step method of mutagenesis, where mutations are firstly introduced into the Pm promoter, highly expressive promoters are selected and a second round of mutagenesis may be carried out to produce mutants which may be even higher expressers, etc.

Further, as previously described, mutation of the Pm promoter and mRNA leader may occur separately or together. Hence, the Pm promoter may be mutated initially and a screening step may be carried out to select highly expressing mutants. The mRNA leader may be mutated separately and again a selection step may be carried out. The various mutant Pm promoters and mRNA leaders may then be combined. Alternatively, the Pm promoter may be mutated in the first instance (and selection may be carried out for high expressers). An mRNA leader (selected according to chance) may then be placed downstream of the mutant Pm promoter, advantageously in the context of an expression system (e.g. vector). The mRNA leader attached to the mutated Pm promoter may then be mutated and a highly expressing combination may be selected. The Pm promoter and mRNA leader may further be mutated simultaneously in the same reaction. Alternatively, the procedure may be carried out vice versa, with the leader mutated first.

A further aspect of the present invention includes a method of obtaining a nucleic acid molecule of the present invention capable of enhancing the expression of a desired gene, said method comprising:

a) introducing one or more mutations into a Pm promoter;

b) introducing one or more mutations into the DNA corresponding to an mRNA leader;

c) selecting a Pm promoter and an mRNA leader mutant combination which enhances expression of the desired gene.

More particularly in the above methods, the mutations introduced into the promoter in step (a) enhance gene expression. Similarly the mutations introduced into the leader in step (b) enhance expression of the desired gene.

The step of introducing the mutations can be seen to generate libraries of Pm promoter mutants, mRNA leader mutants, XylS mutants, Pm promoter and mRNA leader mutants Pm and XylS mutants, XylS and leader mutants and/or Pm, leader and XylS mutants. These libraries can be screened to select mutants which enhance expression of a desired gene.

The libraries may contain two or more mutants, preferably 3, 4, 5, 6, 8, 10, 12, 15, 18, 20, 22, 25, 30, 40, 50 or more mutants.

The method of this aspect of the invention may thus be seen as a method for screening or identifying or selecting combination mutants comprising mutations in at least two of Pm, mRNA leader and XylS, e.g. Pm promoter and mRNA leader combination mutants.

As previously described, one or more mutations can be introduced into the Pm promoter, mRNA leader and/or XylS by any method known in the art. Particularly, however, the Pm promoter, mRNA leader and/or XylS may be mutated using a randomly mutagenised oligonucleotide where mutations are introduced by using a "doped" nucleotide mix. In particular, mutations may be introduced into the Pm promoter using synthetic oligonucleotides, where the first oligonucleotide corresponds to the wild-type Pm sequence and the oligonucleotide corresponding to the other strand is randomly mutagenised by the use of a mixed oligonucleotide mix which has been doped. PCR then results in the production of Pm promoter mutants which can be transformed into a library. Alternatively, Pm promoter mutants may be produced using a similar method but where the first oligonucleotide sequence is based on that of a known Pm high expresser.

As described above, the methods of screening can be used to select a mutant Pm promoter and/or ITS and/or XylS which is tailored or selected for particularly high enhanced expression for a particular gene, although such mutants can in any case then be used to enhance expression of other gene products.

The selection of a Pm promoter mutant and/or an mRNA leader mutant and/or XylS mutant which can enhance expression of the desired gene product may be carried out using methods well known in the art. For example, the activity of the gene product can be measured, e.g. by ELISA or a similar assay, and the activity obtained using the mutant Pm promoter and/or the mutant mRNA leader and/or mutant XylS can be compared to that obtained using the wild-type Pm promoter and/or leader and/or XylS. Hence, a comparison of the activity levels obtained when using e.g. both the wild-type and mutant Pm promoter and mRNA leader sequences will identify those mutants which have enhanced protein activity and hence gene expression. Alternatively transcript levels may also be directly assessed or determined to select the mutants. A mutant Pm promoter and/or mRNA leader and/or XylS can be assessed for their ability to enhance gene expression by either investigating the levels of a reporter gene product which is produced (which can either be produced on its own, or as a fusion protein with the desired gene product, or more advantageously by translational coupling of reporter gene expression to the expression of the desired gene), or by directly investigating the levels of desired gene product produced. Hence, in a preferred embodiment the selecting step may involve the assessment or determination of levels or the activity of a reporter gene. In a particularly preferred embodiment the reporter gene is an antibiotic resistance marker e.g. bla or encodes a detectable product, or a product which results in the production of a detectable product e.g. luc or celB. Therefore, Pm promoter mutants and/or mRNA leader mutants and/or XylS mutants which can enhance expression can be screened for example by detecting colonies of cells transformed with the expression system comprising the mutant Pm promoter and/or mutant mRNA leader and/or mutant XylS and reporter gene, which can grow on media containing high concentrations of penicillin (when the reporter gene is bla) or other antibiotic. For example, a penicillin concentration in the range 1-15 mg/ml, may be used to select high expressers. Alternatively, the amount of gene product obtained with the mutant Pm promoter and/or mRNA leader and/or XylS can be measured using for example Western blotting and compared to that obtained when using the wild-type Pm promoter and/or wild-type leader and/or XylS. Those mutants having enhanced expression as defined herein are selected in accordance with the present invention. Such a method may not be practical for low frequency mutants.

Enhanced transcription can also result in enhanced gene expression and Pm promoter mutants, and/or mRNA leader mutants and/or XylS mutants which enhance transcription can be detected using methods such as Northern blotting and microarray technologies.

In a further embodiment, the invention provides a method of obtaining a mutant combination comprising at least two mutant elements selected from a (i) a mutant Pm promoter (ii) a mutant mRNA leader; and (iii) a mutant XylS wherein said mutant combination is capable of enhancing expression of a desired gene, said method comprising the steps of a) introducing one or more mutations into two or more elements elected from the Pm promoter, the mRNA leader sequence of interest and a DNA sequence encoding XylS, b) producing a library comprising said mutant sequences upstream of the gene of interest or of a reporter gene, and c) screening the library for mutant combinations which enhance expression of said desired gene product.

In a particular embodiment of such a method, the invention provides a method of obtaining a Pm promoter and an mRNA leader mutant combination which is capable of enhancing expression of a desired gene, said method comprising the steps of a) introducing one or more mutations into the Pm promoter, b) introducing one or more mutations into the mRNA leader sequence of interest, c) producing a library comprising mutant Pm promoter and mutant mRNA leader sequences upstream of the gene of interest or of a reporter gene, and d) screening the library for Pm promoter and mRNA leader mutants which enhance expression of said desired gene product.

In this way, a library of combination mutants (e.g. mutated Pm promoter and mRNA leader sequences) can be screened, wherein clones expressing protein at the required levels can be selected using methods described above e.g. Western blotting, or by using a reporter gene e.g. bla. By using the desired gene of interest in the method of screening, mutant combinations (e.g. mutant Pm promoter and ITS sequences) which are tailored or optimum or selected for enhanced expression of that gene can be selected. If a reporter gene alone is used in the method of screening, then mutant combinations (e.g. mutated Pm promoter and ITS sequences) which may have general application may be selected.

However, since the effects of the mutants can be gene-dependent, it is preferred to select the mutants with reference to the desired gene. Since it would be laborious to design and construct separate expression systems for every desired gene, the inventors have devised a system where the expression of the desired gene (i.e. the test or target gene) is coupled to the expression of a reporter gene. This may be achieved by translational coupling using the phenomenon of translational reinitiation (Adkin and Van Duin, *J. Mol. Biol*, 213:811-818, 1990; André et al. *FEBS Lett.*, 468: 73-78, 2000). Thus, the desired (test) gene may be inserted into an expression vector upstream of the Pm promoter and a reporter gene is inserted as a second gene in such a way that its translation is coupled to the translation of the upstream gene (the desired or test gene) through overlapping or closely positioned stop and start sites. Thus the level of expression of the desired gene determines the level of expression of the reporter gene. Reporter gene expression is thus an indicator of the level of desired gene expression, and may be determined to determine desired gene expression. Convenient reporter genes to use are antibiotic resistance genes for example bla or the Kanamycin resistance gene. Any desired gene may thus be inserted into such a "screening vector" which may contain a mutant Pm promoter and/or mRNA leader and/or XylS for selection. A library of mutants may be generated in such a "screening vector". Such coupled genes may constitute an artificial operon which may be used in the selection step.

Accordingly, in a preferred embodiment, an artificially constructed operon can be used to screen mutant combinations (e.g. mutant Pm promoter and/or mutant mRNA leader sequences) in a library or otherwise. Such an operon may be contained in any convenient vector, for example in a plasmid. Such an operon incorporates the desired gene whose expression is to be enhanced and a reporter gene, conveniently an antibiotic resistance marker gene e.g. bla (which encodes beta-lactamase and confers resistance to penicillin as previously described). The desired gene is positioned upstream of the reporter gene and the reporter gene is expressed by translational coupling with the desired gene. The vector may further comprise the mutant combination (e.g. the mutant Pm promoter and mutant mRNA leader sequence) upstream. Hence, the gene product is produced together with the reporter gene and in such a way, the expression of the reporter gene can be used to measure the expression of the desired gene.

The present invention accordingly provides a method of identifying (or screening for) a combination mutant comprising at least two of a mutant Pm promoter, mutant mRNA leader and mutant XylS (e.g. a Pm promoter and an mRNA leader combination mutant) which enhances expression of a desired gene, said method comprising:

providing a vector comprising a desired gene and a reporter gene translationally coupled thereto;

introducing at least two of a Pm promoter mutant, a DNA sequence corresponding to an mRNA leader mutant and a DNA sequence encoding a mutant XylS (e.g. a Pm promoter mutant and a DNA sequence corresponding to an mRNA leader mutant) into said vector upstream of said desired gene;

determining the level of expression of said reporter gene.

By determining the level of reporter gene expression, the level of desired gene expression may be determined.

Where such a mutant combination does not include a mutant Pm, the vector will also include or be provided with an unmutated Pm promoter e.g. a native Pm.

Mutants which enhance expression of the desired gene may be determined by comparing the level of expression (i.e. reporter gene expression) with that obtained using the corresponding unmutated (i.e. wild-type) combination (e.g. unmutated or wild-type Pm promoter and leader).

The mutant library (e.g. mutant Pm promoter and mRNA leader library) can be made in prokaryotic cells, preferably in E. coli. Other cell types can be used to create the library, examples of which have been described supra. Hence, mutant libraries can be created using for example the expression systems already described or the artificially constructed operon. Such a library is plated onto agar plates, where the number of transformants may be about 100000. Clones containing the artificially constructed operon can be selected for by antibiotic resistance, e.g. by resistance to ampicillin, where such a resistance gene is also present in the operon or vector containing the operon. Appropriate selectable markers have been discussed supra. High expression mutants can be screened for by detecting enhanced expression of the reporter gene or the desired gene product and can be sequenced to identify the mutation(s) responsible for enhanced expression.

Further encompassed by the present invention is an artificially constructed operon, or a vector, comprising the desired gene, translationally coupled to a reporter gene, wherein said desired gene and reporter gene are under the control of a mutant combination (e.g. mutant Pm promoter and a mutant ITS or mRNA leader), as defined herein.

This aspect of the invention may provide a vector for selection or identification of a combination mutant (e.g. a Pm promoter and an mRNA leader combination mutant) as defined herein, said vector comprising a desired (or test) gene and a reporter gene translationally coupled thereto, and a site for insertion of said mutant combination (e.g. a Pm promoter mutant and a DNA region corresponding to the said leader mutant) upstream of said desired gene.

In a further aspect, the vector may comprise the mutant combination (e.g. the Pm promoter mutant and DNA region corresponding to the said leader mutant) upstream of said desired gene. Accordingly the invention also provides a library of such vectors. The vectors in the library may comprise different combination mutants e.g. different Pm promoter and mRNA leader mutants.

The use of a such an operon or vector for screening of mutant combinations (e.g. mutant Pm promoter and ITS/mRNA leaders) for sequences which result in enhanced expression of a desired gene is also encompassed.

As noted above, the methods of the invention find particular utility in the commercial or industrial production of proteins. In a preferred aspect, therefore the methods of producing a protein or of enhancing expression of a protein relate to production-scale processes i.e. they are carried out on a production-scale or industrial scale, rather than a laboratory experiment. The processes may be preferred in a bio-reactor or fermentor, particularly a production-scale bio-reactor or fermentor.

Figure 5:
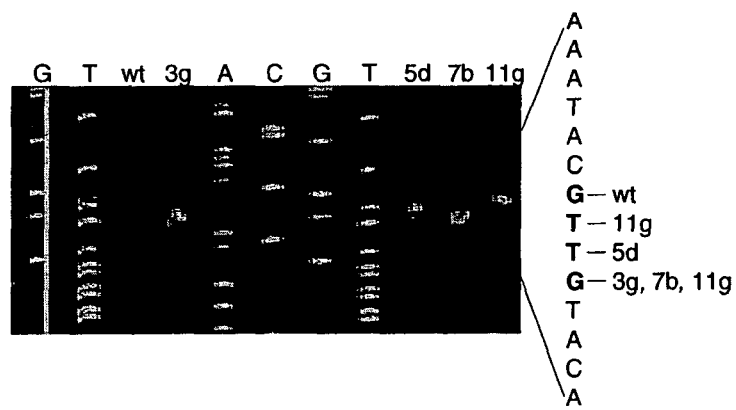
Figure 7:
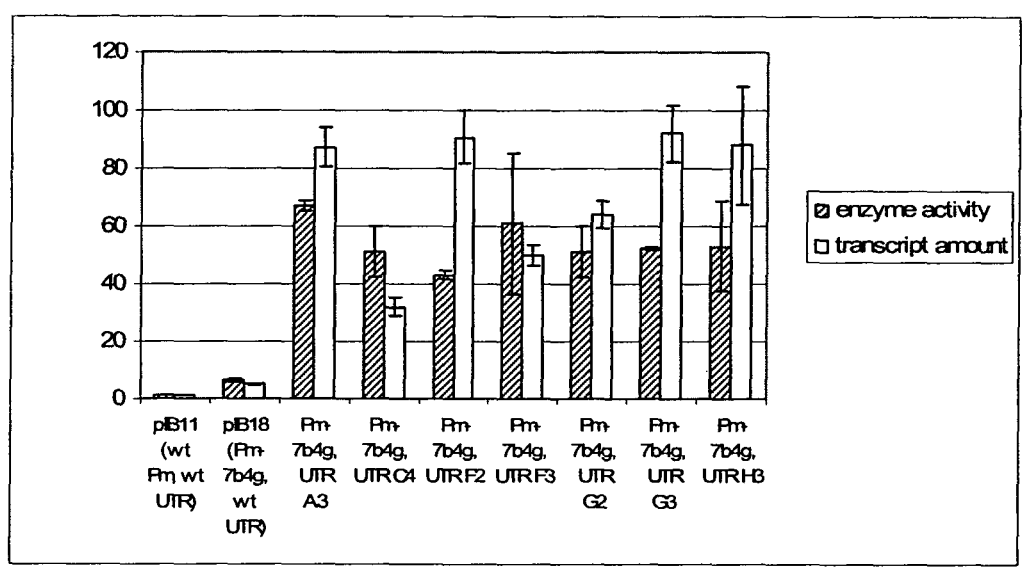
Figure 8:
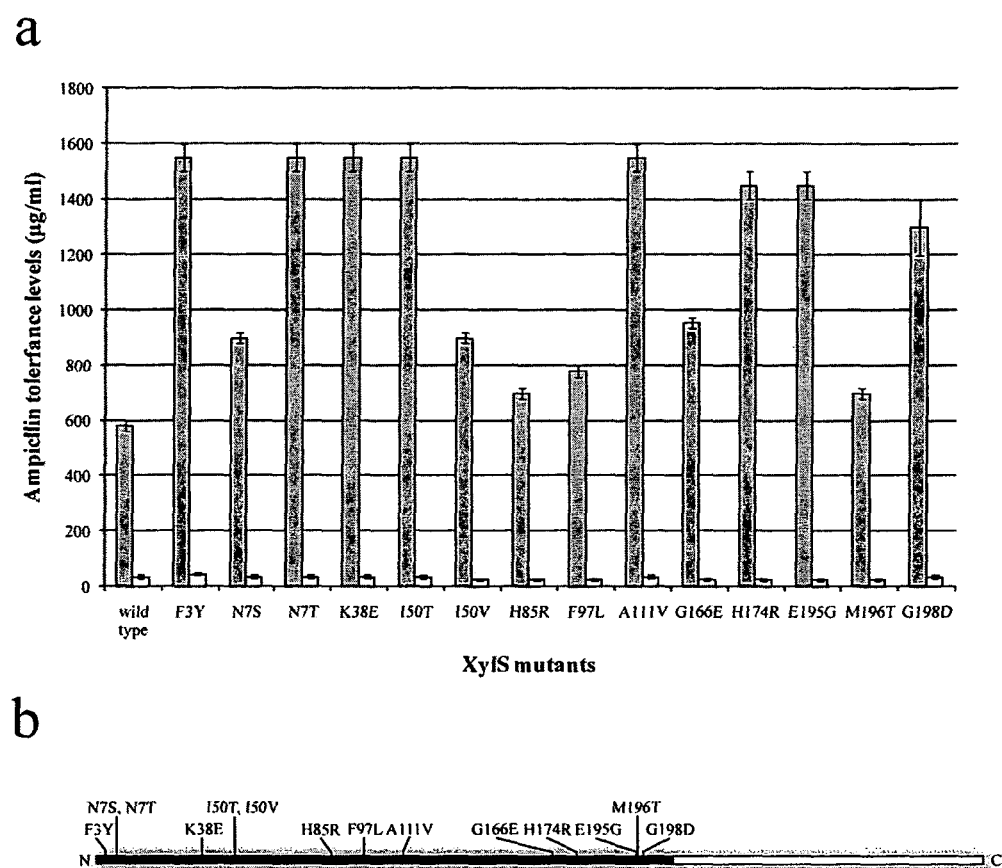
Figure 9:

The invention will now be described in more detail in the following non-limiting Examples with reference to the following drawings:

FIG. 1 shows a map of the plasmid pIB6. The restriction sites shown are unique. bla, gene encoding β-lactamase; kan, kanamycin resistance gene; trfA, gene encoding the essential replication protein; xylS, gene encoding the activator XylS; oriV, origin of vegetative replication; oriT, origin of transfer; t, bidirectional transcriptional terminator; TTT, transcriptional terminator. Details for the transcription and translation initiation regions of Pm are displayed above the plasmid map (SEQ ID NO. 100). The transcription initiation site shown is determined in this study;

FIG. 2 shows the fraction of cells with increased ampicillin resistance for Pm mutant libraries Library 1 (circles), Library 2 (triangles), and for a culture of cells containing the plasmid pIB6 (stars). Cell cultures with mutant libraries were grown in L broth for 1 hour at 37° C., induced with m-toluate (2 mM) and grown further at 30° C. for 3.5 hours. Cells were plated out on agar medium containing inducer and ampicillin at concentrations shown in the figure. Cells with pIB6 were grown at 37° C. for approximately 4 hours before plated out on agar medium with ampicillin;

FIG. 3 shows sequences of the −10 Pm region as determined for high expression mutants identified from Library 1 (A) (SEQ ID NOs 101-119) and Library 2 (B) (SEQ ID NOs 120-124). (C) Sequences for high expression mutants identified by selection on high ampicillin concentrations in the absence of m-toluate (SEQ ID NOs 125-137). Ampicillin resistance was determined from growth on agar plates with the following ampicilin concentrations (mg/ml): 0.0025-0.005-0.015-0.065-0.1-0.15-0.2-0.3-0.4-0.5-0.6-0.7-0.8-0.9-1.0-1.1 (without m-toluate) and 0.5-1.0-1.5-2.0-2.5-3.0-3.5-4.0-4.5-5.0 (with 2 mM m-toluate). Restriction sites are shown in italics, the positions subjected to mutagenesis are shown in bold, the nucleotide in the −10 position is underlined, and the transcription start sites as determined in this study are shown in capital letters;

FIG. 4 shows relative expression as determined from transcript quantitation and enzyme activity of β-lactamase (A), CelB (B), and luciferase (C) from selected Pm mutants Relative transcript amounts were estimated by a reverse transcriptase/real-time PCR strategy;

FIG. 5 shows transcription start sites for the β-lactamase transcript from cells with wt Pm (pIB6) and Pm mutants in IB6. (A) Mapping of transcriptional start sites. The DNA sequences (right) are complementary to the sequences shown in (B). Transcription start sites are shown in bold. (B) Sequence alignments showing the DNA sequences of the −10 region and transcription start sites for Pm mutants (SEQ ID NOs 138-142). transcription start sites are shown in bold capitals and the −10 positions are underlined;

FIG. 6 shows DNA sequences for the −10 region of Pm and two high expression Pm mutants used in this study (A) (SEQ ID NOs 143-145) and for the UTR of high expression mutants identified from library Pm-7b4g-UTR (b) (SEQ ID NOs 146-163). Ampicillin resistances were determined from growth on agar plates with 0.1 mM m-toluate and the following concentrations (mg/ml): 0.25-0.5-1-1.5-2-3-4-5-6-7-8-9-10-11-12. The resistance data yields the UTR sequences in the pIB18 construct; that is in combination with the high expression mutant Pm-7b4g. Restriction sites are shown in italics, identical positions are shown as dots and deletions are shown as dashes;

FIG. 7 shows relative expression of β-lactamase for Pm/UTR high expression mutants as determined from transcript quantification (real time PCR) and enzyme activity assays. Error bars indicate the standard deviations between two parallel experiments where samples were obtained from independently grown cell cultures;

FIG. 8 shows substitutions in XylS that increase transcription from Pm in the presence of effector (1 mM m-toluic acid). (a) Ampicillin tolerance levels of cells containing different xylS mutant genes. The tolerance levels in the presence of effector are shown in grey bars, the tolerance levels in the absence of effector are shown in white bars. (b) A schematic representation of the XylS activator showing the N-terminal domain in black and the C-terminal domain in white. The locations of the mutations are indicated;

FIG. 9 shows a map of the first 200 residues of XylS mutant activators with each mutation shown as a black dot. The figure includes XylS mutant activators combined (designated Syn) and XylS mutant activators isolated after DNA shuffling (designated StEP).

EXAMPLE 1

Identification of High Expression Pm Promoter Mutants

Materials and Methods
Bacterial Strains, Plasmids, and Growth Media

The bacterial strain and plasmids used in this study are described in Table 1. In all experiments, cells were grown in L broth (10 g/liter tryptone, 5 g/liter yeast extract, and 5 g/liter NaCl) or on L agar at 37° C., except for expression studies were 30° C. was used. Antibiotics were used at the following concentrations: kanamycin (Km), 50 µg/ml; tetracycline, 15 µg/ml. Ampicillin was used in expression studies, and concentrations are reported with the results.
DNA Manipulations Plasmid DNA was prepared by the WizardPlus SV minipreps DNA purification kit (Promega). Transformations of E. coli were performed by use of heat shock-competent rubidium chloride-treated cells. Enzymatic manipulations were performed as described by the manufacturers. DNA was extracted from agarose gel slabs using the Qiaquick gel extraction kit (Qiagen). PCR reactions were performed using the Expand High Fidelity PCR system kit (Roche) for cloning purposes. When PCR was used for generation of templates for DNA sequencing, the polymerase DynazymeII (Finnzymes) was used. PCR templates were treated with the enzyme mixture ExoSapIt (USB) prior to DNA sequencing. Sequencing reactions were carried out using the ABI PRISM BigDye sequencing kit (Applied Biosystems), and analyzed using an ABI 3100 Genetic Analyzer (Applied Biosystems). A down-mutation in the mRNA leader sequence of Pm previously identified by Winther-Larsen et al. (*Metab. Eng.* 2: 92-103, 2000) was introduced into pIB3 using two annealed, complementary oligonucleotides with the mutated Pm leader mRNA sequence and SpeI- and NdeI-compatible ends. The small DNA fragment was cloned into the SpeI/NdeI sites of pIB3 generating pIB4. Sequences of oligonucleotides were 5'-CTAGTACAATAATAATG AAGTCATGAACA-3' (SEQ ID NO. 44) and 5'-TATGT-TCATGACTTCATTATTATTGTA-3' (SEQ ID NO. 45) (introduced mutations are underlined and restriction sites are shown in italics). The AflIII site upstream the Pm promoter of pIB5 was introduced by site specific mutagenesis of pIB4 using the QuikChange Site-Directed Mutagenesis Kit (Stratagene) as described by the manufacturers and the primers 5'-GCATAACCAGCATAAA CGTGTCCGGTTTGATAG (SEQ ID NO. 46) and 5'-CGA-TAACCAGCATAAACGTGTCCGGTTTGATAG (SEQ ID NO. 47). The BspLU11I site of pIB6 was introduced by site specific mutagenesis of the SpeI site of pIB5 using the primers 5'-CTTAGGCTTTATGCAAC ATGTACAATAATAATGAAGTCATG-3' (SEQ ID NO. 48) and 5'-CATGACTTCATTATTATTGTAC ATGTTGCATAAAGCCTAAG-3' (SEQ ID NO. 49). Cloning of the xylS gene from pIB6 into pPK34 to generate pIB14 was done by PCR amplification with the primers 5'-AACCGAGAATTCGCCGTTGGATAGCTCCGCTAC-3' (SEQ ID NO. 50) and 5'-AATGCATTGGTTCTGCAG-GAGAGTGTCTAAGAAAGCCGG-3' (SEQ ID NO. 51) which introduced the restriction sites for EcoRI and PstI, respectively, for cloning purposes.
Construction of the Pm Mutant Libraries It has previously been established that the ampicillin resistance level of host cells containing a plasmid-encoded β-lactamase gene (bla) is approximately proportional to the copy number of the plasmid (Uhlin and Nordström, *Plasmid*, 1, 1-7, 1977). The reason for this is that the expression increases as a function of the gene dosage, and this property can therefore also be used to estimate changes in the promoter activity. The plasmid pIB6 was used for construction of mutant libraries (FIG. 1), based on the vector pJT19bla previously used in studies of Pm mutants (Winther-Larsen et al., *Metab. Eng.* 2:92-103, 2000). In these constructs bla is a reporter of Pm activity. A kanamycin resistance gene (km) allows for plasmid selection without the involvement of Pm. The expression level of this expression system was lowered by introducing a mutation in the ribosome binding site. This mutation (GGAG→GAAG) has previously been found to reduce expression from Pm (Winther-Larsen et al. *Metab. Eng.* 2:92-103, 2000), and was introduced to avoid potential situations were expression exceeds levels detectable by ampicillin resistance.

To introduce mutations in the Pm region, a strategy involving synthetic oligonucleotides was used, similar to the protocol described by Winther-Larsen et al. (*Metab. Eng.* 2:79-91, 2000). Synthetic oligonucleotides were designed to constitute a double-stranded DNA fragment with the Pm-sequence and XbaI- and BspLU11I-compatible ends when annealed, for subsequent easy cloning into the pIB6 vector. For the first mutant library produced (Library 1) one of the oligonucleotides corresponded to the wt Pm sequence (5'-CATGTTGCATAAAGCCTAAGGGGTAGGCCTTT-3' (SEQ ID NO. 52)). The oligonucleotide corresponding the other strand was randomly mutagenized by the use of a mixed oligonucleotide mix (5'-CTAGAA13322412222441332444I432AA-3' (SEQ ID NO. 53), where the numbers in the oligonucleotide indicates the doping percentages of the nucleotides: 1=88% A, 4% C, 4% G, 4% T; 2=4% A, 88% C, 4% G, 4% T; 3=4% A, 4% C, 88% G, 4% T; 4=4% A, 4% C, 4% G, 88% T).

Before annealing a mix of 700 pmol of each of the oligonucleotides was phosphorylated by Polynucleotide Kinase. Subsequently NaCl was added to a final concentration of 200 mM and the phosphorylated oligonucleotides were annealed by gradual cooling from 95 to 20 degrees during 20 minutes (min) in a PCR machine. Dilutions of the resultant DNA fragment were ligated into XbaI-BspLU11I-digested plasmid pIB6 which had been purified by Qiaquick PCR purification kit and dephosphorylated by Calf Intestinal Phosphatase. The ligated plasmids were transformed into *E. coli* DH5α using km as a selection marker. The approximately 500 000 colonies obtained were mixed and used as a library of Pm mutants. A second mutant library (Library 2) was created by the same strategy, but the sequences of the oligonucleotides were based on the Pm high expression mutant 7b (see FIGS. 3a and b) identified from Library 1, using the oligonucleotides 5'-CATGTGCTAAAGTT-TAAGGGGTAGGCCTTT-3' (SEQ ID NO. 54) and 5'-CTAGAA13322412222441111244413CA-3' (SEQ ID NO. 55), where 1, 2, 3, and 4 are the doping numbers as described above. The size of Library 2 was estimated to approximately 500 000.

Screening for Pm Mutants and Determination of Ampicillin-Resistance

To identify mutants with increased expression from Pm, an aliquot of the mutant library was selectively grown at 37° C. with Km. After one hour cells were induced with m-toluate (2 mM) and grown further at 30° C. for 3 hours. The cells were plated out at about 1 million cells per plate on agar medium containing inducer and various ampicillin concentrations. The plates were incubated at 30° C. for approximately 20 hours and inspected for growth. Candidates growing at high ampicillin concentrations were then individually retested by the following procedure. Individual colonies were inoculated with 100 µL-broth with or without inducer in 96-wells microtiter plates (NUNC). The cells were incubated at 30° C. overnight and diluted twice by a 96-pin replicator and microtiter plates with 200 µl L-broth in each well. Subsequently, the 96-pin replicator was used to plate the cells on L agar with or without inducer at various ampicillin concentrations. The plates were incubated at 30° C. for approximately 20 hours before inspected for growth. The sequence of the Pm region was determined for selected high expression candidates using the sequencing primer 5'-GCATAACCAGCATAAACGTGTCCGGTTTGATAG-3 (SEQ ID NO. 56). A template PCR product was generated with the primers 5'-CTTTCACCAGCGTTTCTGGGTG-3' (SEQ ID NO. 57) and 5'-GATGTAGAAAGGCGC-CAAGTC-3' (SEQ ID NO. 58). All Pm mutants reported under Results were reproduced by one of the following strategies. For mutants where the BspLU11I site was intact, oligonucleotides analogous to those used for constructing the libraries were designed. However, the sequences of the oligonucleotides corresponded to the Pm sequence of the mutant to be reproduced. The oligonucleotides were phosphorylated, annealed, and cloned into the XbaI/BspLU11I-sites of pIB6 as described under "Construction of Pm mutant libraries". Finally the Pm region of transformants was sequenced as described above. For mutants where deletions had disrupted the BspLU11I site, the mutated Pm region was PCR amplified using the primers (SEQ ID NO. 59)
5'-CGACACGGAAATGTTGAATACTCATATGTT and (SEQ ID NO. 60)
5'-GCATAACCAGCATAAACGTGTCCGGTTTGATAG-3'.

The resultant products were purified using spin colomns (Qiagene) and cut by the restriction enzymes AflII/NdeI and recloned into the same sites of pIB6. Sequence of the Pm region of transformants were determined as described above, but another sequencing primer was used (5'-CTTTCACCAGCGTTTCTGGGTG-3' (SEQ ID NO. 61)) to obtain a complete sequence of the PCR amplified region.

Enzyme Assays

*E. coli* cells with the relevant plasmids were diluted 100-fold from an overnight culture grown in selective media and grown at 37° C. At an $OD_{600}$ of 0.1, the cells were induced by m-toluate at a concentration of 2 mM. The cells were further grown at 30° C. for 5 hours. Aliquots of cells were snap-frozen on dry ice and ethanol, and stored at −80° C. for subsequent enzyme assays. The method used for β-lactamase assay was a modified version of the method described by Chervaux et al. (1995, Mol. Gen. Genet., 249, 237-245), according to Winther-Larsen et al. (2000, supra). Cell-free enzyme extracts were made by sonication in an enzyme reaction buffer (80 mM $K_2HPO_4$, 20 mM $NaH_2PO_4$). β-lactamase activities were spectophotometrically measured at 240 nm at room temperature over a 4 min period in a Lambda 35 UV/VIS spectrometer (Perkin Elmer) using PenicillinG (Sigma) as a substrate. Total protein concentrations were determined using PROTEIN ASSAY (Bio-Rad). Luc activities were measured as described by Blatny et al. (*Appl. Env. Microbiol*, 63: 370-9, 1997), using the luciferase assay system from Promega and a TD-20/20 luminometer (Turner Design). CelB activities were measured as described by Fjærvik et al. (*FEMS Microbiol. Lett.*, 77: 325-330, 1991). For all enzyme assays, measurements were carried out with three recurrences for each sample. Further, all assays were repeated at least twice with samples obtained from independently grown cultures. All enzyme activity analyses were repeated at least twice with enzyme extracts obtained from independently grown cell cultures.

RNA Isolation, cDNA Synthesis, and Real-Time PCR

*E. coli* cells with the relevant plasmids were grown as described for enzyme assays. For stabilization of the RNA, cell cultures were treated with RNAprotect (Qiagen) prior to freezing of cell pellets for subsequent RNA isolation. RNA was isolated using the RNAqueous kit (Ambion) as described by the manufacturers. The concentration and purity of the RNA was examined by determining the absorbance at 260 and 280 nm in a Lambda 35 UV/VIS spectrometer (Perkin Elmer). The RNA preparations were treated with DNase (DNA-free, Ambion) to remove any contaminating DNA. cDNA was produced from 3 µg total RNA as template using the First-Strand cDNA synthesis kit (Amersham Biosciences) with random pd(N)$_6$ primers as described by the suppliers.

Real-time PCR was used for quantification of β-lactamase, luciferase, and celb transcripts. Primers were designed using the primer design program of Clone Manager version 6.0 (Scientific & Educational Software) to give products of approximately 250 base pares (bp). Primer sequences used for Real-Time PCR are given in Table 2. The iTaq™ SYBR® Green Supermix (Bio-Rad) was used for the Real-time PCR reactions, and the reactions were carried out in a MX3000 instrument (Stratagene). Optimal primer concentrations were determined for each primer set, and varied from 160 nM to 240 nM. Amplification for each sample was carried out in triplicate wells. The PCR cycles were as follows: 10 min at 96, followed by 40 cycles consisting of 30 sec at 95° C., 60 sec at 55° C., and 30 sec at 72° C. Relative quantities were determined using the software of MX3000 (Stratagene). cDNA produced from cells carrying plasmids with the wt Pm was used as a calibrator (pIB6, pØY9, pLB10 for bla, luc, and celB, respectively). A fragment from the Km resistance gene was used as a normalizer. Primer efficiencies were determined and found over 92% for all primer sets. The differences between the normalizer gene primer set and the all target gene primer sets were less than 5%. All real time PCR experiments were repeated for at least twice with cDNA samples obtained from independently grown cell culture Primer Extension Primer extension experiments were performed to determine the transcription initiation site. *E. coli* cells with the relevant plasmids were diluted 50-fold from an overnight culture grown in selective media. After growth at 37° C. for 90 min, the cultures were induced to a final concentration of 4 mM m-toluate, and further grown at 30° C. for 3.5 hours. Cell cultures were treated with RNAprotect (Qiagen) and cell pellets were frozen. RNA was isolated using RNAqeuous (Ambion), and subsequently precipitated with ethanol and sodium acetate. To avoid non-enzymatic degradation of RNA the concentrated RNA preparations were added EDTA to a final concentration of 0.05 mM. Approximately 15 ug total RNA and 2.5 pmol of a bla-specific primer with fluorescent label (6-FAM) at the 5'-end •(5'-CCGCTGTT-GAGATCCAGTTCG-3' (SEQ ID NO. 62)) was denatured by heating at 80° C. for one min and then chilled on ice. The cDNA synthesis was carried out using the Primer extension system with AMV reverse transcriptase (Promega) as described by the manufacturers. For production of sequencing ladders, a region of the bla gene amplified using the primers •5'-GCATAACCAGCATAAACGTGTCCGGTTT-GATAG (SEQ ID NO. 63) and •5'-GTGTATGCGGCGAC-CGAGTT 3' (SEQ ID NO. 64) was sequenced using the Sequenase Version 2.0 DNA sequencing kit (USB) and the same FAM-labeled primer as in the primer extension reaction. Prior to gel electrophoresis, the primer extension reactions were precipitated with ethanol and sodium acetate. Gel electrophoresis was performed using an ABI Prism 377 Sequencer (Applied Biosystems).

Results and Discussion

Characterization of the Mutant Library (Library 1)

A Pm mutant library was constructed using the plasmid pIB6 as described in Materials and methods (Library 1). In this construct the bla gene is a reporter for Pm, and altered ampicillin resistance thus reflects altered promoter activity. The mutant library was characterized by determining the fraction of cells growing at elevated ampicillin concentrations on agar plates with m-toluate. The ampicillin resistance was also examined in the same way for cells containing the wild-type Pm construct (pIB6). The results (FIG. 2) demonstrate that a higher frequency (relative to wild-type) of the cells from the library grew at elevated concentrations of ampicillin, indicating that the library probably contains promoter mutants which lead to more β-lactamase expression. The background of cells with elevated resistance in the wild-type population may be due to spontaneous mutations, perhaps even selected during slow growth on the agar-medium. Typically, these colonies had a mucoid phenotype, indicating production of an exopolysaccharide, which may be cholanic acid.

The Pm sequence was determined for about 20 randomly picked clones from the mutant library. Around 50% of these exhibited the wild type (wt) Pm sequence. This was expected, since only one of the DNA strands was mutagenized. Two of the clones were found to have multiple inserts of the mutagenized DNA fragment. For the rest, the average number of mutations was found to be 2.4 (sequence data not shown).

It appeared possible that the cells from the mutant libraries displaying the highest ampicillin resistance levels contain the desired Pm mutations, but in combination with other spontaneous mutations further contributing to the phenotype.

Identification of Mutants with Enhanced Expression Levels

Mutants with putatively increased Pm activity were identified by selection on agar plates with m-toluate and ampicillin concentrations ranging from 0.5 to 7 mg/ml. Pm sequences were determined for about a hundred candidates growing at high ampicillin concentrations, and the results showed that some mutants were represented more than once. To make sure the phenotypes were caused by the observed mutations the Pm region was resynthesized and substituted with the corresponding region in the wild-type plasmid. The sequences and phenotypes of these mutants (18 total) are shown in FIG. 3A. While cells with the wt Pm construct (pIB6) grew up to 0.5 mg/ml ampicillin, the high expression mutants grew up to 3.5 mg/ml ampicillin.

Compared to randomly picked mutants, the average number of mutations was high (approximately 5) for high expression mutants. Furthermore, all the high expression mutants were characterized by deletions in or close to the transcription initiation region. Sequences for the arbitrary picked mutants did not exhibit this feature. Coincidentally two mutants (m6, 12B) were identified that were changed relative to wt Pm only by deletions in the transcription initiation region. The ampicillin resistance data (FIG. 3A) indicates that the deletions contribute to approximately half of the increment in expression observed for the high expression mutants.

The majority of nucleotide substitutions were positioned in the region upstream of the −10 position. Generally, the spacer between the −10 and −35 elements of bacterial promoters has been considered to be important with respect to length rather than nucleotide sequence. Mutagenesis of the spacer of the P$_{lac}$ promoter, however, showed that the sequence highly affected the transcription initiation process (Liu et al., *PNAS*, 101:6911-6916, 2004). Our findings demonstrate that the sequence upstream of the −10 region of Pm strongly affects the promoter activity. Based on a comparison of 20 σ$^s$ dependent *E. coli* promoters, Lacour and Landini (*J. Bacteriol*, 186 7186-7195, 2004) proposed the −10 promoter element consensus sequence TG(N)$_{0-2}$CYA-TNCT. As shown in the alignments in FIG. 3, the TANNCT motif of the Pm promoter is conserved among all mutants (except mutant 7-2g from Library 2). Several mutants has acquired a T in the −9 position (as compared to the annotation of the wt Pm sequence in the alignment in FIG. 3), making this region more similar to the proposed consensus sequence. By using a SELEX based strategy, Gaal et al. (*Mol. Microbiol.*, 42:939-954, 2001) identified an optimized −10 promoter element for expression mediated by $\sigma^s$; TGTGCTATAC/AT (SEQ ID NO. 65). Some of the mutants exhibit a TATACT sequence element (SD, 7b-2d, 7b-5h). Interestingly, these mutants are characterized by high basal expression levels. Further, three of four mutants selected for high basal expression (Un3, Un19, and Un21, see FIG. 3C) exhibit a TG motif, not present in the Pm wt sequence, directly upstream the −10 element. This element is present both in the consensus sequence (Lacour and Landini, 2004, supra) and in the optimized −10 sequence element (Gaal et al., supra). The increased similarity to these sequence elements might reflect a stronger binding of $\sigma^s$, which could explain the high basal expression levels.

The basal expression level, determined as the ampicillin resistance when grown on agar medium in absence of inducer, varied extensively among mutants; from 0.005 to 0.8 mg/ml ampicillin (see FIG. 3a). Apparently, the ratio of induced to uninduced expression varies among mutants, but precise values cannot be calculated due to the discontinuous nature of the ampicillin resistance data. The finding of mutants with a very high basal expression level prompted a screen for mutants with high expression level in the absence of inducer. This screen identified mutant 5d (formerly identified from Library 1) and 3 additional mutants with a basal expression level that exceeded the induced expression level of the wt Pm. Pm sequences and ampicillin resistances are shown in FIG. 3b. The basal expression of the mutant Un 3 is approximately twice the induced expression level of the wt Pm construct (as assessed by ampicillin resistance data). For three of these four mutants a TG motif was introduced in the 5' proximity to the −10 element (see FIG. 3b), a characteristic typical to the −10 element of $\sigma^s$ dependent promoters (see consensus sequence above; Lacour and Landini, 2004).

The expression from Pm was further examined for the mutants m5, m8, 7b and 11G. Amounts of β-lactamase transcript from cells with pIB6 with Pm mutant relative to cells with pIB6 (wt Pm) was determined by a reverse transcriptase/real-time PCR strategy. The results are shown in FIG. 4a. These experiments corroborated the ampicillin resistance data, and demonstrated that a large increase in expression. For mutants 7b and m5, β-lactamase transcript amounts were estimated to reach approximately 7 times the amount produced from wt Pm (pIB6).

The expression levels for these mutants relative to wt Pm were further investigated by determining β-lactamase activities. It has previously been shown that enzyme activities reflect the protein amounts for phosphoglucomutase, luciferase (Blatny et al., *Plasmid*, 38:35-51, 1997), and β-lactamase (Winther-Larsen et al. *Metab. Eng.* 2:92-103, 2000). Results for the mutants relative to the wt Pm construct are shown in FIG. 4a. The enzyme activity data confirmed the high expression levels for these mutants compared to the wt Pm.

From these experiments it was concluded that a large increase in expression could be achieved by the cassette mutagenesis strategy.

Generation of Further Increment of Pm Activity by Production of a Secondary Mutant Library Based on a High Expression Pm Mutant Based on the Pm sequence of the high expression mutant 7b identified from Library 1, a new Pm mutant library was constructed (Library 2). As for Library 1, the fractions of cells growing at elevated ampicillin concentrations on agar plates with m-toluate were determined. The results showed that mutants exist in Library 2 that reaches considerable higher ampicillin resistances than the mutants in Library 1 (FIG. 2). Library 2 was further characterized by the determination of the Pm sequence for around 20 randomly chosen clones. Characteristics of these sequences were similar to what found for random Pm sequences in Library 1: Around 50% exhibited the wild type (wt) Pm sequence, two of the clones were found to have multiple inserts of the mutagenized DNA fragment, and for the rest the average number of mutations was found to be 2.7 (sequence data not shown).

High expression Pm mutants were identified by selection on agar plates with m-toluate and ampicillin concentrations from 3 to 8 mg/ml. Pm sequences and ampicillin resistances for 11 high expression mutants are shown in FIG. 3c. These mutants reached ampicillin resistances up to 4.5 mg/ml, compared to 3.5 for the mutant 7b from Library 1.

For the mutants 7b-2d, 7b-2g and 7b-4g, the expression from Pm was also investigated by determination of relative amounts of β-lactamase transcript and β-lactamase enzyme activities. The results are shown in FIG. 4a. These data demonstrate that an approximately 10 fold increase in expression was obtained after two rounds of mutagenesis of Pm.

Determination of Transcription Start Sites for Pm and Pm Mutants

All the high expression Pm mutants identified are characterized by deletions around the transcription initiation region. It was therefore speculated that the deletions could affect the start site selection in the transcription initiation process. For cells with pIB6 and pIB6 with the Pm mutants 3g, 5d, 7b, and 11g, the Pm transcription start site was determined by a primer extension approach. Results are shown in FIG. 5. The DNA sequencing ladder and primer extension products were fluorescently labeled and run on an ABI Prism 377 DNA sequencing machine. The scanning tool of the software was used to obtain exact positions on the gel for the primer extension and sequencing signals. In this way the signals could be precisely and unambiguously mapped relative to the sequencing ladders. Transcription from wt Pm was found to initiate from a C, as shown in FIG. 5. For all mutants surveyed, the transcription start site was changed relative to wt Pm (FIGS. 5a and b). It has previously been found that the efficiency of the transcription initiation process is influenced by the nucleotide in choice in the transcription start site (Lewis and Adhya, supra; Walker and Osuna, *J. Bacteriol.*, 184: 4783-4791, 2002). The change of transcription start site for the high expression mutants could contribute to the increased expression level from Pm.

A number of positions has previously been suggested to be the transcription start site for Pm (positions given relative to the +1 C determined in this study): +3A and +5A, the −1G and +2A, and the +2A. With a transcription start site at the C determined here, the most 3' of the C in the C-stretch of the −10 element is positioned at −13. This corroborates the proposed −10 consensus sequence for $\sigma^{32}$-dependent promoters. While $\sigma^{70}$-dependent promoters seem to be dependent on a purine for efficient transcription initiation (Lewis and Adhya, supra; Walker and Osuna, supra), several $\sigma^{32}$- and $\sigma^s$-dependent promoters have been found to initiate transcription from pyrimidines (Gross, 1996; Lacour and Landini, supra). It should be noticed that in pIB6, three positions (+6-+8) in the Pm leader region has been mutated relative to the wt Pm sequence of the TOL plasmid to introduce a BspLU11I restriction site. It cannot be ruled out that these changes affect the start site selection.

Expression from Selected Pm Mutants with Alternative Reporter Genes

It is well known that recombinant gene expression for a specific vector system varies among genes. To study the promoter activity of Pm mutants with other genes, the luc and celb genes were inserted as reporters for selected mutants (7b, 11g, 7b-2d, 7b-2g, and 7b-4g). Amounts of transcript and enzyme activities for these Pm mutants were determined relative to cells with wt Pm (pLB10 and PØY9 with celb and luc, respectively) for both reporter genes. Results for Celb and luciferase are shown in FIGS. 4B and 4C. For Celb, relative amounts of transcript and enzyme activities were comparable to what found for β-lactamase for the same mutants. For luciferase the increment in expression for Pm mutants were lower. Here, mutants from Library 2 exhibit an expression level of about 4-5 relative to wt Pm. The results obtained for celb and luc imply that high expression Pm mutants screened for high β-lactamase activity may be expected to give increased expression also for other reporter genes.

Effects of Deletion of XylS on Expression from Pm Mutants

To investigate whether the basal expression from Pm mutants was dependent on XylS, the xylS was deleted from the pIB6 constructs carrying mutants with various basal expression levels (Un3, 5d, 7b, 11g, 7b-2d), and for pIB6 (wt Pm, resulting in pB17). The basal expression in terms of ampicillin resistance on agar plates was then compared to what found for cells with the same Pm mutants in the xylS-containing pIB6. Results are shown in table 3. No changes in the ampicillin resistance were observed when xylS was deleted neither for wt Pm nor for the mutants. To distinguish the basal expression level of cells with pIB6 and pIB17 from the general ampicillin resistance for DH5α cells without β-lactamase, cells were also included with the plasmid pIBØY9 (a pIB6 derivative where bla is replaced with luc). Resistance of cells was tested on agar plates with numerous low level concentrations of ampicillin (concentrations given in Table 3). While cells with pIB6 and pIB17 were growing at 0.004 mg/ml ampicillin, cells with pØY9 tolerated only 0.001 mg/ml. Thus a low level of transcription from Pm appears to be maintained by RNA polymerase without any interactions with XylS.

The Pm mutants in the xylS-free pIB17 plasmid were further tested for induced expression in terms of ampicillin resistance on agar plates with m-toluate. Surprisingly it was found that addition of inducer resulted in increased expression, even in the absence of XylS. This yielded both the mutants and for wt Pm (pIB17). Results are shown in Table 3. To examine this phenomenon further, the ampicillin resistance was tested in a culture of cells with a plasmid without the Pm/xylS system, but with the β-lactamase gene (pBR322). Also here, an effect of addition of m-toluate was observed. Cells containing pBR322 grew on agar plates with ampicillin concentrations of 2 and 5 mg/ml in the absence and presence of 2 mM m-toluate, respectively. Thus, for the DH5α E. coli cells there appear to be a response to m-toluate, independent of the Pm/xylS system, which leads to increased ampicillin resistance. For the mutant exhibiting the highest basal expression level (Un3), the ratio between induced and basal expression level is only 2.5, and the expression level (in terms of ampicillin resistance) in the presence of m-toluate is similar in the presence and absence of XylS (See Table 3). Thus, for the Pm mutant Un3, the effect of the presence of m-toluate is probably not due to an induction of the Pm-system, but is due to some general cellular response as described above. This implies that Un3 could be a Pm mutant that functioning independent on XylS.

Effects of Increased XylS Amounts on Expression from Pm Mutants

The possibility exists that there are not sufficient amounts of XylS in the cells containing pIB6 with Pm-mutants to promote maximum expression. To examine this issue, xylS was clones with its Ps2 promoter into a plasmid with the ColE1 replicon (pIB14), and transformed this plasmid into cells containing pIB6 with Pm mutants. Thus the XylS amount in the cells should increase approximately 4-fold, since the copy numbers of pIB14 and pIB6 are approximately 15-20 and 5-6, respectively. The effects of increased XylS amounts on induced and basal expression were investigated in terms of ampicillin resistance on agar plates. Results are shown in Table 4. For comparison, the resistance levels were simultaneously determined for cells containing the Pm mutants in the pIB6 constructs without pIB14. For induced expression, the effect of increasing the XylS amount appears to be most extensive for the wt Pm construct and a mutant exhibiting a relatively low expression level (Un3). This finding was somewhat surprising because deletion of xylS did not reduce the expression compared to the expression in the presence of XylS (pIB6) from this mutant. For the mutants with the highest expression levels, the effect is less clear. For several mutants, very small colonies could be observed at high ampicillin concentrations. An explanation could be that the expression from Pm mutants reaches levels that are harmful to the cells and therefore reduces growth. For the basal expression, the effect of increased amounts of XylS appears to be largest for the constructs with the lowest basal expression level (wt, 11g, m8). This corroborates earlier studies, showing that high concentrations of XylS can activate Pm in the absence of effectors. For mutants with a high basal expression level, however, no effect was observed.

Concluding Remarks

Previously it has been shown that mutagenesis of the −10 region of the Pm promoter results in a two-fold increase in expression level (Winther-Larsen et al., 2000, supra). Here, by a cassette mutagenesis approach followed by selection for high expression mutants, mutants with more than a 5-fold increase in the expression of β-lactamase were identified. Further, by constructing a secondary mutant library based on the Pm sequence of one of the high expression mutants, a 10-fold increase in the expression from. Pm was achieved. A selection of high expression mutants was also shown to promote increased expression for other reporter genes. The nature of the mutant libraries and the high expression mutant sequences points to the importance of an appropriate strategy. The frequency of mutants reaching the highest expression levels was low in both mutant libraries. Therefore a large size of the libraries and a selective screening protocol is of crucial importance to identify the high expression mutants. All the high expression mutants exhibited a relatively large number of mutations, and mutations were distributed trough out the region that was subjected to mutagenesis. This illustrates the advantage of a random relative to a designed mutagenesis strategy. The results indicate that this is a very potent strategy for increasing the promoter activity of Pm, and it could probably be applied to other promoter systems as well.

EXAMPLE 2

Maximisation of Recombinant Gene Expression from the Pm/XylS Promoter System by Combining Promoter and UTR High Expression Mutants Materials and Methods Growth of cell cultures and DNA manipulations were performed as described below.

Bacterial Strains, Plasmids, and Growth Media

The bacterial strain and plasmids used in this study are described in Table 1. In all experiments, cells were grown in L broth (10 g/liter tryptone, 5 g/liter yeast extract, and 5 g/liter NaCl) or on L agar at 37° C., except for expression studies were 30° C. was used. Antibiotics were used at the following concentrations: kanamycin (Km), 50 µg/ml; tetracycline, 15 µg/ml. Ampicilin was used in expression studies, and concentrations are reported with the results.

DNA Manipulations

Plasmid DNA was prepared by the WizardPlus SV minipreps DNA purification kit (Promega). Transformations of E. coli were performed by use of heat shock-competent rubidium chloride-treated cells. Enzymatic manipulations were performed as described by the manufacturers. DNA was extracted from agarose gel slabs using the Qiaquick gel extraction kit (Qiagen). PCR reactions were performed using the Expand High Fidelity PCR system kit (Roche) for cloning purposes. When PCR was used for generation of templates for DNA sequencing, the polymerase DynazymeII (Finnzymes) was used. PCR templates were treated with the enzyme mixture ExoSapIt (USB) prior to DNA sequencing. Sequencing reactions were carried out using the ABI PRISM BigDye sequencing kit (Applied. Biosystems), and analyzed using an ABI 3100 Genetic Analyzer (Applied Biosystems). A down-mutation in the mRNA leader sequence of Pm previously identified by Winther-Larsen et al. (2000b) was introduced into pIB3 using two annealed, complementary oligonucleotides with the mutated Pm leader mRNA sequence and SpeI- and NdeI-compatible ends. The small DNA fragment was cloned into the SpeI/NdeI sites of pIB3 generating pIB4. Sequences of oligonucleotides were 5'-CTAGTACAATAATAATGAAGTCATGAACA-3' (SEQ ID NO. 66) and 5'-TATGTTCATGACT TCATTATTATTGTA-3' (SEQ ID NO. 67) (introduced mutations are underlined and restriction sites are shown in italics). The AflIII site upstream the Pm promoter of pIB5 was introduced by site specific mutagenesis of pIB4 using the QuikChange Site-Directed Mutagenesis Kit (Stratagene) as described by the manufacturers and the primers 5'-GCATAACCAGCATAAACGTGTCCGGTTTGATAG (SEQ ID NO. 68) and 5'-CGATAACCAGCATAAA CGTGTCCGGTTTGATAG (SEQ ID NO. 69). The BspLU11I site of pIB6 was introduced by site specific mutagenesis of the SpeI site of pIB5 using the primers 5'-CTTAGGCTTTATGCAAC ATGTACAATAATAATGAAGTCATG-3' (SEQ ID NO. 70) and 5'-CATGACTTCATTATTATTGTAC ATGTTGCATAAAGCCTAAG-3' (SEQ ID NO. 71). Cloning of the xylS gene from pIB6 into pPK34 to generate pIB14 was done by PCR amplification with the primers 5'-AACCGAGAATTCGCCGTTGGATAGCTCCGCTAC-3' (SEQ ID NO. 72) and 5'-AATGCATTGGTTCTGCAG-GAGAGTGTCTAAGAAAGCCGG-3' (SEQ ID NO. 73) which introduced the restriction sites for EcoRI and PstI, respectively, for cloning purposes.

For expression studies, cell cultures were added m-toluate to 0.1 mM for induction of Pm. A high expression promoter mutant identified, Pm-7b4g, was selected for combination with UTR mutants. A mutant library (Library Pm-7b4g-UTR) was constructed by a strategy where mutations were introduced using synthetic oligonucleotides (5'-TATGT-TCATGACTCCATTATTATTGTA-3' (SEQ ID NO. 74) and 5'-CATGT12114114411433134214311CA-3' (SEQ ID NO. 75) where the numbers indicate the doping number of the nucleotides; 1=79% A, 7% C, 7% G, 7% T; 2=7% A, 79% C, 7% G, 7% T; 3=7% A, 7% C, 79% G, 7% T; 4=7% A, 7% C, 7% G, 79% T). A detailed protocol is given in Bakke et al (ref). The annealed oligonucleotides were cloned into the BspLU11I/NdeI-digested construct pIB18. pIB18 is identical to pIB11 (see Berg et al. (ref)), but the wt Pm sequence has been exchanged by the high expression Pm mutant Pm-7b4g. In this construct the β-lactamase gene (bla) is used as a reporter for Pm. High expression mutants were identified and DNA sequences determined as described in Bakke et al. (ref). Ampicillin resistances, β-lactamase activities, and relative quantities of β-lactamase transcript all reflect Pm activity, and were determined as described in Bakke et al. (ref).

Primers used for PCR and DNA sequencing were identical to those given in Bakke et al. (ref). The following primers were used for real time PCR experiments: ACGTTTTC-CAATGATGAGCACTT (SEQ ID NO. 76) and TGCCCG-GCGTCAACAC (SEQ ID NO. 77) for the β-lactamase gene, and TACCTTTGCCATGTTTCAGAAACA (SEQ ID NO. 78) and ATCAGGTGCGACAATCTATCGA (SEQ ID NO. 79) for the kanamycin gene (used as a normalizer).

For construction of a transposon insertion mutant we used the high expression UTR mutant A3 (identified in this study) in the pIB18 construct (containing the high expression Pm mutant Pm-7b4g); pIB18-UTR-A3, and inserted a NotI linker in the blunted Acc665 site downstream bla, resulting in pIB19. The NotI/NcoI fragment of pIB19 (containing the mutated Pm, UTR, bla, and parts of xylS) was exchanged with the NotI/NcoI fragment of the transposon insertion suicide vector pKD20 (Bakkevig et al., 2005), resulting in pIB20. When transformed into E. coli DH5α, this vector allows for transposition insertion of the high expression Pm/UTR system (a fragment encompassing the Pm 7b4g and UTR A3 mutations, the xylS and bla genes) into the chromosome.

Results

An UTR mutant library (Library Pm-7b4g-UTR) was successfully produced in a vector containing the high expression Pm mutant Pm-7b4g (for sequence of the Pm region, see FIG. 6a). The size of the mutant library was estimated to 800 000. UTR sequences were determined for candidates growing at high ampicillin concentrations on agar medium with m-toluate. For selected mutants plasmids were isolated and transformed into E. coli DH5α. This was done to ensure that the elevated ampicillin resistance resulted from mutations introduced in the UTR, not spontaneous mutations elsewhere in the genome. After reintroduction, ampicillin resistances were determined after growth in microtiter plates as described in Bakke et al. (in prep.). DNA sequences for the UTR as well as ampicillin resistance data are given in FIG. 6b. While cells with pIB18 (Pm 7b4g, wt UTR) grew to approximately 0.5 mg/ml amp, cells with the UTR mutant constructs grew up to 13 mg/ml ampicillin.

The expression from Pm was further studied for seven candidates exhibiting high ampicillin resistances (UTR-A3, UTR-C2, UTR-F2, UTR-F3, UTR-G2, UTR-G3, UTR-H3, see FIG. 6b). Relative amounts of β-lactamase transcript were determined by a reverse transcriptase/real time PCR strategy. The expression levels for the same mutants were also investigated by determining β-lactamase activities. The construct pIB11 (wt Pm, wt UTR) was used as the calibrator in the relative quantifications. For both the real time PCR quantifications and the enzyme assays the experiments were repeated twice for samples obtained from independently grown cell cultures. The results are shown in FIG. 7. The β-lactamase activities showed an approximately 60 fold increment for the UTR mutants (with Pm-7b4g in pIB18) when compared to the expression from the wt system in pIB11. The relative transcript amounts showed an even larger increase in expression; the β-lactamase transcript amounts were found to be around 90 times increased for the UTR mutants (in the pIB18 background) relative to the level in cells with pIB11.

For one of the mutants identified here; pIB18-UTR-A3, both real time PCR experiments and β-lactamase assays indicated high expression levels (approximately 85 and 65 times the expression from the wt system in pIB11, respectively). This mutant was chosen for the construction of an insertion mutant. A fragment encompassing the mutated Pm and UTR region, the xylS and bla genes was transformed into E. coli DH5α cells via a transposon insertion suicide vector (see Material and Methods). The resultant transformants should represent plasmid-free insertion mutants. Candidates were subjected to tests for ampicillin resistance, and were further examined for content of plasmid. One of the candidates that exhibited increased ampicillin resistance when induced with m-toluate, appeared to be plasmid-free. The ampicillin resistance data for this potential insertion mutant is given in Table 1. The results indicate that the chromosome-integrated high-expression Pm-mutant expresses the reporter β-lactamase at considerable higher levels than the plasmid born wt Pm system in pIB11 (see Table 5), which is present with approximately 5-6 copies per cell.

The ampicillin resistance for cells with pIB6-Pm-7b4g is about 4.5 mg/ml on agar plates with 2 mM m-toluate. The same induced ampicillin resistance level was found for cells with another high expression Pm mutant construct; pIB6-7b2g. However, for the latter mutant, the basal expression level was found to be lower (0.065 mg/ml ampicillin for pIB6-Pm7b2g, and 1 mg/ml ampicillin for pIB6-Pm-7b4g). To test whether the basal expression level could be lowered without reducing the induced expression level, the Pm-7b4g was exchanged with Pm-7b2g in the UTR A3-bearing construct pIB19 (see Materials and Methods). It was found that the basal expression in terms of ampicillin resistance was reduced from 0.5 to 0.3 mg/ml, while the induced expression level appears to be unchanged (see Table 5). This was not obvious, since the UTR A3 mutant had been selected for in combination with Pm-7b4g. Probably, the Pm-7b2g/UTR A3 mutant could be used for obtaining an insertion mutant with lower basal expression level.

TABLE 1

Bacterial strains and plasmids

| Bacterial strain or plasmid | Properties* | Source of reference |
|---|---|---|
| E. coli DH5α | EndA1, hsdR17, supE44, thi-1, λ, recA1, gyrA96, relA1, ΔlacU169 (φ80dlacZΔM15) | Bethesda Research Laboratories |
| pJT19bla | RK2-based expression vector containing the Pm promoter with the gene encoding the regulatory protein XylS and bla as a reporter gene for Pm and. Km$^r$. 8.1 kb. | Winther-Larsen et al, Metab. Eng., 2, 92-103, 2000. |
| pLITMUS28 | General cloning vector. | New England Biolabs |
| pJB785TT | Expression vector | Santos et al, FEMS Microbiol Lett, 195(1): 91-96, 2001 |
| pHE155 | Derivate of pLITMUS28. Contains BglII-EcoRI insert from pJB785TT. | Ertesvåg (unpublished) |
| pHE156 | Derivate of pHE155 with EcoRI removed. | Ertesvåg (unpublished) |
| pHE158 | Derivate of pHE156 with SalI-linker in BglII. | Ertesvåg (unpublished) |
| pJB658 | RK2-based expression vector containing the Pm promoter and the gene encoding the regulatory protein XylS. Km$^r$. 7.1 kb. | Blatny et al., Plasmid, 38, 35-51, 1997. |
| pIB1 | A pJB658 derivate in which a XhoI-linker was introduced in the bluntet AgeI site. Ap$^r$. 6.8 kb. | This study |
| pIB2 | The SalI/PstI fragment from pHE158 containing the rrnBT1T2 transcription terminator was cloned into the XhoI/NsiI sites of pIB1. Ap$^r$. 6.6 kb. | This study |
| pIB3 | The XbaI/MunI fragment containing rrnBT1T2 was cloned into the same sites of pJT19bla. Km$^r$. 8.1 kb. | This study |
| pIB4 | A pIB3 derivative with a translational down-mutation in the Pm mRNA leader sequence. Km$^r$. 8.1 kb. | This study |
| pIB5 | An AflIII site was introduced in pIB4 upstream upstream the Pm promoter by site specific mutagenesis. Km$^r$. 8.1 kb. | This study |
| pIB6 | The SpeI site downstream the Pm promoter of pIB5 was changed to a BspLU11I site by site specific mutagenesis. Km$^r$. 8.1 kb. | This study |
| pJT19luc | RK2-based expression vector containing the Pm promoter with the gene encoding the regulatory protein XylS and lucas a reporter gene for Pm and. Km$^r$. 8.1 kb. | Winther-Larsen et al (2000), supra. |
| pØY9 | A pIB6 derivative where the NdeI/BamHI fragment containing bla was substituted with NdeI/BamHI fragment containing luc from pJT19luc. Km$^r$. 8.? kb. | This study |
| pJB658CelB | Derivative of pJB658 with celB cloned in the NdeI site downstream Pm. Km$^r$. 8.7 kb. | Blatny et al. (1997), supra. |
| pLB10 | A pIB6 derivative where the NdeI/BamHI fragment containing bla was substituted with the NdeI/BamHI fragment containing celB from pJB658CelB. Km$^r$. 8. kb. | This study |

TABLE 1-continued

Bacterial strains and plasmids

| Bacterial strain or plasmid | Properties* | Source of reference |
|---|---|---|
| pBR322 | Plasmid with rep replicon. Ap$^r$. 4.4 kb. | Bolivar et al., Gene, 2(2), 75-93, 1977. |
| pPK34 | Plasmid with ColE1 replicon. Tc$^r$. | Haugan et al, 1992, J. Bacteriol., 174, 7026-32 |
| pIB14 | Derivative of pPK34 containing xylS and its promoter. A PCR fragment containing the xylS gene from pIB6 was cloned into the EcoRI/PstI sites of pPK34. Tc$^r$. 5.1 kb. | This study |
| pIB17 | A derivative of pIB6 where xylS was deleted by BglII/DraIII digestion, filled in and religated. Km$^r$. 6.4 kb. | This study |

*Ap$^r$, ampicillin resistance; Km$^r$, kanamycin resistance; Tc$^r$, testracyclin resistance

TABLE 2

Primers used for Real-Time PCR.

| Target gene | Sequence | |
|---|---|---|
| bla | 5'-TGGATCTCAACAGCGGTAAG-3' | (SEQ ID NO. 80) |
| bla | 5'-GGCAGCACTGCATAATTCTCT-3' | (SEQ ID NO. 81) |
| luc | 5'-TGGAGAGCAACTGCATAAGG-3' | (SEQ ID NO. 82) |
| luc | 5'-CGCAACTGCAACTCCGATAA-3' | (SEQ ID NO. 83) |
| celb | 5'-CGCTGACCACCAGCTTCAAT-3' | (SEQ ID NO. 84) |
| celb | 5'-TGCTGCGGTCACGGTTATAG-3' | (SEQ ID NO. 85) |
| km | 5'-GCAATCAGGTGCGACAATCT-3' | (SEQ ID NO. 86) |
| km | 5'-TCGCAGTGGTGAGTAACCAT-3' | (SEQ ID NO. 87) |

TABLE 3

Ampicillin resistance on agar plates in the presence and absence of m-toluate for cells with the plasmid pIB17 (ΔXylS) with Pm mutants compared to cells with pIB6 with Pm mutants.

| Mutant | amp. res. (mg/ml)** ÷ m-toluate (pIB6) | amp. res. (mg/ml)** ÷ m-toluate ΔXylS (pIB17) | amp. res. (mg/ml)* + m-toluate (pIB6) | amp. res. (mg/ml)* + m-toluate ΔXylS (pIB17) |
|---|---|---|---|---|
| Pm wt | 0.004 | 0.004 | 0.5 | 0.01 |
| Un3 | 1.0 | 1.0 | 2.5 | 2.5 |
| 5d | 0.8 | 0.8 | 3.0 | 2.0 |
| 7b | 0.03 | 0.03 | 3.5 | 0.15 |
| 11g | 0.015 | 0.015 | 3.0 | 0.065 |
| 7b-2d | 0.2 | 0.2 | 4.0 | 0.7 |

*Ampicillin concentrations tested (mg/ml): 0.01-0.015-0.03-0.065-0.1-0.15-0.2-0.5-0.6-0.7-0.8-0.9-1.0-1.5-2.0-2.5-3.0-3.5-4.0-4.5-5.0
**Ampicillin concentrations tested (mg/ml): 0.001-0.002-0.003-0.004-0.005-0.015-0.03-0.065-0.1-0.15-0.2-0.3-0.4-0.5-0.6-0.7-0.8-0.9-1.0-1.1-1.2

TABLE 4

Ampicillin resistance for Pm wt and mutants with increased XylS amounts

| Mutant | amp. res. (mg/ml)** ÷ m-toluate (pIB6) | amp. res. (mg/ml)** + m-toluate + XylS (pIB14) | amp. res. (mg/ml)* ÷ m-toluate (pIB6) | amp. res. (mg/ml)* ÷ m-toluate + XylS (pIB14) |
|---|---|---|---|---|
| Pm wt | 0.5 | 2.5 | 0.0025 | 0.03 |
| Un3 | 2.5 | 5.0 | 1.0 | 1.0 |
| 3g | 3.5 | 3.5 | 0.15 | 0.2 |

TABLE 4-continued

Ampicillin resistance for Pm wt and mutants with increased XylS amounts

| Mutant | amp. res. (mg/ml)** ÷ m-toluate (pIB6) | amp. res. (mg/ml)** + m-toluate + XylS (pIB14) | amp. res. (mg/ml)* ÷ m-toluate (pIB6) | amp. res. (mg/ml)* ÷ m-toluate + XylS (pIB14) |
|---|---|---|---|---|
| 5d | 3.0 | 4.5$^1$ | 0.8 | 0.8 |
| 7b | 3.5 | 3.5$^1$ | 0.03 | 0.1 |
| 11g | 3.5 | 3.5$^1$ | 0.015 | 0.065 |
| m5 | 3.0 | 3.5 | 0.065 | 0.1 |
| m8 | 2.5 | 4.5$^1$ | 0.015 | 0.065 |
| 7b-2d | 4.5 | 4.5$^1$ | 0.2 | 0.3 |
| 7b-2g | 4.5 | 4.5$^1$ | 0.065 | 0.15 |
| 7b-4g | 4.5 | 4.5$^1$ | 0.1 | 0.2 |

*Ampicillin concentrations (mg/ml) tested: 0.0025-0.005-0.015-0.03-0.065-0.1-0.15-0.2-0.3-0.4-0.5-0.6-0.7-0.8-0.9-1-1.5-2-2.5
**Ampicillin concentrations (mg/ml) tested: 0.5-1-2-2.5-3-3.5-4-4.5-5-5.5
$^1$Very small colonies (indicating poor growth) could be observed on higher ampicillin concentrations

TABLE 5

Ampicillin resistances on agar plates for constructs with high expression Pm and UTR mutants used in this study

| Construct | Amp. res. mg/ml* + m-toluate (2 mM) | Amp. res. mg/ml** ÷ m-toluate |
|---|---|---|
| pIB11-Pm-7b4g (wt UTR) | 2 | not growing at 0.03 mg/ml |
| pIB19 (Pm-7b4g/UTR-A3) | 14 | 0.5 |
| pIB19-Pm-7b2g (UTR-A3) | 14 | 0.3 |
| Insertion mutant (Pm-7b4g/UTR-A3) | 2 | 0.065 |
| pIB11 (wt Pm/wt UTR)*** | 0.5 | <0.005 |

*Ampicillin concentrations (mg/ml) tested: 2-3-4-5-6-8-10-12-14
**Ampicillin concentrations (mg/ml) tested: 0.03-0.065-0.1-0.15-0.2-0.3-0.5-0.75-1.0-1.5-2
***Resistance data for pIB11 was obtained in a separate experiment

TABLE 6

| SEQ ID No. | Sequence of the Pm 5' translated transcript region$^6$ |
|---|---|
| 1 | aactagtaca ataataatgg agtcatgaac atatg |
| 2 | aactagtata acactaatgg agccatgaac atatg |
| 3 | acatagtaca ttaatattgg agtcatgaac atatg |
| 4 | acattgtact ataatgatgg agtcatgaac atatg |

TABLE 6-continued

| SEQ ID No. | Sequence of the Pm 5' translated transcript region[6] |
|---|---|
| 5 | atatagtaca acaatactgg agtcatgaac atatg |
| 6 | atatactaca acattaatgg agtcatgaac atatg |
| 7 | aaattgtacc ataatactgg agtcatgaac atatg |
| 8 | atctagtata acataaatgg agtcatgaac atatg |
| 9 | acatagtaca atattaatgg agtcatgaac atatg |
| 10 | atctagtgta acataaatgg agtcatgaac atatg |
| 11 | aaatagtacc acactaatgg agtcatgaac atatg |
| 12 | aaatagtaca ctactaatgg agtaatgaac atatg |
| 13 | aacatgtaca ataataatgg agtcatgaac atatg |
| 14 | aacatgtacc ataataaagg agtcttgaac atatg |
| 15 | aacatgtacc ataataatgg agttttgaac atatg |
| 16 | aacatgtacc atattaatgg agtcttgaac atatg |
| 17 | aacatgtacc ataataatgg agtaatgaac atatg |
| 18 | aacatgtcaa acactaatgg agtaatgaac atatg |
| 19 | aacatgtaac ataataatgg agtcttgaac atatg |
| 20 | aacatgtaac ataatactgg agtaatgaac atatg |
| 21 | aacatgtacc acaataatgg agtcttgaac atatg |
| 22 | aacatgtaca atcatacagg agtcatcaac atatg |
| 23 | aacatgtacc acaataatgg agttttgaac atatg |
| 24 | aacatgttac acaataatgg agtaatgaac atatg |
| 25 | aacatgtcca ataataatgg agtataacat atg |
| 26 | aacatgtccc attatactgg agtcttgaac atatg |
| 27 | aacatgtacc ataataatgg agtcctgaac atatg |
| 28 | aacatgtacc atattaatgg agttatgaac atatg |
| 29 | aacatgtacc ataataatgg agtcttgaac atatg |
| 30 | aacatgtact ataataatcg aggtcatgaa catatg |
| 31 | aacatgttac aataattttg gagccatgaa catatg |
| 32 | aacatgtaca ataatacacg agtcatgaac atatg |
| 33 | aacatgtcca agtatacagg agtcatgaac atatg |
| 34 | aacatgtacc attataacgg agtaatgaac atatg |
| 35 | aacatgtacc ataatacagg agttatgaac atatg |
| 36 | aacatgtaca ataatacagg aacaatgaac atatg |
| 37 | aacatgtaca atcataccag agtaatgcca atatg |

EXAMPLE 3

The Use of XylS Mutant Genes Alone and in Combination with Pm- and/or UTR-Mutations to Achieve Increased Expression of Heterologous Genes Methods and Materials
Plasmid Constructions The plasmid pTA30, parental plasmid of the screening vector pTA13, was constructed by generating two new restriction sites, SacI and AgeI in pJT19bla (Winther-Larsen et al, *Metab. Eng.* 2: 92-103 (2000)) with the use of the primers SacI-F and SacI-R and AgeI-F and AgeI-R, respectively. pTA4 was constructed by cloning a SacI-AgeI fragment from pTA30 into pLITMUS28. pTA5 was constructed by removing an internal NcoI site in xylS from pTA4 with the primers F-NcoI rem and R-NcoI rem. pTA6 was constructed by generating two new restriction sites, NcoI and AvrII in pTA5 with the primers F-NcoI+ and R-NcoI+ and F-AvrII+ and R-AvrII+. The screening vector pTA13 was constructed by cloning an AgeI-SacI fragment from pTA6 into pTA30.

All plasmids used in this study are presented in Table 7. All primers used in this study is presented in Table 8.

TABLE 7

| Plasmids used in the study | | |
|---|---|---|
| Plasmid | Description | Reference or source |
| LITMUS 28 | Cloning vector. | New England Biolabs |
| pJT19bla | Expression vector | Winther-Larsen 2000 |
| pTA3 | Derivate of pLITMUS28 with an XbaI-NcoI fragment from pJT19blaE. | This study |
| pTA3S | Derivate of pTA3 with new SacI site upstream of xylS generated with the primers SacI-F and SacI-R. | This study |
| pTA2 | Derivate of pLitmus28 with NcoI and XhoI fragment from pJT19blaE. | This study |
| pTA2A | Derivate of pTA2 with new AgeI site downstream of xylS generated with the primers AgeI-F and AgeI-R. | This study |
| pTA30 | Derivate of pJT19bla with an XbaI-NcoI fragment from pTA3S and an NcoI-XhoI fragment from pTA2A. | This study. |
| pTA4 | Derivate of pLitmus28 with an AgeI-SacI fragment from pTA30. | This study |
| pTA5 | Derivate of pTA4 but with a NcoI site, internal to xylS, removed with the primers F-NcoI rem and R-NcoI rem. | This study |

TABLE 7-continued

Plasmids used in the study

| Plasmid | Description | Reference or source |
|---|---|---|
| pTA6 | Derivate of pTA5 with a new NcoI site at xylS start-ATG created with the primers F-NcoI+ and R-NcoI+, and a new AvrII site immediately downstream of xylS created with the primers F-AvrII+ and R-AvrII+. | This study |
| pTA13 | Derivate of pTA30 with an AgeI-SacI-fragment from pTA6. | This study. |

TABLE 8

Primers used in the study

| Primer name | Sequence | |
|---|---|---|
| SacI-F | 5'-CTCTTATTTTAATGTGAGCTCGTTGGTGTG-3' | (SEQ ID NO. 88) |
| SacI-R | 5'-CTACATCACAGCAAGGAGCTCACATTAAAATAAG-3' | (SEQ ID NO. 89) |
| AgeI-R | 5'-GCCGAAGAAGGGACCGGTTGGCATCGC-3' | (SEQ ID NO. 90) |
| AgeI-F | 5'-GCGATGCCAACCGGTCCCTTCTTCGGC-3' | (SEQ ID NO. 91) |
| F-epP2 xylS | 5'-CCACGAAGCTTCCCATGGTGACG-3' | (SEQ ID NO. 92) |
| R-epP2 xylS | 5'-GGCCTTGACTAGAGGGTACCAGAG-3' | (SEQ ID NO. 93) |
| F-AvrII + | 5'-GATTACGAACCTAGGCGAAGAAGGG-3' | (SEQ ID NO. 94) |
| R-AvrII + | 5'-CCCTTCTTCGCCTAGGTTCGTAATC-3' | (SEQ ID NO. 95) |
| F-NcoI + | 5'-GAACCGTGAACCATGGATTTTTGC-3' | (SEQ ID NO. 96) |
| R-NcoI + | 5'-GCAAAAATCCATGGTTCACGGTTC-3' | (SEQ ID NO. 97) |
| F-NcoI rem.a | 5'-GTGCTCCTGGGCATGGCCACG-3' | (SEQ ID NO. 98) |
| R-NcoI rem.a | 5'-CGTGGCCATGCCCAGGAGCAC-3' | (SEQ ID NO. 99) |

<sup>a</sup>This primer set, which were used to remove an intrinsic NcoI site from xylS, accidentally caused a glycine to alanine mutation in residue 92 in XylS.

Error-Prone PCR

Error-prone PCR was done according to Matsumura and Ellington (Matsumura, I. & Ellington, A. D. Mutagenic PCR of protein-coding genes for in vitro evolution, Vol. 182, Edn. 2 (Humana Press Inc., 2001) with the primers F-epP2 xylS and R-epP2 xylS and pTA6 as the template. To create a library with varying mutation frequencies, $Mn^{2+}$ concentrations between 0.0312 and 0.500 mM were used. The PCR program used the following steps: (1) 94° C. for two minutes, (2) 94° C. for 30 seconds, (3) 55° C. for 30 seconds, (4) 72° C. for one minute, (5) repeat step 2 to 4 25 times, (6) 72° C. for seven minutes. The correct PCR fragments were identified on a 0.8% agarose gel, excised and then purified with the QiaQuik kit (Qiagen), before digestion with NcoI and AgeI and subsequent cloning into pTA13. The pTA13 screening vectors containing the xylS mutant library were then transformed into E. coli DH5α cells, creating a cell library.

Screening for XylS Mutants—β-Lactamase Assay

To screen the cell library for cells expressing novel XylS mutants the cell library was cultured for 18 hours and then transferred to plates containing 1.0 mM m-toluic acid or no m-toluic acid, kanamycin, and selective concentrations of ampicillin. This took advantage of the fact that in pTA13 the bla gene is under control of the Pm promoter which is positively regulated by XylS. Higher expression from Pm leads to more β-lactamase production in a linear relationship within the ampicillin concentrations used in this study. Colonies with cells exhibiting altered ampicillin tolerance were then picked and transferred to 96 well plates with 100 μl LB broth and kanamycin, grown at 30° C. for 18 h, diluted, and then replica plated onto agar plates containing either 1 mM m-toluic acid or no m-toluic, kanamycin and selective ampicillin concentrations to establish the tolerance levels. The tolerance level was set to the mean value of the highest observed ampicillin concentration tolerated and the lowest observed ampicillin concentration that didn't allow growth.

xylS genes from cells that consistently showed altered tolerance levels to ampicillin after replica plating were then re-cloned into fresh background plasmids and re-transformed into fresh cells to eliminate secondary-site effects. The mutants were then screened again to verify the observed tolerance levels.

Staggered Extension Process DNA Shuffling

Staggered extension process (StEP) DNA shuffling was performed as described by Stemmer (Proc. Natl. Acad. Sci. USA 91: 10747-10751, 1994). The template for StEP was a set of mutant xylS genes containing mutants discovered after error-prone PCR and after rational combination of single mutations. The primers that were used were Inner-fw-xylS and Inner-rv-xylS: The PCR program used the following steps: (1) 96° C. two minutes, (2) 95° C. for 30 seconds, (3) 50° C. for two minutes, (4) repeat step 2 and 3 160 times, (5)

50° C. for two minutes. The obtained DNA shuffling products were excised from gel, purified with QiaQuik (Qiagen) and digested with NcoI and AgeI before cloning into pTA13.

Results

The results show that mutations made in XylS which increase transcription from Pm in the presence of effector. Thus, as can be seen from FIG. 8 *a*) transcription of the bla gene, with subsequent increased ampicillin tolerance, increases with mutated XylS genes comprising single point mutations. The resulting XylS mutants thus have an increased ability to stimulate transcription from Pm. FIG. 9 and Table 9 present various mutated XylS proteins containing different substitutions, obtained either by error prone PCR and rational combination of single mutations (designated Syn 1-18) or staggered extension process DNA shuffling (designated StEP 1-13) and indicates ampicillin tolerance in the presence or absence of effectors. Such mutants have combinations of the mutations shown in FIG. 8 and also have an increased ability to stimulate transcription from Pm.

TABLE 9

XylS mutant proteins with genotype and phenotype

| Name | Genotype | +[a] | −[b] |
|---|---|---|---|
| Syn-1 | I50T, F97L | 1950 ± 50 | 35 ± 5 |
| Syn-2 | I50T, H85R | 1950 ± 50 | 35 ± 5 |
| Syn-3 | F3Y, I50T, H85R | 1950 ± 50 | 35 ± 5 |
| Syn-4 | K38E, I50T, H85R | 1950 ± 50 | 35 ± 5 |
| Syn-5 | N7S, I50T, H85R | 2100 ± 100 | 35 ± 5 |
| Syn-6 | K38E, I50T, F97L | 1850 ± 50 | 35 ± 5 |
| Syn-7 | N7S, I50T, F97L | 1550 ± 50 | 35 ± 5 |
| Syn-8 | R45T, I50T, H85R | 1950 ± 50 | 35 ± 5 |
| Syn-9 | R45T, I50T, F97L | 1950 ± 50 | 35 ± 5 |
| Syn-10 | F3Y, G166E | 1950 ± 50 | 45 ± 5 |
| Syn-11 | I50V, H174R | 2700 ± 100 | 35 ± 5 |
| Syn-12 | E195G, M196T | 2300 ± 100 | 35 ± 5 |
| Syn-13 | I50T, A111V | 2700 ± 100 | 85 ± 5 |

TABLE 9-continued

XylS mutant proteins with genotype and phenotype

| Name | Genotype | +[a] | −[b] |
|---|---|---|---|
| Syn-14 | I50T, F97L, G198D | 2700 ± 100 | 45 ± 5 |
| Syn-15 | F3Y, I50T, F97L | 3500 ± 100 | 55 ± 5 |
| Syn-16 | N7T, I50T, F97L | 2500 ± 100 | 55 ± 5 |
| Syn-17 | N7T, I50T, H85R | 2100 ± 50 | 55 ± 5 |
| Syn-18 | I50T, H85R, G198D | 2700 ± 100 | 55 ± 5 |
| StEP-2 | I50T, F97L, E195G, M196T | 2500 ± 500 | 30 ± 10 |
| StEP-3 | I50T, H85R, G198D | 2500 ± 500 | 50 ± 10 |
| StEP-5 | F3Y, I50T, G198D | 4100 ± 100 | 55 ± 5 |
| StEP-6 | F3Y, G166E, E195G, M196T | 4300 ± 100 | 55 ± 5 |
| StEP-7 | F3Y, I50T, F97L, G198D | 4300 ± 100 | 55 ± 5 |
| StEP-8 | F3Y, I50T, F97L, G166E, G198D | 4300 ± 100 | 85 ± 5 |
| StEP-9 | I50T, H174R, G198D | 3300 ± 100 | 75 ± 5 |
| StEP-10 | F3Y, I50T, A111V | 4700 ± 100 | 230 ± 10 |
| StEP-11 | F3Y, I50T, G166E, G198D | 5500 ± 100 | 110 ± 10 |
| StEP-12 | F3Y, I50T, A111V, G198D | 5500 ± 100 | 430 ± 10 |
| StEP-13 | F3Y, I50T, F97L, E195G, M196T | 5500 ± 100 | 150 ± 10 |

[a]+ denotes the induced ampicillin tolerance of the host cell
[b]− denotes the basal ampicillin tolerance of the host cell.
In addition to those listed, Syn-11 contained the Y96C mutation which was unintentionally introduced.)

It has further been shown that that it is possible to get an additive effect when combining XylS mutants with either Pm mutants or leader mutants (Table 10)

TABLE 10

Wild type xylS and xylS-syn16 in combination with different Pm and UTR mutants

|  | wild type Pm and UTR | wild type Pm and a3-UTR | 7b4g and wild type UTR |
|---|---|---|---|
| wild type xylS | 1 | 8 ± 2 | 13 ± 0 |
| xylS-syn16 | 5 ± 0 | 10 ± 0 | 17 ± 1 |

(the values are from a β-lactamase assay with 0.1 mM m-toluic acid as inducer and in relative values to a construct where all elements were wild type (native)).

The invention claimed is:

1. A method of producing a desired gene product in a recombinant gene expression system wherein transcript production from said gene is increased and results in enhanced expression of the desired gene product, said method comprising expressing said gene with a Pm promoter-based expression system using:
   (i) a mutant Pm promoter which increases the amount of transcript produced and enhances gene expression compared to gene expression obtained using the corresponding unmutated Pm promoter, wherein said mutant Pm promoter comprises a sequence selected from the group consisting of SEQ ID NOS: 102 to 119, 121 to 137 and 144 to 145, and
   (ii) a mutant Pm mRNA leader which increases the amount of transcript produced and enhances gene expression compared to gene expression obtained using the corresponding unmutated Pm mRNA leader, wherein said mutant Pm mRNA leader comprises a sequence selected from the group consisting of SEQ ID NOS: 2 to 12, 14 to 37 and 147 to 163,
   wherein said mutant Pm promoter and mutant Pm mRNA leader enhance gene expression compared to gene expression obtained using only the mutant Pm promoter and compared to gene expression obtained using only the mutant Pm mRNA leader.

2. The method of claim 1, wherein said method further comprises using a mutant XylS which comprises one or more mutations which enhance gene expression compared to gene expression obtained using the corresponding unmutated XylS, wherein said mutant XylS comprises a genotype selected from the group consisting of:
i) I50T, F97L;
ii) I50T, H85R;
iii) F3Y, I50T, H85R;
iv) K38E, I50T, H85R;
v) N7S, I50T, H85R;
vi) K38E, I50T, F97L;
vii) N7S, I50T, F97L;
viii) R45T, I50T, H85R;
ix) R45T, I50T, F97L;
x) F3Y, G166E;
xi) 150V, H174R, Y96C;
xii) E195G, M196T;
xiii) I50T, A111V;
xiv) I50T, F97L, G198D;
xv) F3Y, I50T, F97L;
xvi) N7T, I50T, F97L;
xvii) N7T, I50T, H85R;
xviii) I50T, H85R, G198D;
xix) I50T, F97L, E195G, M196T;
xx) I50T, H85R, G198D;
xxi) FY3, I50T, G198D;
xxii) F3Y, G166E, E195G, M196T;
xxiii) F3Y, I50T, F97L, G198D;
xxiv) F3Y, I50T, F97L, G166E, G198D;
xxv) I50T, H174R, G198D;
xxvi) F3Y, I50T, A111V;
xxvii) F3Y, I50T, G166E, G198D;
xxviii) F3Y, I50T, A111V, G198D; and
xxix) F3Y, I50T, F97L, E195G, M196T.

3. A method of enhancing expression of a desired gene product wherein transcript production from the gene is increased and results in enhanced expression of the desired gene product and wherein said gene product is expressed from a Pm promoter, said method comprising:
a) introducing mutations into a Pm promoter to provide a mutant Pm promoter which increases the amount of transcript produced and enhances gene expression compared to gene expression obtained using the corresponding unmutated Pm promoter and which comprises a sequence selected from the group consisting of SEQ ID NOS: 102 to 119, 121 to 137 and 144 to 145;
b) introducing mutations into DNA corresponding to the Pm mRNA leader to provide a mutant Pm mRNA leader which increases the amount of transcript produced and enhances gene expression compared to gene expression obtained using the corresponding unmutated Pm mRNA leader and which comprises a sequence selected from the group consisting of SEQ ID NOS: 2 to 12, 14 to 37 and 147 to 163;
c) optionally introducing mutations into a DNA sequence encoding XylS to provide mutant XylS comprising a genotype selected from the group consisting of:
i) I50T, F97L;
ii) I50T, H85R;
iii) F3Y, I50T, H85R;
iv) K38E, I50T, H85R;
v) N7S, I50T, H85R;
vi) K38E, I50T, F97L;
vii) N7S, I50T, F97L;
viii) R45T, I50T, H85R;
ix) R45T, I50T, F97L;
x) F3Y, G166E;
xi) 150V, H174R, Y96C;
xii) E195G, M196T;
xiii) I50T, A111V;
xiv) I50T, F97L, G198D;
xv) F3Y, I50T, F97L;
xvi) N7T, I50T, F97L;
xvii) N7T, I50T, H85R;
xviii) I50T, H85R, G198D;
xix) I50T, F97L, E195G, M196T;
xx) I50T, H85R, G198D;
xxi) FY3, I50T, G198D;
xxii) F3Y, G166E, E195G, M196T;
xxiii) F3Y, I50T, F97L, G198D;
xxiv) F3Y, I50T, F97L, G166E, G198D;
xxv) I50T, H174R, G198D;
xxvi) F3Y, I50T, A111V;
xxvii) F3Y, I50T, G166E, G198D;
xxviii) F3Y, I50T, A111V, G198D; and
xxix) F3Y, I50T, F97L, E195G, M196T;
d) selecting a mutant Pm promoter and mutant Pm mRNA leader combination, or optionally a mutant Pm promoter, mutant Pm mRNA leader and mutant XylS combination, which increases the amount of transcript produced and enhances expression of the desired gene product compared to gene expression obtained using the corresponding unmutated Pm promoter and unmutated Pm mRNA leader, and optionally unmutated XylS; and
e) expressing said gene using the mutant combination.

4. An isolated nucleic acid molecule comprising:
(i) a mutant Pm promoter which increases the amount of transcript produced and enhances gene expression compared to gene expression obtained using the corresponding unmutated Pm mRNA leader and which comprises a sequence selected from the group consisting of SEQ ID NOS: 102 to 119, 121 to 137 and 144 to 145; and
(ii) a region corresponding to a mutant Pm mRNA leader sequence which increases the amount of transcript produced and enhances gene expression compared to gene expression obtained using the corresponding unmutated Pm mRNA leader and which comprises a sequence selected from the group consisting of SEQ ID NOS: 2 to 12, 14 to 37 and 147 to 163; and
(iii) optionally a DNA sequence encoding a mutant XylS comprising a genotype selected from the group consisting of:
i) I50T, F97L;
ii) I50T, H85R;
iii) F3Y, I50T, H85R;
iv) K38E, I50T, H85R;
v) N7S, I50T, H85R;
vi) K38E, I50T, F97L;
vii) N7S, I50T, F97L;
viii) R45T, I50T, H85R;
ix) R45T, I50T, F97L;
x) F3Y, G166E;
xi) 150V, H174R, Y96C;
xii) E195G, M196T;
xiii) I50T, A111V;
xiv) I50T, F97L, G198D;
xv) F3Y, I50T, F97L;
xvi) N7T, I50T, F97L;
xvii) N7T, I50T, H85R;
xviii) I50T, H85R, G198D;
xix) I50T, F97L, E195G, M196T;
xx) I50T, H85R, G198D;
xxi) FY3, I50T, G198D;

xxii) F3Y, G166E, E195G, M196T;
xxiii) F3Y, I50T, F97L, G198D;
xxiv) F3Y, I50T, F97L, G166E, G198D;
xxv) I50T, H174R, G198D;
xxvi) F3Y, I50T, A111V;
xxvii) F3Y, I50T, G166E, G198D;
xxviii) F3Y, I50T, A111V, G198D; and
xxix) F3Y, I50T, F97L, E195G, M196T;
wherein said mutant Pm promoter and mutant Pm mRNA leader enhance gene expression compared to gene expression obtained using only the mutant Pm promoter and compared to gene expression obtained using only the mutant Pm mRNA leader.

5. A vector comprising the nucleic acid molecule of claim 4.

6. The vector of claim 5, wherein said vector is capable of integrating into a host chromosome.

7. The vector of claim 6, wherein said vector is capable of autonomous replication.

8. A host cell or library comprising the nucleic acid molecule of claim 4.

9. An expression system comprising the nucleic acid molecule of claim 4 wherein said expression system is capable of enhancing the expression of a desired gene product.

10. A method of identifying a mutant combination comprising a mutant promoter and a mutant mRNA leader, and optionally mutant XylS, which mutant combination enhances expression of a desired gene, said method comprising:
    a) providing a vector comprising a desired gene and a reporter gene translationally coupled thereto;
    b) introducing a mutant Pm promoter and a DNA sequence corresponding to a mutant Pm mRNA leader, and optionally a DNA sequence encoding a mutant XylS, into said vector upstream of said desired gene, wherein
       (i) said mutant Pm promoter comprises 1 to 8 mutations, wherein said mutations are selected from substitutions in the −10 region which spans the nucleotide sequence from −1 to −25 and deletions in the transcription initiation region or at positions −1 to −6, and wherein said mutations comprise at least one said deletion;
       (ii) said DNA sequence corresponding to a mutant Pm mRNA leader comprises 2 to 8 mutations, wherein said mutations are selected from 1 to 6 substitutions downstream of position +7 and 1 to 3 deletions downstream of position +7, and
       (iii) said mutant XylS comprises 1 to 6 substitutions in the N-terminal domain and enhances gene expression compared to gene expression obtained using the corresponding unmutated XylS; and
    c) determining the level of expression of said reporter gene,
    wherein an increased level of expression of the reporter gene compared to gene expression obtained using only the mutant Pm promoter and compared to gene expression obtained using only the mutant Pm mRNA leader, and a level of gene expression obtained by the combination of the mutant Pm promoter and the mutant Pm mRNA leader greater than an additive effect of the level of gene expression obtained using only the mutant Pm promoter and the level of gene expression obtained using only the mutant Pm mRNA leader, identify the mutant combination as enhancing expression.

11. A vector comprising a desired gene and a reporter gene translationally coupled thereto, and a site for insertion of a mutant combination comprising
    (i) a mutant Pm promoter which increases the amount of transcript produced and enhances gene expression compared to gene expression obtained using the corresponding unmutated Pm promoter and which comprises a sequence selected from the group consisting of SEQ ID NOS: 102 to 119, 121 to 137 and 144 to 145;
    (ii) a mutant DNA region corresponding to a mutant Pm mRNA leader which increases the amount of transcript produced and enhances gene expression compared to gene expression obtained using the corresponding unmutated Pm mRNA leader and which comprises a sequence selected from the group consisting of SEQ ID NOS: 2 to 12, 14 to 37 and 147 to 163; and
    (iii) optionally a mutant XylS-encoding DNA sequence which encodes a mutant XylS comprising a genotype selected from the group consisting of:
    i) I50T, F97L;
    ii) I50T, H85R;
    iii) F3Y, I50T, H85R;
    iv) K38E, I50T, H85R;
    v) N7S, I50T, H85R;
    vi) K38E, I50T, F97L;
    vii) N7S, I50T, F97L;
    viii) R45T, I50T, H85R;
    ix) R45T, I50T, F97L;
    x) F3Y, G166E;
    xi) I50V, H174R, Y96C;
    xii) E195G, M196T;
    xiii) I50T, A111V;
    xiv) I50T, F97L, G198D;
    xv) F3Y, I50T, F97L;
    xvi) N7T, I50T, F97L;
    xvii) N7T, I50T, H85R;
    xviii) I50T, H85R, G198D;
    xix) I50T, F97L, E195G, M196T;
    xx) I50T, H85R, G198D;
    xxi) FY3, I50T, G198D;
    xxii) F3Y, G166E, E195G, M196T;
    xxiii) F3Y, I50T, F97L, G198D;
    xxiv) F3Y, I50T, F97L, G166E, G198D;
    xxv) I50T, H174R, G198D;
    xxvi) F3Y, I50T, A111V;
    xxvii) F3Y, I50T, G166E, G198D;
    xxviii) F3Y, I50T, A111V, G198D; and
    xxix) F3Y, I50T, F97L, E195G, M196T,
    wherein said mutant Pm promoter and mutant Pm mRNA leader, and optionally mutant XylS, enhance expression of the desired gene product compared to gene expression obtained using the corresponding unmutated Pm promoter and unmutated Pm mRNA leader, and optionally unmutated XylS.

12. The vector of claim 11 further comprising a mutant combination comprising:
    (i) a mutant Pm promoter which increases the amount of transcript produced and enhances gene expression compared to gene expression obtained using the corresponding unmutated Pm promoter and which comprises a sequence selected from the group consisting of SEQ ID NOS: 102 to 119, 121 to 137 and 144 to 145;
    (ii) a DNA region corresponding to a mutant Pm mRNA leader which increases the amount of transcript produced and enhances gene expression compared to gene expression obtained using the corresponding unmutated Pm mRNA leader and which comprises a sequence selected from the group consisting of SEQ ID NOS: 2 to 12, 14 to 37 and 147 to 163; and
(iii) optionally a mutant XylS-encoding DNA sequence which encodes a mutant XylS comprising a genotype selected from the group consisting of:
i) I50T, F97L;
ii) I50T, H85R;
iii) F3Y, I50T, H85R;
iv) K38E, I50T, H85R;
v) N7S, I50T, H85R;
vi) K38E, I50T, F97L;
vii) N7S, I50T, F97L;
viii) R45T, I50T, H85R;
ix) R45T, I50T, F97L;
x) F3Y, G166E;
xi) 150V, H174R, Y96C;
xii) E195G, M196T;
xiii) I50T, A111V;
xiv) I50T, F97L, G198D;
xv) F3Y, I50T, F97L;
xvi) N7T, I50T, F97L;
xvii) N7T, I50T, H85R;
xviii) I50T, H85R, G198D;
xix) I50T, F97L, E195G, M196T;
xx) I50T, H85R, G198D;
xxi) FY3, 150T, G198D;
xxii) F3Y, G166E, E195G, M196T;
xxiii) F3Y, I50T, F97L, G198D;
xxiv) F3Y, I50T, F97L, G166E, G198D;
xxv) I50T, H174R, G198D;
xxvi) F3Y, I50T, A111V;
xxvii) F3Y, I50T, G166E, G198D;
xxviii) F3Y, I50T, A111V, G198D; and
xxix) F3Y, I50T, F97L, E195G, M196T.

13. A library comprising the vector of claim 11.

14. The method of claim 10, wherein the mutant Pm promoter and mutant Pm mRNA leader have at least 80% sequence identity to the sequence of the unmutated Pm promoter and the sequence of the unmutated Pm mRNA leader, respectively.

15. A method of selecting a mutant Pm promoter and mutant Pm mRNA leader for enhancing expression of a desired gene product, wherein transcript production from the gene is increased and results in enhanced expression of the desired gene product and wherein said gene product is expressed from a Pm promoter, said method comprising:
(a) providing a plurality of combinations of a mutant Pm promoter and a mutant Pm mRNA leader from a DNA library of mutant Pm promoters and mutant Pm mRNA leaders, and/or combinations thereof, wherein
  (i) each mutant Pm promoter increases the amount of transcript produced and enhances gene expression compared to gene expression obtained using the corresponding unmutated Pm promoter and comprises a sequence selected from the group consisting of SEQ ID NOS: 102 to 119, 121 to 137 and 144 to 145; and
  (ii) each mutant Pm mRNA leader increases the amount of transcript produced and enhances gene expression compared to gene expression obtained using the corresponding unmutated Pm mRNA leader and comprises a sequence selected from the group consisting of SEQ ID NOS: 2 to 12, 14 to 37 and 147 to 163;
(b) for each of the plurality of provided combinations, expressing said gene product using said combination, and
(c) selecting a mutant Pm promoter and a mutant Pm mRNA leader combination which increased the amount of transcript produced and enhanced expression of the desired gene product compared to gene expression obtained using the corresponding unmutated Pm promoter and unmutated Pm mRNA leader.

16. The method of claim 15, wherein the library further includes mutant DNAs encoding XylS mutants comprising a genotype selected from the group consisting of:
i) I50T, F97L;
ii) I50T, H85R;
iii) F3Y, I50T, H85R;
iv) K38E, I50T, H85R;
v) N7S, I50T, H85R;
vi) K38E, I50T, F97L;
vii) N7S, I50T, F97L;
viii) R45T, I50T, H85R;
ix) R45T, I50T, F97L;
x) F3Y, G166E;
xi) 150V, H174R, Y96C;
xii) E195G, M196T;
xiii) I50T, A111V;
xiv) I50T, F97L, G198D;
xv) F3Y, I50T, F97L;
xvi) N7T, I50T, F97L;
xvii) N7T, I50T, H85R;
xviii) I50T, H85R, G198D;
xix) I50T, F97L, E195G, M196T;
xx) I50T, H85R, G198D;
xxi) FY3, 150T, G198D;
xxii) F3Y, G166E, E195G, M196T;
xxiii) F3Y, I50T, F97L, G198D;
xxiv) F3Y, I50T, F97L, G166E, G198D;
xxv) I50T, H174R, G198D;
xxvi) F3Y, I50T, A111V;
xxvii) F3Y, I50T, G166E, G198D;
xxviii) F3Y, I50T, A111V, G198D; and
xxix) F3Y, I50T, F97L, E195G, M196T, or combinations thereof with the mutant Pm promoter and/or the mutant Pm mRNA leader, and
wherein the method comprises:
(a) providing a plurality of combinations of a mutant Pm promoter, a mutant Pm mRNA leader and a mutant XylS-encoding DNA,
(b) for each of the plurality of provided combinations, expressing said gene product using said combination, and
(c) selecting a mutant Pm promoter, mutant Pm mRNA leader and mutant XylS-encoding DNA combination which increased the amount of transcript produced and enhanced expression of the desired gene product compared to gene expression obtained using the corresponding unmutated Pm promoter, unmutated Pm mRNA leader and unmutated XylS-encoding DNA.

17. A method of enhancing expression of a desired gene product wherein transcript production from said gene is increased and results in enhanced expression of the desired gene product and wherein said gene product is expressed from a Pm promoter, said method comprising:
(a) providing a plurality of combinations of a mutant Pm promoter and a mutant Pm mRNA leader from a DNA library of mutant Pm promoters and mutant Pm mRNA leaders, and/or combinations thereof, wherein
  (i) each mutant Pm promoter increases the amount of transcript produced and enhances gene expression compared to gene expression obtained using the corresponding unmutated Pm promoter and comprises a sequence selected from the group consisting of SEQ ID NOS: 102 to 119, 121 to 137 and 144 to 145; and (ii) each mutant Pm mRNA leader increases the amount of transcript produced and enhances gene expression compared to gene expression obtained using the corresponding unmutated Pm mRNA leader and comprises a sequence selected from the group consisting of SEQ ID NOS: 2 to 12, 14 to 37 and 147 to 163;

(b) for each of the plurality of provided combinations, expressing said gene product using said combination, (c) selecting a mutant Pm promoter and a mutant Pm mRNA leader combination which increased the amount of transcript produced and enhanced expression of the desired gene product compared to gene expression obtained using the corresponding unmutated Pm promoter and unmutated Pm mRNA leader; and (d) further expressing said gene using the selected combination.

18. The method of claim 1, wherein the level of gene expression obtained by the combination of said mutant Pm promoter and said mutant Pm mRNA leader is greater than an additive effect of the level of gene expression obtained using only the mutant Pm promoter and the level of gene expression obtained using only the mutant Pm mRNA leader.

19. The method of claim 3, wherein said mutant Pm promoter and mutant Pm mRNA leader combination, or optionally said mutant Pm promoter, mutant Pm mRNA leader and mutant XylS combination, enhances expression of the desired gene product compared to gene expression obtained using only the mutant Pm promoter and compared to gene expression obtained using only the mutant Pm mRNA leader, and wherein the level of gene expression obtained by the combination of the mutant Pm promoter and the mutant Pm mRNA leader is greater than an additive effect of the level of gene expression obtained using only the mutant Pm promoter and the level of gene expression obtained using only the mutant Pm mRNA leader.

20. The isolated nucleic acid of claim 4, wherein the level of gene expression obtained by the combination of the mutant Pm promoter and the mutant Pm mRNA leader is greater than an additive effect of the level of gene expression obtained using only the mutant Pm promoter and the level of gene expression obtained using only the mutant Pm mRNA leader.

21. The vector of claim 11, wherein the level of gene expression obtained by the combination of the mutant Pm promoter and the mutant Pm mRNA leader is greater than an additive effect of the level of gene expression obtained using only the mutant Pm promoter and the level of gene expression obtained using only the mutant Pm mRNA leader.

22. The method of claim 15, wherein the selected mutant Pm promoter and mutant Pm mRNA leader combination enhanced expression of the desired gene product compared to gene expression obtained using only the mutant Pm promoter and compared to gene expression obtained using only the mutant Pm mRNA leader, and wherein the level of gene expression obtained by the selected mutant Pm promoter and the mutant Pm mRNA leader combination is greater than an additive effect of the level of gene expression obtained using only the mutant Pm promoter and the level of gene expression obtained using only the mutant Pm mRNA leader.

23. The method of claim 17, wherein the selected mutant Pm promoter and mutant Pm mRNA leader combination enhanced expression of the desired gene product compared to gene expression obtained using only the mutant Pm promoter and compared to gene expression obtained using only the mutant Pm mRNA leader, and wherein the level of gene expression obtained by the selected mutant Pm promoter and the mutant Pm mRNA leader combination is greater than an additive effect of the level of gene expression obtained using only the mutant Pm promoter and the level of gene expression obtained using only the mutant Pm mRNA leader.

24. The method of claim 1, wherein the mutant Pm promoter is selected from SEQ ID NOS:115 to 118 and 126 to 133.

25. The method of claim 1, wherein the mutant Pm mRNA leader is selected from SEQ ID NOS: 21 to 26.

26. The nucleic acid molecule of claim 4, wherein the mutant Pm promoter is selected from SEQ ID NOS:115 to 118 and 126 to 133.

27. The nucleic acid molecule of claim 4, wherein the mutant Pm mRNA leader is selected from SEQ ID NOS: 21 to 26.

* * * * *

UNITED STATES PATENT AND TRADEMARK OFFICE
CERTIFICATE OF CORRECTION

PATENT NO. : 9,556,440 B2
APPLICATION NO. : 12/520139
DATED : January 31, 2017
INVENTOR(S) : Lale et al.

Page 1 of 2

It is certified that error appears in the above-identified patent and that said Letters Patent is hereby corrected as shown below:

In the Claims

Claim 2, Column 105, Line 15, change "150V" to --I50V--.

Claim 2, Column 105, Line 25, change "150T" to --I50T--.

Claim 3, Column 105, Line 35, after "product" add --,--.

Claim 3, Column 105, Line 67, change "150V" to --I50V--.

Claim 3, Column 106, Line 10, change "150T" to --I50T--.

Claim 4, Column 106, Line 57, change "150V" to --I50V--.

Claim 4, Column 106, Line 67, change "150T" to --I50T--.

Claim 11, Column 108, Line 30, change "150V" to --I50V--.

Claim 11, Column 108, Line 40, change "150T" to --I50T--.

Claim 12, Column 109, Line 16, change "150V" to --I50V--.

Claim 12, Column 109, Line 26, change "150T" to --I50T--.

Claim 16, Column 110, Line 20, change "150V" to --I50V--.

Signed and Sealed this
Eleventh Day of July, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,556,440 B2

Claim 16, Column 110, Line 30, change "150T" to --I50T--.

Claim 17, Column 110, Line 56, after "product" add --,--.

SEQUENCE LISTING

<160> NUMBER OF SEQ ID NOS: 163

<210> SEQ ID NO 1
<211> LENGTH: 35
<212> TYPE: DNA
<213> ORGANISM: Artificial
<220> FEATURE:
<223> OTHER INFORMATION: Pm UTR

<400> SEQUENCE: 1
aactagtaca ataataatgg agtcatgaac atatg        35

<210> SEQ ID NO 2
<211> LENGTH: 35
<212> TYPE: DNA
<213> ORGANISM: Artificial
<220> FEATURE:
<223> OTHER INFORMATION: mutant Pm UTR

<400> SEQUENCE: 2
aactagtata acactaatgg agccatgaac atatg        35

<210> SEQ ID NO 3
<211> LENGTH: 35
<212> TYPE: DNA
<213> ORGANISM: Artificial

```
<220> FEATURE:
<223> OTHER INFORMATION: mutant Pm UTR

<400> SEQUENCE: 3
acatagtaca ttaatattgg agtcatgaac atatg                              35

<210> SEQ ID NO 4
<211> LENGTH: 35
<212> TYPE: DNA
<213> ORGANISM: Artificial
<220> FEATURE:
<223> OTHER INFORMATION: mutant Pm UTR

<400> SEQUENCE: 4
acattgtact ataatgatgg agtcatgaac atatg                              35

<210> SEQ ID NO 5
<211> LENGTH: 35
<212> TYPE: DNA
<213> ORGANISM: Artificial
<220> FEATURE:
<223> OTHER INFORMATION: mutant Pm UTR

<400> SEQUENCE: 5
atatagtaca acaatactgg agtcatgaac atatg                              35

<210> SEQ ID NO 6
<211> LENGTH: 35
<212> TYPE: DNA
<213> ORGANISM: Artificial
<220> FEATURE:
<223> OTHER INFORMATION: mutant Pm UTR

<400> SEQUENCE: 6
atatactaca acattaatgg agtcatgaac atatg                              35

<210> SEQ ID NO 7
<211> LENGTH: 35
<212> TYPE: DNA
<213> ORGANISM: Artificial
<220> FEATURE:
<223> OTHER INFORMATION: mutant Pm UTR

<400> SEQUENCE: 7
aaattgtacc ataatactgg agtcatgaac atatg                              35

<210> SEQ ID NO 8
<211> LENGTH: 35
<212> TYPE: DNA
<213> ORGANISM: Artificial
<220> FEATURE:
<223> OTHER INFORMATION: mutant Pm UTR

<400> SEQUENCE: 8
atctagtata acataaatgg agtcatgaac atatg                              35

<210> SEQ ID NO 9
<211> LENGTH: 35
<212> TYPE: DNA
<213> ORGANISM: Artificial
<220> FEATURE:
<223> OTHER INFORMATION: mutant Pm UTR

<400> SEQUENCE: 9
acatagtaca atattaatgg agtcatgaac atatg                              35
```

```
<210> SEQ ID NO 10
<211> LENGTH: 35
<212> TYPE: DNA
<213> ORGANISM: Artificial
<220> FEATURE:
<223> OTHER INFORMATION: mutant Pm UTR

<400> SEQUENCE: 10
atctagtgta acataaatgg agtcatgaac atatg                              35

<210> SEQ ID NO 11
<211> LENGTH: 35
<212> TYPE: DNA
<213> ORGANISM: Artificial
<220> FEATURE:
<223> OTHER INFORMATION: mutant Pm UTR

<400> SEQUENCE: 11
aaatagtacc acactaatgg agtcatgaac atatg                              35

<210> SEQ ID NO 12
<211> LENGTH: 35
<212> TYPE: DNA
<213> ORGANISM: Artificial
<220> FEATURE:
<223> OTHER INFORMATION: mutant Pm UTR

<400> SEQUENCE: 12
aaatagtaca ctactaatgg agtaatgaac atatg                              35

<210> SEQ ID NO 13
<211> LENGTH: 35
<212> TYPE: DNA
<213> ORGANISM: Artificial
<220> FEATURE:
<223> OTHER INFORMATION: mutant Pm UTR

<400> SEQUENCE: 13
aacatgtaca ataataatgg agtcatgaac atatg                              35

<210> SEQ ID NO 14
<211> LENGTH: 35
<212> TYPE: DNA
<213> ORGANISM: Artificial
<220> FEATURE:
<223> OTHER INFORMATION: mutant Pm UTR

<400> SEQUENCE: 14
aacatgtacc ataataaagg agtcttgaac atatg                              35

<210> SEQ ID NO 15
<211> LENGTH: 35
<212> TYPE: DNA
<213> ORGANISM: Artificial
<220> FEATURE:
<223> OTHER INFORMATION: mutant Pm UTR

<400> SEQUENCE: 15
aacatgtacc ataataatgg agttttgaac atatg                              35

<210> SEQ ID NO 16
<211> LENGTH: 35
<212> TYPE: DNA
<213> ORGANISM: Artificial
<220> FEATURE:
<223> OTHER INFORMATION: mutant Pm UTR
```

<400> SEQUENCE: 16
aacatgtacc atattaatgg agtcttgaac atatg                              35

<210> SEQ ID NO 17
<211> LENGTH: 35
<212> TYPE: DNA
<213> ORGANISM: Artificial
<220> FEATURE:
<223> OTHER INFORMATION: mutant Pm UTR

<400> SEQUENCE: 17
aacatgtacc ataataatgg agtaatgaac atatg                              35

<210> SEQ ID NO 18
<211> LENGTH: 35
<212> TYPE: DNA
<213> ORGANISM: Artificial
<220> FEATURE:
<223> OTHER INFORMATION: mutant Pm UTR

<400> SEQUENCE: 18
aacatgtcaa acactaatgg agtaatgaac atatg                              35

<210> SEQ ID NO 19
<211> LENGTH: 35
<212> TYPE: DNA
<213> ORGANISM: Artificial
<220> FEATURE:
<223> OTHER INFORMATION: mutant Pm UTR

<400> SEQUENCE: 19
aacatgtaac ataataatgg agtcttgaac atatg                              35

<210> SEQ ID NO 20
<211> LENGTH: 35
<212> TYPE: DNA
<213> ORGANISM: Artificial
<220> FEATURE:
<223> OTHER INFORMATION: mutant Pm UTR

<400> SEQUENCE: 20
aacatgtaac ataatactgg agtaatgaac atatg                              35

<210> SEQ ID NO 21
<211> LENGTH: 35
<212> TYPE: DNA
<213> ORGANISM: Artificial
<220> FEATURE:
<223> OTHER INFORMATION: mutant Pm UTR

<400> SEQUENCE: 21
aacatgtacc acaataatgg agtcttgaac atatg                              35

<210> SEQ ID NO 22
<211> LENGTH: 35
<212> TYPE: DNA
<213> ORGANISM: Artificial
<220> FEATURE:
<223> OTHER INFORMATION: mutant Pm UTR

<400> SEQUENCE: 22
aacatgtaca atcatacagg agtcatcaac atatg                              35

<210> SEQ ID NO 23

```
<210> SEQ ID NO 23
<211> LENGTH: 35
<212> TYPE: DNA
<213> ORGANISM: Artificial
<220> FEATURE:
<223> OTHER INFORMATION: mutant Pm UTR

<400> SEQUENCE: 23
aacatgtacc acaataatgg agttttgaac atatg                              35

<210> SEQ ID NO 24
<211> LENGTH: 35
<212> TYPE: DNA
<213> ORGANISM: Artificial
<220> FEATURE:
<223> OTHER INFORMATION: mutant Pm UTR

<400> SEQUENCE: 24
aacatgttac acaataatgg agtaatgaac atatg                              35

<210> SEQ ID NO 25
<211> LENGTH: 33
<212> TYPE: DNA
<213> ORGANISM: Artificial
<220> FEATURE:
<223> OTHER INFORMATION: mutant Pm UTR

<400> SEQUENCE: 25
aacatgtcca ataataatgg agtataacat atg                                33

<210> SEQ ID NO 26
<211> LENGTH: 35
<212> TYPE: DNA
<213> ORGANISM: Artificial
<220> FEATURE:
<223> OTHER INFORMATION: mutant Pm UTR

<400> SEQUENCE: 26
aacatgtccc attatactgg agtcttgaac atatg                              35

<210> SEQ ID NO 27
<211> LENGTH: 35
<212> TYPE: DNA
<213> ORGANISM: Artificial
<220> FEATURE:
<223> OTHER INFORMATION: mutant Pm UTR

<400> SEQUENCE: 27
aacatgtacc ataataatgg agtcctgaac atatg                              35

<210> SEQ ID NO 28
<211> LENGTH: 35
<212> TYPE: DNA
<213> ORGANISM: Artificial
<220> FEATURE:
<223> OTHER INFORMATION: mutant Pm UTR

<400> SEQUENCE: 28
aacatgtacc atattaatgg agttatgaac atatg                              35

<210> SEQ ID NO 29
<211> LENGTH: 35
<212> TYPE: DNA
<213> ORGANISM: Artificial
<220> FEATURE:
<223> OTHER INFORMATION: mutant Pm UTR

<400> SEQUENCE: 29
```
aacatgtacc ataataatgg agtcttgaac atatg                           35

<210> SEQ ID NO 30
<211> LENGTH: 36
<212> TYPE: DNA
<213> ORGANISM: Artificial
<220> FEATURE:
<223> OTHER INFORMATION: mutant Pm UTR

<400> SEQUENCE: 30
aacatgtact ataataatcg aggtcatgaa catatg                          36

<210> SEQ ID NO 31
<211> LENGTH: 36
<212> TYPE: DNA
<213> ORGANISM: Artificial
<220> FEATURE:
<223> OTHER INFORMATION: mutant Pm UTR

<400> SEQUENCE: 31
aacatgttac aataattttg gagccatgaa catatg                          36

<210> SEQ ID NO 32
<211> LENGTH: 35
<212> TYPE: DNA
<213> ORGANISM: Artificial
<220> FEATURE:
<223> OTHER INFORMATION: mutant Pm UTR

<400> SEQUENCE: 32
aacatgtaca ataatacacg agtcatgaac atatg                           35

<210> SEQ ID NO 33
<211> LENGTH: 35
<212> TYPE: DNA
<213> ORGANISM: Artificial
<220> FEATURE:
<223> OTHER INFORMATION: mutant Pm UTR

<400> SEQUENCE: 33
aacatgtcca agtatacagg agtcatgaac atatg                           35

<210> SEQ ID NO 34
<211> LENGTH: 35
<212> TYPE: DNA
<213> ORGANISM: Artificial
<220> FEATURE:
<223> OTHER INFORMATION: mutant Pm UTR

<400> SEQUENCE: 34
aacatgtacc attataacgg agtaatgaac atatg                           35

<210> SEQ ID NO 35
<211> LENGTH: 35
<212> TYPE: DNA
<213> ORGANISM: Artificial
<220> FEATURE:
<223> OTHER INFORMATION: mutant Pm UTR

<400> SEQUENCE: 35
aacatgtacc ataatacagg agttatgaac atatg                           35

<210> SEQ ID NO 36
<211> LENGTH: 35
<212> TYPE: DNA

```
<213> ORGANISM: Artificial
<220> FEATURE:
<223> OTHER INFORMATION: mutant Pm UTR

<400> SEQUENCE: 36
aacatgtaca ataatacagg aacaatgaac atatg                           35

<210> SEQ ID NO 37
<211> LENGTH: 35
<212> TYPE: DNA
<213> ORGANISM: Artificial
<220> FEATURE:
<223> OTHER INFORMATION: mutant Pm UTR

<400> SEQUENCE: 37
aacatgtaca atcataccag agtaatgcca atatg                           35

<210> SEQ ID NO 38
<211> LENGTH: 91
<212> TYPE: DNA
<213> ORGANISM: Artificial
<220> FEATURE:
<223> OTHER INFORMATION: Wild-type Pm promoter

<400> SEQUENCE: 38
gatagggata agtccagcct tgcaagaagc ggatacagga gtgcaaaaaa tggctatctc    60
tagaaaggcc taccccttag gctttatgca a                                  91

<210> SEQ ID NO 39
<211> LENGTH: 321
<212> TYPE: PRT
<213> ORGANISM: Pseudomonas putida

<400> SEQUENCE: 39
```

Met Asp Phe Cys Leu Leu Asn Glu Lys Ser Gln Ile Phe Val His Ala
1               5                   10                  15

Glu Pro Tyr Ala Val Ser Asp Tyr Val Asn Gln Tyr Val Gly Thr His
            20                  25                  30

Ser Ile Arg Leu Pro Lys Gly Gly Arg Pro Ala Gly Arg Leu His His
        35                  40                  45

Arg Ile Phe Gly Cys Leu Asp Leu Cys Arg Ile Ser Tyr Gly Gly Ser
    50                  55                  60

Val Arg Val Ile Ser Pro Gly Leu Glu Thr Cys Tyr His Leu Gln Ile
65                  70                  75                  80

Ile Leu Lys Gly His Cys Leu Trp Arg Gly His Gly Gln Glu His Tyr
                85                  90                  95

Phe Ala Pro Gly Glu Leu Leu Leu Asn Pro Asp Asp Gln Ala Asp
            100                 105                 110

Leu Thr Tyr Ser Glu Asp Cys Glu Lys Phe Ile Val Lys Leu Pro Ser
        115                 120                 125

Val Val Leu Asp Arg Ala Cys Ser Asp Asn Asn Trp His Lys Pro Arg
    130                 135                 140

Glu Gly Ile Arg Phe Ala Ala Arg His Asn Leu Gln Gln Leu Asp Gly
145                 150                 155                 160

Phe Ile Asn Leu Leu Gly Leu Val Cys Asp Glu Ala Glu His Thr Lys
                165                 170                 175

Ser Met Pro Arg Val Gln Glu His Tyr Ala Gly Ile Ile Ala Ser Lys
            180                 185                 190

Leu Leu Glu Met Leu Gly Ser Asn Val Ser Arg Glu Ile Phe Ser Lys

```
                195                 200                 205
Gly Asn Pro Ser Phe Glu Arg Val Val Gln Phe Ile Glu Glu Asn Leu
    210                 215                 220

Lys Arg Asn Ile Ser Leu Glu Arg Leu Ala Glu Leu Ala Met Met Ser
225                 230                 235                 240

Pro Arg Ser Leu Tyr Asn Leu Phe Glu Lys His Ala Gly Thr Thr Pro
                245                 250                 255

Lys Asn Tyr Ile Arg Asn Arg Lys Leu Glu Ser Ile Arg Ala Cys Leu
            260                 265                 270

Asn Asp Pro Ser Ala Asn Val Arg Ser Ile Thr Glu Ile Ala Leu Asp
        275                 280                 285

Tyr Gly Phe Leu His Leu Gly Arg Phe Ala Glu Asn Tyr Arg Ser Ala
    290                 295                 300

Phe Gly Glu Leu Pro Ser Asp Thr Leu Arg Gln Cys Lys Lys Glu Val
305                 310                 315                 320

Ala

<210> SEQ ID NO 40
<211> LENGTH: 966
<212> TYPE: DNA
<213> ORGANISM: Pseudomonas putida

<400> SEQUENCE: 40
atggattttt gcttattgaa cgagaaaagt cagatcttcg tccacgccga gccctatgca      60
gtctccgatt atgttaacca gtatgtcggt acgcactcta ttcgcctgcc caagggcggg     120
cgcccggcag gcaggctgca ccacagaatc ttcggatgcc tcgacctgtg tcgaatcagc     180
tacggcggta gcgtgagggt aatctcgcct ggattagaga cctgttatca tctgcaaata     240
atactcaaag gccattgcct gtggcgtggc catggccagg agcactattt tgcgccgggc     300
gaactattgc tgctcaatcc ggatgaccaa gccgacctga cctattcaga agattgcgag     360
aaatttatcg ttaaattgcc ctcagtggtc cttgatcggg catgcagtga acaacaattgg     420 cacaagccga gggagggtat ccgtttcgcc gcgcgacaca atctccagca actcgatggc     480
tttatcaatc tactcgggtt agtttgtgac gaagcggaac atacaaagtc gatgcctcgg     540
gtccaagagc actatgcggg gatcatcgct tccaagctgc tcgaaatgct gggcagcaat     600
gtcagccgtg aaattttcag caaaggtaac ccgtctttcg agcgagtcgt tcaattcatt     660
gaggagaatc tcaaacggaa tatcagcctt gagcggttag cggagctggc gatgatgagt     720
ccacgctcgc tctacaattt gttcgagaag catgccggca ccacgccgaa gaactacatc     780
cgcaaccgca agctcgaaag catccgcgcc tgcttgaacg atcccagtgc caatgtgcgt     840
agtataactg agatagccct agactacggc ttcttacatt tgggacgctt cgctgaaaac     900
tataggagcg cgttcggcga gttgccttcc gacaccctgc gtcaatgcaa aaaggaagtg     960
gcttga                                                                966

<210> SEQ ID NO 41
<211> LENGTH: 11
<212> TYPE: DNA
<213> ORGANISM: Artificial
<220> FEATURE:
<223> OTHER INFORMATION: -10 promoter element consensus
<220> FEATURE:
<221> NAME/KEY: variation
<222> LOCATION: (3)..(4)
<223> OTHER INFORMATION: N can be 0-2 nucleotides
<220> FEATURE:
```

```
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 41
tgnncyatnc t                                                             11

<210> SEQ ID NO 42
<211> LENGTH: 6
<212> TYPE: DNA
<213> ORGANISM: Artificial
<220> FEATURE:
<223> OTHER INFORMATION: Pm Promoter motif
<220> FEATURE:
<221> NAME/KEY: misc_feature
<222> LOCATION: (3)..(4)
<223> OTHER INFORMATION: n is a, c, g, or t

<400> SEQUENCE: 42 tannct                                                                    6

<210> SEQ ID NO 43
<211> LENGTH: 11
<212> TYPE: DNA
<213> ORGANISM: Artificial
<220> FEATURE:
<223> OTHER INFORMATION: Optimised -10 promoter element

<400> SEQUENCE: 43
tgtgctatam t                                                             11

<210> SEQ ID NO 44
<211> LENGTH: 29
<212> TYPE: DNA
<213> ORGANISM: Artificial
<220> FEATURE:
<223> OTHER INFORMATION: Primer

<400> SEQUENCE: 44
ctagtacaat aataatgaag tcatgaaca                                          29

<210> SEQ ID NO 45
<211> LENGTH: 27
<212> TYPE: DNA
<213> ORGANISM: Artificial
<220> FEATURE:
<223> OTHER INFORMATION: Primer

<400> SEQUENCE: 45
tatgttcatg acttcattat tattgta                                            27

<210> SEQ ID NO 46
<211> LENGTH: 33
<212> TYPE: DNA
<213> ORGANISM: Artificial
<220> FEATURE:
<223> OTHER INFORMATION: Primer

<400> SEQUENCE: 46
gcataaccag cataaacgtg tccggtttga tag                                     33

<210> SEQ ID NO 47
<211> LENGTH: 33
```

<212> TYPE: DNA
<213> ORGANISM: Artificial
<220> FEATURE:
<223> OTHER INFORMATION: Primer

<400> SEQUENCE: 47
cgataaccag cataaacgtg tccggtttga tag                          33

<210> SEQ ID NO 48
<211> LENGTH: 41
<212> TYPE: DNA
<213> ORGANISM: Artificial
<220> FEATURE:
<223> OTHER INFORMATION: Primer

<400> SEQUENCE: 48
cttaggcttt atgcaacatg tacaataata atgaagtcat g                 41

<210> SEQ ID NO 49
<211> LENGTH: 41
<212> TYPE: DNA
<213> ORGANISM: Artificial
<220> FEATURE:
<223> OTHER INFORMATION: Primer

<400> SEQUENCE: 49
catgacttca ttattattgt acatgttgca taaagcctaa g                 41

<210> SEQ ID NO 50
<211> LENGTH: 33
<212> TYPE: DNA
<213> ORGANISM: Artificial
<220> FEATURE:
<223> OTHER INFORMATION: Primer

<400> SEQUENCE: 50
aaccgagaat tcgccgttgg atagctccgc tac                          33

<210> SEQ ID NO 51
<211> LENGTH: 39
<212> TYPE: DNA
<213> ORGANISM: Artificial
<220> FEATURE:
<223> OTHER INFORMATION: Primer

<400> SEQUENCE: 51
aatgcattgg ttctgcagga gagtgtctaa gaaagccgg                    39

<210> SEQ ID NO 52
<211> LENGTH: 32
<212> TYPE: DNA
<213> ORGANISM: Artificial
<220> FEATURE:
<223> OTHER INFORMATION: wt Pm oligonucleotide

<400> SEQUENCE: 52
catgttgcat aaagcctaag gggtaggcct tt                           32

<210> SEQ ID NO 53
<211> LENGTH: 32
<212> TYPE: DNA
<213> ORGANISM: Artificial
<220> FEATURE:
<223> OTHER INFORMATION: Mixed oligonucleotide

<400> SEQUENCE: 53
ctagaaaggc ctacccctta ggctttatgc aa          32

<210> SEQ ID NO 54
<211> LENGTH: 30
<212> TYPE: DNA
<213> ORGANISM: Artificial
<220> FEATURE:
<223> OTHER INFORMATION: Pm high expression mutant 7b oligonucleotide

<400> SEQUENCE: 54
catgtgctaa agtttaaggg gtaggccttt              30

<210> SEQ ID NO 55
<211> LENGTH: 30
<212> TYPE: DNA
<213> ORGANISM: Artificial
<220> FEATURE:
<223> OTHER INFORMATION: Mixed oligonucleotide

<400> SEQUENCE: 55
ctagaaaggc ctacccctta aactttagca              30

<210> SEQ ID NO 56
<211> LENGTH: 33
<212> TYPE: DNA
<213> ORGANISM: Artificial
<220> FEATURE:
<223> OTHER INFORMATION: Sequencing primer

<400> SEQUENCE: 56
gcataaccag cataaacgtg tccggtttga tag           33

<210> SEQ ID NO 57
<211> LENGTH: 22
<212> TYPE: DNA
<213> ORGANISM: Artificial
<220> FEATURE:
<223> OTHER INFORMATION: Primer

<400> SEQUENCE: 57
ctttcaccag cgtttctggg tg                      22

<210> SEQ ID NO 58
<211> LENGTH: 21
<212> TYPE: DNA
<213> ORGANISM: Artificial
<220> FEATURE:
<223> OTHER INFORMATION: Primer

<400> SEQUENCE: 58
gatgtagaaa ggcgccaagt c                       21

<210> SEQ ID NO 59
<211> LENGTH: 30
<212> TYPE: DNA
<213> ORGANISM: Artificial
<220> FEATURE:
<223> OTHER INFORMATION: Primer

<400> SEQUENCE: 59
cgacacggaa atgttgaata ctcatatgtt              30

<210> SEQ ID NO 60
<211> LENGTH: 33
<212> TYPE: DNA
<213> ORGANISM: Artificial

```
<220> FEATURE:
<223> OTHER INFORMATION: Primer

<400> SEQUENCE: 60
gcataaccag cataaacgtg tccggtttga tag                              33

<210> SEQ ID NO 61
<211> LENGTH: 22
<212> TYPE: DNA
<213> ORGANISM: Artificial
<220> FEATURE:
<223> OTHER INFORMATION: Primer

<400> SEQUENCE: 61
ctttcaccag cgtttctggg tg                                          22

<210> SEQ ID NO 62
<211> LENGTH: 21
<212> TYPE: DNA
<213> ORGANISM: Artificial
<220> FEATURE:
<223> OTHER INFORMATION: bla-specific primer with fluorescent label
      (6-FAM)

<400> SEQUENCE: 62
ccgctgttga gatccagttc g                                           21

<210> SEQ ID NO 63
<211> LENGTH: 33
<212> TYPE: DNA
<213> ORGANISM: Artificial
<220> FEATURE:
<223> OTHER INFORMATION: Primer

<400> SEQUENCE: 63
gcataaccag cataaacgtg tccggtttga tag                              33

<210> SEQ ID NO 64
<211> LENGTH: 20
<212> TYPE: DNA
<213> ORGANISM: Artificial
<220> FEATURE:
<223> OTHER INFORMATION: Primer

<400> SEQUENCE: 64
gtgtatgcgg cgaccgagtt                                             20

<210> SEQ ID NO 65
<211> LENGTH: 11
<212> TYPE: DNA
<213> ORGANISM: Artificial
<220> FEATURE:
<223> OTHER INFORMATION: Optimized -10 promoter element

<400> SEQUENCE: 65
tgtgctatam t                                                      11

<210> SEQ ID NO 66
<211> LENGTH: 29
<212> TYPE: DNA
<213> ORGANISM: Artificial
<220> FEATURE:
<223> OTHER INFORMATION: Primer

<400> SEQUENCE: 66
ctagtacaat aataatgaag tcatgaaca                                   29
```

```
<210> SEQ ID NO 67
<211> LENGTH: 27
<212> TYPE: DNA
<213> ORGANISM: Artificial
<220> FEATURE:
<223> OTHER INFORMATION: Primer

<400> SEQUENCE: 67
tatgttcatg acttcattat tattgta                                            27

<210> SEQ ID NO 68
<211> LENGTH: 33
<212> TYPE: DNA
<213> ORGANISM: Artificial
<220> FEATURE:
<223> OTHER INFORMATION: Primer

<400> SEQUENCE: 68
gcataaccag cataaacgtg tccggtttga tag                                     33

<210> SEQ ID NO 69
<211> LENGTH: 33
<212> TYPE: DNA
<213> ORGANISM: Artificial
<220> FEATURE:
<223> OTHER INFORMATION: Primer

<400> SEQUENCE: 69
cgataaccag cataaacgtg tccggtttga tag                                     33

<210> SEQ ID NO 70
<211> LENGTH: 41
<212> TYPE: DNA
<213> ORGANISM: Artificial
<220> FEATURE:
<223> OTHER INFORMATION: Primer

<400> SEQUENCE: 70
cttaggcttt atgcaacatg tacaataata atgaagtcat g                            41

<210> SEQ ID NO 71
<211> LENGTH: 41
<212> TYPE: DNA
<213> ORGANISM: Artificial
<220> FEATURE:
<223> OTHER INFORMATION: Primer

<400> SEQUENCE: 71
catgacttca ttattattgt acatgttgca taaagcctaa g                            41

<210> SEQ ID NO 72
<211> LENGTH: 33
<212> TYPE: DNA
<213> ORGANISM: Artificial
<220> FEATURE:
<223> OTHER INFORMATION: Primer

<400> SEQUENCE: 72
aaccgagaat tcgccgttgg atagctccgc tac                                     33

<210> SEQ ID NO 73
<211> LENGTH: 39
<212> TYPE: DNA
<213> ORGANISM: Artificial
<220> FEATURE:
```

<223> OTHER INFORMATION: Primer

<400> SEQUENCE: 73
aatgcattgg ttctgcagga gagtgtctaa gaaagccgg                              39

<210> SEQ ID NO 74
<211> LENGTH: 27
<212> TYPE: DNA
<213> ORGANISM: Artificial
<220> FEATURE:
<223> OTHER INFORMATION: Primer

<400> SEQUENCE: 74
tatgttcatg actccattat tattgta                                          27

<210> SEQ ID NO 75
<211> LENGTH: 29
<212> TYPE: DNA
<213> ORGANISM: Artificial
<220> FEATURE:
<223> OTHER INFORMATION: Primer

<400> SEQUENCE: 75
catgtacaat aataatggag tcatgaaca                                        29

<210> SEQ ID NO 76
<211> LENGTH: 23
<212> TYPE: DNA
<213> ORGANISM: Artificial
<220> FEATURE:
<223> OTHER INFORMATION: Primer

<400> SEQUENCE: 76
acgttttcca atgatgagca ctt                                              23

<210> SEQ ID NO 77
<211> LENGTH: 16
<212> TYPE: DNA
<213> ORGANISM: Artificial
<220> FEATURE:
<223> OTHER INFORMATION: Primer

<400> SEQUENCE: 77
tgcccggcgt caacac                                                      16

<210> SEQ ID NO 78
<211> LENGTH: 24
<212> TYPE: DNA
<213> ORGANISM: Artificial
<220> FEATURE:
<223> OTHER INFORMATION: Primer

<400> SEQUENCE: 78
tacctttgcc atgtttcaga aaca                                             24

<210> SEQ ID NO 79
<211> LENGTH: 22
<212> TYPE: DNA
<213> ORGANISM: Artificial
<220> FEATURE:
<223> OTHER INFORMATION: Primer

<400> SEQUENCE: 79
atcaggtgcg acaatctatc ga                                               22

<210> SEQ ID NO 80
<211> LENGTH: 20
<212> TYPE: DNA
<213> ORGANISM: Artificial
<220> FEATURE:
<223> OTHER INFORMATION: Primer

<400> SEQUENCE: 80
tggatctcaa cagcggtaag                                              20

<210> SEQ ID NO 81
<211> LENGTH: 21
<212> TYPE: DNA
<213> ORGANISM: Artificial
<220> FEATURE:
<223> OTHER INFORMATION: Primer

<400> SEQUENCE: 81
ggcagcactg cataattctc t                                            21

<210> SEQ ID NO 82
<211> LENGTH: 20
<212> TYPE: DNA
<213> ORGANISM: Artificial
<220> FEATURE:
<223> OTHER INFORMATION: Primer

<400> SEQUENCE: 82
tggagagcaa ctgcataagg                                              20

<210> SEQ ID NO 83
<211> LENGTH: 20
<212> TYPE: DNA
<213> ORGANISM: Artificial
<220> FEATURE:
<223> OTHER INFORMATION: Primer

<400> SEQUENCE: 83
cgcaactgca actccgataa                                              20

<210> SEQ ID NO 84
<211> LENGTH: 20
<212> TYPE: DNA
<213> ORGANISM: Artificial
<220> FEATURE:
<223> OTHER INFORMATION: Primer

<400> SEQUENCE: 84
cgctgaccac cagcttcaat                                              20

<210> SEQ ID NO 85
<211> LENGTH: 20
<212> TYPE: DNA
<213> ORGANISM: Artificial
<220> FEATURE:
<223> OTHER INFORMATION: Primer

<400> SEQUENCE: 85
tgctgcggtc acggttatag                                              20

<210> SEQ ID NO 86
<211> LENGTH: 20
<212> TYPE: DNA
<213> ORGANISM: Artificial
<220> FEATURE:
<223> OTHER INFORMATION: Primer

<400> SEQUENCE: 86
gcaatcaggt gcgacaatct                                          20

<210> SEQ ID NO 87
<211> LENGTH: 20
<212> TYPE: DNA
<213> ORGANISM: Artificial
<220> FEATURE:
<223> OTHER INFORMATION: Primer

<400> SEQUENCE: 87
tcgcagtggt gagtaaccat                                          20

<210> SEQ ID NO 88
<211> LENGTH: 30
<212> TYPE: DNA
<213> ORGANISM: Artificial
<220> FEATURE:
<223> OTHER INFORMATION: SacI-F Primer

<400> SEQUENCE: 88
ctcttatttt aatgtgagct ccttggtgtg                                30

<210> SEQ ID NO 89
<211> LENGTH: 34
<212> TYPE: DNA
<213> ORGANISM: Artificial
<220> FEATURE:
<223> OTHER INFORMATION: SacI-R Primer

<400> SEQUENCE: 89
ctacatcaca ccaaggagct cacattaaaa taag                           34

<210> SEQ ID NO 90
<211> LENGTH: 27
<212> TYPE: DNA
<213> ORGANISM: Artificial
<220> FEATURE:
<223> OTHER INFORMATION: AgeI-R Primer

<400> SEQUENCE: 90
gccgaagaag ggaccggttg gcatcgc                                   27

<210> SEQ ID NO 91
<211> LENGTH: 27
<212> TYPE: DNA
<213> ORGANISM: Artificial
<220> FEATURE:
<223> OTHER INFORMATION: AgeI-F Primer

<400> SEQUENCE: 91
gcgatgccaa ccggtccctt cttcggc                                   27

<210> SEQ ID NO 92
<211> LENGTH: 23
<212> TYPE: DNA
<213> ORGANISM: Artificial
<220> FEATURE:
<223> OTHER INFORMATION: F-epP2 xylS Primer

<400> SEQUENCE: 92
ccacgaagct tcccatggtg acg                                       23

<210> SEQ ID NO 93
<211> LENGTH: 24

```
<212> TYPE: DNA
<213> ORGANISM: Artificial
<220> FEATURE:
<223> OTHER INFORMATION: R-epP2 xylS Primer

<400> SEQUENCE: 93
ggccttgact agagggtacc agag                                          24

<210> SEQ ID NO 94
<211> LENGTH: 25
<212> TYPE: DNA
<213> ORGANISM: Artificial
<220> FEATURE:
<223> OTHER INFORMATION: F-AvrII + Primer

<400> SEQUENCE: 94
gattacgaac ctaggcgaag aaggg                                         25

<210> SEQ ID NO 95
<211> LENGTH: 25
<212> TYPE: DNA
<213> ORGANISM: Artificial
<220> FEATURE:
<223> OTHER INFORMATION: R-AvrII + Primer

<400> SEQUENCE: 95
cccttcttcg cctaggttcg taatc                                         25

<210> SEQ ID NO 96
<211> LENGTH: 24
<212> TYPE: DNA
<213> ORGANISM: Artificial
<220> FEATURE:
<223> OTHER INFORMATION: F-NcoI + Primer

<400> SEQUENCE: 96
gaaccgtgaa ccatggattt ttgc                                          24

<210> SEQ ID NO 97
<211> LENGTH: 24
<212> TYPE: DNA
<213> ORGANISM: Artificial
<220> FEATURE:
<223> OTHER INFORMATION: R-NcoI + Primer

<400> SEQUENCE: 97
gcaaaaatcc atggttcacg gttc                                          24

<210> SEQ ID NO 98
<211> LENGTH: 21
<212> TYPE: DNA
<213> ORGANISM: Artificial
<220> FEATURE:
<223> OTHER INFORMATION: F-NcoI rem. Primer

<400> SEQUENCE: 98
gtgctcctgg gcatggccac g                                             21

<210> SEQ ID NO 99
<211> LENGTH: 21
<212> TYPE: DNA
<213> ORGANISM: Artificial
<220> FEATURE:
<223> OTHER INFORMATION: R-NcoI rem. Primer

<400> SEQUENCE: 99
```
cgtggccatg cccaggagca c    21

<210> SEQ ID NO 100
<211> LENGTH: 66
<212> TYPE: DNA
<213> ORGANISM: Artificial
<220> FEATURE:
<223> OTHER INFORMATION: Pm transcription and translation initiation
      regions

<400> SEQUENCE: 100
tctagaaagg cctacccctt aggctttatg caacatgtac aataataatg aagtcatgaa    60
catatg    66

<210> SEQ ID NO 101
<211> LENGTH: 38
<212> TYPE: DNA
<213> ORGANISM: Artificial
<220> FEATURE:
<223> OTHER INFORMATION: wt -10 Pm region

<400> SEQUENCE: 101
tctagaaagg cctacccctt aggctttatg caacatgt    38

<210> SEQ ID NO 102
<211> LENGTH: 37
<212> TYPE: DNA
<213> ORGANISM: Artificial
<220> FEATURE:
<223> OTHER INFORMATION: m6 -10 Pm region

<400> SEQUENCE: 102
tctagaaagg cctacccctt aggctttatg caactgt    37

<210> SEQ ID NO 103
<211> LENGTH: 36
<212> TYPE: DNA
<213> ORGANISM: Artificial
<220> FEATURE:
<223> OTHER INFORMATION: 12B -10 Pm region

<400> SEQUENCE: 103
tctagaaagg cctacccctt aggctttatg caatgt    36

<210> SEQ ID NO 104
<211> LENGTH: 37
<212> TYPE: DNA
<213> ORGANISM: Artificial
<220> FEATURE:
<223> OTHER INFORMATION: m5 -10 Pm region

<400> SEQUENCE: 104
tctagaaagg cgttccccgt atgctttatg caactgt    37

<210> SEQ ID NO 105
<211> LENGTH: 36
<212> TYPE: DNA
<213> ORGANISM: Artificial
<220> FEATURE:
<223> OTHER INFORMATION: 5D -10 Pm region

<400> SEQUENCE: 105
tctagaaagg tttaccccTT atactttatg caatgt    36

<210> SEQ ID NO 106

```
<211> LENGTH: 36
<212> TYPE: DNA
<213> ORGANISM: Artificial
<220> FEATURE:
<223> OTHER INFORMATION: 4H -10 Pm region

<400> SEQUENCE: 106
tctagaaacg cctacctgtt aggctttatg caatgt                    36

<210> SEQ ID NO 107
<211> LENGTH: 36
<212> TYPE: DNA
<213> ORGANISM: Artificial
<220> FEATURE:
<223> OTHER INFORMATION: 11H -10 Pm region

<400> SEQUENCE: 107
tctagaaacg cttacacatt aggctttatg caatgt                    36

<210> SEQ ID NO 108
<211> LENGTH: 36
<212> TYPE: DNA
<213> ORGANISM: Artificial
<220> FEATURE:
<223> OTHER INFORMATION: 1D -10 Pm region

<400> SEQUENCE: 108
tctagaaagg ccaaccctgt aggctttatg caatgt                    36

<210> SEQ ID NO 109
<211> LENGTH: 36
<212> TYPE: DNA
<213> ORGANISM: Artificial
<220> FEATURE:
<223> OTHER INFORMATION: 7F -10 Pm region

<400> SEQUENCE: 109
tctagaaagg cctacccctt aagctatatg caatgt                    36

<210> SEQ ID NO 110
<211> LENGTH: 36
<212> TYPE: DNA
<213> ORGANISM: Artificial
<220> FEATURE:
<223> OTHER INFORMATION: 1C -10 Pm region

<400> SEQUENCE: 110
tctagaaagg cctacccgtt acgctttatg caatgt                    36

<210> SEQ ID NO 111
<211> LENGTH: 36
<212> TYPE: DNA
<213> ORGANISM: Artificial
<220> FEATURE:
<223> OTHER INFORMATION: 4B -10 Pm region

<400> SEQUENCE: 111
tctagaaagg cctacccgtt atgctttatg caatgt                    36

<210> SEQ ID NO 112
<211> LENGTH: 35
<212> TYPE: DNA
<213> ORGANISM: Artificial
<220> FEATURE:
<223> OTHER INFORMATION: m8 -10 Pm region

<400> SEQUENCE: 112
```
tctagaaaac tctacccgtt acctttatgc aatgt                    35

<210> SEQ ID NO 113
<211> LENGTH: 36
<212> TYPE: DNA
<213> ORGANISM: Artificial
<220> FEATURE:
<223> OTHER INFORMATION: m7 -10 Pm region

<400> SEQUENCE: 113
tctagaaagg aaaacccctt acgctatatg caatgt                   36

<210> SEQ ID NO 114
<211> LENGTH: 36
<212> TYPE: DNA
<213> ORGANISM: Artificial
<220> FEATURE:
<223> OTHER INFORMATION: 3G -10 Pm region

<400> SEQUENCE: 114
tctagaatgg cctatcccctt atgcttatgc aaatgt                  36

<210> SEQ ID NO 115
<211> LENGTH: 37
<212> TYPE: DNA
<213> ORGANISM: Artificial
<220> FEATURE:
<223> OTHER INFORMATION: m1 -10 Pm region

<400> SEQUENCE: 115
tctagaatgc cctatctctt aggcttatgc aacatgt                  37

<210> SEQ ID NO 116
<211> LENGTH: 37
<212> TYPE: DNA
<213> ORGANISM: Artificial
<220> FEATURE:
<223> OTHER INFORMATION: m2 -10 Pm region

<400> SEQUENCE: 116
tctagaatgg catacccctt aggcttttgc aacatgt                  37

<210> SEQ ID NO 117
<211> LENGTH: 37
<212> TYPE: DNA
<213> ORGANISM: Artificial
<220> FEATURE:
<223> OTHER INFORMATION: 11G -10 Pm region

<400> SEQUENCE: 117
tctagaatag actacccctt agacttatgc aacatgt                  37

<210> SEQ ID NO 118
<211> LENGTH: 37
<212> TYPE: DNA
<213> ORGANISM: Artificial
<220> FEATURE:
<223> OTHER INFORMATION: 4E -10 Pm region

<400> SEQUENCE: 118
tctagaatag cctacccatt aggctttatc aacatgt                  37

<210> SEQ ID NO 119
<211> LENGTH: 36
<212> TYPE: DNA

<213> ORGANISM: Artificial
<220> FEATURE:
<223> OTHER INFORMATION: 7B -10 Pm region

<400> SEQUENCE: 119
tctagaaagg cctaccccttt aaactttagc acatgt       36

<210> SEQ ID NO 120
<211> LENGTH: 38
<212> TYPE: DNA
<213> ORGANISM: Artificial
<220> FEATURE:
<223> OTHER INFORMATION: wt -10 Pm region

<400> SEQUENCE: 120
tctagaaagg cctaccccttt aggctttatg caacatgt       38

<210> SEQ ID NO 121
<211> LENGTH: 36
<212> TYPE: DNA
<213> ORGANISM: Artificial
<220> FEATURE:
<223> OTHER INFORMATION: Un3 -10 Pm region

<400> SEQUENCE: 121
tctagaaagg cctacctgtt agacttatgc acatgt       36

<210> SEQ ID NO 122
<211> LENGTH: 36
<212> TYPE: DNA
<213> ORGANISM: Artificial
<220> FEATURE:
<223> OTHER INFORMATION: 5d -10 Pm region

<400> SEQUENCE: 122
tctagaaagg tttaccccttt atactttatg caatgt       36

<210> SEQ ID NO 123
<211> LENGTH: 38
<212> TYPE: DNA
<213> ORGANISM: Artificial
<220> FEATURE:
<223> OTHER INFORMATION: Un19 -10 Pm region

<400> SEQUENCE: 123
tctagaaagg ccaacgtgtt aggctttatg caacatgt       38

<210> SEQ ID NO 124
<211> LENGTH: 38
<212> TYPE: DNA
<213> ORGANISM: Artificial
<220> FEATURE:
<223> OTHER INFORMATION: Un21 -10 Pm region

<400> SEQUENCE: 124
tctagaaagg ccttcgtgtt aggctttatg caacatgt       38

<210> SEQ ID NO 125
<211> LENGTH: 36
<212> TYPE: DNA
<213> ORGANISM: Artificial
<220> FEATURE:
<223> OTHER INFORMATION: 7B -10 Pm region

<400> SEQUENCE: 125
tctagaaagg cctaccccttt aaactttagc acatgt       36

```
<210> SEQ ID NO 126
<211> LENGTH: 36
<212> TYPE: DNA
<213> ORGANISM: Artificial
<220> FEATURE:
<223> OTHER INFORMATION: 7-2d -10 Pm region

<400> SEQUENCE: 126
tctagaaatg cctacccctt atactttagc acatgt                              36

<210> SEQ ID NO 127
<211> LENGTH: 36
<212> TYPE: DNA
<213> ORGANISM: Artificial
<220> FEATURE:
<223> OTHER INFORMATION: 7-2g -10 Pm region

<400> SEQUENCE: 127
tctagaaagg cctacacctt atagtttagc acatgt                              36

<210> SEQ ID NO 128
<211> LENGTH: 36
<212> TYPE: DNA
<213> ORGANISM: Artificial
<220> FEATURE:
<223> OTHER INFORMATION: 7-3b -10 Pm region

<400> SEQUENCE: 128
tctagaaagt cctacccctt acactttagc acatgt                              36

<210> SEQ ID NO 129
<211> LENGTH: 36
<212> TYPE: DNA
<213> ORGANISM: Artificial
<220> FEATURE:
<223> OTHER INFORMATION: 7-4c -10 Pm region

<400> SEQUENCE: 129
tctagaaaga cctacacctt aaactttacc acatgt                              36

<210> SEQ ID NO 130
<211> LENGTH: 36
<212> TYPE: DNA
<213> ORGANISM: Artificial
<220> FEATURE:
<223> OTHER INFORMATION: 7-4g -10 Pm region

<400> SEQUENCE: 130
tctagaacgg cctaccactt aaactatagc acatgt                              36

<210> SEQ ID NO 131
<211> LENGTH: 36
<212> TYPE: DNA
<213> ORGANISM: Artificial
<220> FEATURE:
<223> OTHER INFORMATION: 7-4h -10 Pm region

<400> SEQUENCE: 131
tctagaaaca cctacccctt aaactttagc acatgt                              36

<210> SEQ ID NO 132
<211> LENGTH: 36
<212> TYPE: DNA
<213> ORGANISM: Artificial
<220> FEATURE:
```

<210> SEQ ID NO 132
<211> LENGTH: 36
<212> TYPE: DNA
<213> ORGANISM: Artificial
<220> FEATURE:
<223> OTHER INFORMATION: 7-5b -10 Pm region

<400> SEQUENCE: 132
tctagaacgg gctacgcctt aaactttagc acatgt                                    36

<210> SEQ ID NO 133
<211> LENGTH: 36
<212> TYPE: DNA
<213> ORGANISM: Artificial
<220> FEATURE:
<223> OTHER INFORMATION: 7-5d -10 Pm region

<400> SEQUENCE: 133
tctagaaacg cctaccccct aaactttagc acatgt                                    36

<210> SEQ ID NO 134
<211> LENGTH: 36
<212> TYPE: DNA
<213> ORGANISM: Artificial
<220> FEATURE:
<223> OTHER INFORMATION: 7-5f -10 Pm region

<400> SEQUENCE: 134
tctagaaagt tccaccccct aaactttagc acatgt                                    36

<210> SEQ ID NO 135
<211> LENGTH: 36
<212> TYPE: DNA
<213> ORGANISM: Artificial
<220> FEATURE:
<223> OTHER INFORMATION: 7-5h -10 Pm region

<400> SEQUENCE: 135
tctagaaagg actacccctt atactttagc acatgt                                    36

<210> SEQ ID NO 136
<211> LENGTH: 36
<212> TYPE: DNA
<213> ORGANISM: Artificial
<220> FEATURE:
<223> OTHER INFORMATION: 7-10f -10 Pm region

<400> SEQUENCE: 136
tctagaaagg ccaatccctt acactttagc acatgt                                    36

<210> SEQ ID NO 137
<211> LENGTH: 36
<212> TYPE: DNA
<213> ORGANISM: Artificial
<220> FEATURE:
<223> OTHER INFORMATION: 7-11h -10 Pm region

<400> SEQUENCE: 137
tctagaaagg ccaatccctt acactttagc acatgt                                    36

<210> SEQ ID NO 138
<211> LENGTH: 38
<212> TYPE: DNA
<213> ORGANISM: Artificial
<220> FEATURE:
<223> OTHER INFORMATION: wt -10 Pm region

<400> SEQUENCE: 138
tctagaaagg cctaccccct aggctttatg caacatgt                                  38

<210> SEQ ID NO 139
<211> LENGTH: 36
<212> TYPE: DNA
<213> ORGANISM: Artificial
<220> FEATURE:
<223> OTHER INFORMATION: 3G -10 Pm region

<400> SEQUENCE: 139
tctagaatgg cctatccctt atgcttatgc aaatgt                          36

<210> SEQ ID NO 140
<211> LENGTH: 36
<212> TYPE: DNA
<213> ORGANISM: Artificial
<220> FEATURE:
<223> OTHER INFORMATION: 5D -10 Pm region

<400> SEQUENCE: 140
tctagaaagg tttaccccttt atactttatg caatgt                         36

<210> SEQ ID NO 141
<211> LENGTH: 36
<212> TYPE: DNA
<213> ORGANISM: Artificial
<220> FEATURE:
<223> OTHER INFORMATION: 7B -10 Pm region

<400> SEQUENCE: 141
tctagaaagg cctaccccttt aaactttagc acatgt                         36

<210> SEQ ID NO 142
<211> LENGTH: 37
<212> TYPE: DNA
<213> ORGANISM: Artificial
<220> FEATURE:
<223> OTHER INFORMATION: 11g -10 Pm region

<400> SEQUENCE: 142
tctagaatag actaccccttt agacttatgc aacatgt                        37

<210> SEQ ID NO 143
<211> LENGTH: 38
<212> TYPE: DNA
<213> ORGANISM: Artificial
<220> FEATURE:
<223> OTHER INFORMATION: Pm-wt

<400> SEQUENCE: 143
tctagaaagg cctaccccttt aggctttatg caacatgt                       38

<210> SEQ ID NO 144
<211> LENGTH: 36
<212> TYPE: DNA
<213> ORGANISM: Artificial
<220> FEATURE:
<223> OTHER INFORMATION: Pm-7B-4g

<400> SEQUENCE: 144
tctagaacgg cctaccactt aaactatagc acatgt                          36

<210> SEQ ID NO 145
<211> LENGTH: 36
<212> TYPE: DNA
<213> ORGANISM: Artificial
<220> FEATURE:
<223> OTHER INFORMATION: Pm-7b-2g

```
<400> SEQUENCE: 145
tctagaaagg cctacacctt atagtttagc acatgt                              36

<210> SEQ ID NO 146
<211> LENGTH: 34
<212> TYPE: DNA
<213> ORGANISM: Artificial
<220> FEATURE:
<223> OTHER INFORMATION: Pm-7b4g-UTR-wt

<400> SEQUENCE: 146
acatgtacaa taataatgga gtcatgaaca tatg                                34

<210> SEQ ID NO 147
<211> LENGTH: 34
<212> TYPE: DNA
<213> ORGANISM: Artificial
<220> FEATURE:
<223> OTHER INFORMATION: Pm-7b4g-UTR-C2

<400> SEQUENCE: 147
acatgtacaa caatattgga atcatgaaca tatg                                34

<210> SEQ ID NO 148
<211> LENGTH: 34
<212> TYPE: DNA
<213> ORGANISM: Artificial
<220> FEATURE:
<223> OTHER INFORMATION: Pm-7b4g-UTR-A2

<400> SEQUENCE: 148
acatgtacaa tcataatgga atcatgaaca tatg                                34

<210> SEQ ID NO 149
<211> LENGTH: 34
<212> TYPE: DNA
<213> ORGANISM: Artificial
<220> FEATURE:
<223> OTHER INFORMATION: Pm-7b4g-UTR-C4

<400> SEQUENCE: 149
acatgtacat taattatgga atcatgaaca tatg                                34

<210> SEQ ID NO 150
<211> LENGTH: 34
<212> TYPE: DNA
<213> ORGANISM: Artificial
<220> FEATURE:
<223> OTHER INFORMATION: Pm-7b4g-UTR-H2

<400> SEQUENCE: 150
acatgtacaa caataatgga atcattaaca tatg                                34

<210> SEQ ID NO 151
<211> LENGTH: 34
<212> TYPE: DNA
<213> ORGANISM: Artificial
<220> FEATURE:
<223> OTHER INFORMATION: Pm-7b4g-UTR-E2

<400> SEQUENCE: 151
acatgtacaa taattatgga atcattaaca tatg                                34

<210> SEQ ID NO 152
<211> LENGTH: 34
```

```
<212> TYPE: DNA
<213> ORGANISM: Artificial
<220> FEATURE:
<223> OTHER INFORMATION: Pm-7b4g-UTR-B2

<400> SEQUENCE: 152
acatgtacaa aactaatgga atcattaaca tatg                              34

<210> SEQ ID NO 153
<211> LENGTH: 34
<212> TYPE: DNA
<213> ORGANISM: Artificial
<220> FEATURE:
<223> OTHER INFORMATION: Pm-7b4g-UTR-F3

<400> SEQUENCE: 153
acatgttcaa taataatgga atcattaaca tatg                              34

<210> SEQ ID NO 154
<211> LENGTH: 34
<212> TYPE: DNA
<213> ORGANISM: Artificial
<220> FEATURE:
<223> OTHER INFORMATION: Pm-7b4g-UTR-E6

<400> SEQUENCE: 154
acatgtacaa taatatagga atcattaaca tatg                              34

<210> SEQ ID NO 155
<211> LENGTH: 34
<212> TYPE: DNA
<213> ORGANISM: Artificial
<220> FEATURE:
<223> OTHER INFORMATION: Pm-7b4g-UTR-H3

<400> SEQUENCE: 155
acatgtacaa taaaactgga atcattaaca tatg                              34

<210> SEQ ID NO 156
<211> LENGTH: 34
<212> TYPE: DNA
<213> ORGANISM: Artificial
<220> FEATURE:
<223> OTHER INFORMATION: Pm-7b4g-UTR-F11

<400> SEQUENCE: 156
acatgtacaa tcaaaatgga atcatgaaca tatg                              34

<210> SEQ ID NO 157
<211> LENGTH: 34
<212> TYPE: DNA
<213> ORGANISM: Artificial
<220> FEATURE:
<223> OTHER INFORMATION: Pm-7b4g-UTR-B3

<400> SEQUENCE: 157
acatgtacaa tataaacgga accatgaaca tatg                              34

<210> SEQ ID NO 158
<211> LENGTH: 34
<212> TYPE: DNA
<213> ORGANISM: Artificial
<220> FEATURE:
<223> OTHER INFORMATION: Pm-7b4g-UTR-A3

<400> SEQUENCE: 158
```

```
acatgtacaa cataaatgga atcatgaaca tatg                              34

<210> SEQ ID NO 159
<211> LENGTH: 34
<212> TYPE: DNA
<213> ORGANISM: Artificial
<220> FEATURE:
<223> OTHER INFORMATION: Pm-7b4g-UTR-2

<400> SEQUENCE: 159
acatgttcaa tcataatgga atcatgtaca tatg                              34

<210> SEQ ID NO 160
<211> LENGTH: 34
<212> TYPE: DNA
<213> ORGANISM: Artificial
<220> FEATURE:
<223> OTHER INFORMATION: Pm-7b4g-UTR-C3

<400> SEQUENCE: 160
acatgtacaa gactttttgga atcatgaaca tatg                             34

<210> SEQ ID NO 161
<211> LENGTH: 34
<212> TYPE: DNA
<213> ORGANISM: Artificial
<220> FEATURE:
<223> OTHER INFORMATION: Pm-7b4g-UTR-E3

<400> SEQUENCE: 161
acatgttcaa taataatgga atcatgcaca tatg                              34

<210> SEQ ID NO 162
<211> LENGTH: 34
<212> TYPE: DNA
<213> ORGANISM: Artificial
<220> FEATURE:
<223> OTHER INFORMATION: Pm-7b4g-UTR-G3

<400> SEQUENCE: 162
acatgtacaa caatgatgga atcatgaaca tatg                              34

<210> SEQ ID NO 163
<211> LENGTH: 34
<212> TYPE: DNA
<213> ORGANISM: Artificial
<220> FEATURE:
<223> OTHER INFORMATION: Pm-7b4g-UTR-F2

<400> SEQUENCE: 163
acatgtacaa caaaaagcga gtcctgaaca tatg                              34
```